(12) United States Patent
Jang et al.

(10) Patent No.: US 11,264,574 B2
(45) Date of Patent: Mar. 1, 2022

(54) COMPOSITION FOR ORGANIC OPTOELECTRONIC ELEMENT, ORGANIC OPTOELECTRONIC ELEMENT, AND DISPLAY DEVICE

(71) Applicant: SAMSUNG SDI CO., LTD., Yongin-si (KR)

(72) Inventors: Kipo Jang, Suwon-si (KR); Jun Seok Kim, Suwon-si (KR); Jinhyun Lui, Suwon-si (KR); Chang Ju Shin, Suwon-si (KR); Sujin Han, Suwon-si (KR); Youngkwon Kim, Suwon-si (KR); Eun Sun Yu, Suwon-si (KR); Sung-Hyun Jung, Suwon-si (KR); Ho Kuk Jung, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 437 days.

(21) Appl. No.: 16/321,228

(22) PCT Filed: May 10, 2017

(86) PCT No.: PCT/KR2017/004835
§ 371 (c)(1),
(2) Date: Jan. 28, 2019

(87) PCT Pub. No.: WO2018/021663
PCT Pub. Date: Feb. 1, 2018

(65) Prior Publication Data
US 2019/0181351 A1  Jun. 13, 2019

(30) Foreign Application Priority Data
Jul. 29, 2016 (KR) .......... 10-2016-0097205

(51) Int. Cl.
*H01L 51/00* (2006.01)
*C07D 405/14* (2006.01)
(Continued)

(52) U.S. Cl.
CPC ........ *H01L 51/0067* (2013.01); *C07D 209/82* (2013.01); *C07D 251/24* (2013.01);
(Continued)

(58) Field of Classification Search
None
See application file for complete search history.

(56) References Cited

U.S. PATENT DOCUMENTS 6,229,012 B1   5/2001  Hu et al.
9,209,406 B2  12/2015  Mizutani et al.
(Continued)

FOREIGN PATENT DOCUMENTS

CN  102850329 A   1/2013
CN  103380508 A  10/2013
(Continued)

OTHER PUBLICATIONS

Yu, Organic Electronics, 38, 2016, 301-306.
(Continued)

*Primary Examiner* — Robert S Loewe
(74) *Attorney, Agent, or Firm* — Lee IP Law, PC

(57) ABSTRACT

The present invention relates to a composition for an organic optoelectronic element, an organic optoelectronic element employing the composition, and a display device, wherein the composition comprises: a first compound for an organic optoelectronic element, represented by Chemical Formula 1; and a second compound for an organic optoelectronic element, comprising a combination of a moiety represented by
(Continued)

Chemical Formula 2 and a moiety represented by Chemical Formula 3. The details of chemical formulas 1 to 3 are as defined in the specification.

10 Claims, 1 Drawing Sheet

(51) Int. Cl.
    *C07D 409/14*     (2006.01)
    *C07D 333/76*     (2006.01)
    *C09K 11/06*     (2006.01)
    *H01L 51/50*     (2006.01)
    *C07D 209/82*     (2006.01)
    *C07D 251/24*     (2006.01)
    *C07D 405/10*     (2006.01)
    *C07D 487/04*     (2006.01)

(52) U.S. Cl.
    CPC ......... *C07D 333/76* (2013.01); *C07D 405/10* (2013.01); *C07D 405/14* (2013.01); *C07D 409/14* (2013.01); *C07D 487/04* (2013.01); *C09K 11/06* (2013.01); *H01L 51/00* (2013.01); *H01L 51/0073* (2013.01); *H01L 51/0074* (2013.01); *H01L 51/50* (2013.01); *H01L 51/5004* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/552* (2013.01)

(56) References Cited

U.S. PATENT DOCUMENTS

| | | | |
|---|---|---|---|
| 9,893,290 B2 | 2/2018 | Min | |
| 2004/0164292 A1 | 8/2004 | Tung | |
| 2006/0046342 A1 | 3/2006 | Karg et al. | |
| 2007/0141387 A1 | 6/2007 | Nakano et al. | |
| 2013/0264560 A1 | 10/2013 | Dobbs et al. | |
| 2014/0001456 A1 | 1/2014 | Mizutani et al. | |
| 2014/0361258 A1 | 12/2014 | Hwang et al. | |
| 2015/0028320 A1 | 1/2015 | Kinoshita et al. | |
| 2015/0171336 A1 | 6/2015 | Park et al. | |
| 2015/0171340 A1* | 6/2015 | Lee .................. H01L 51/0067 257/40 |
| 2015/0207082 A1* | 7/2015 | Dyatkin ............. C07D 491/147 257/40 |
| 2015/0349268 A1 | 12/2015 | Zeng et al. | |
| 2016/0028021 A1* | 1/2016 | Zeng ................... H01L 51/0073 257/40 |
| 2016/0329502 A1 | 11/2016 | Dyatkin et al. | |
| 2017/0025618 A1 | 1/2017 | Zheng et al. | |
| 2017/0117488 A1* | 4/2017 | Ahn .................... H01L 51/0094 |
| 2018/0033975 A1* | 2/2018 | Kim .................... C07D 403/10 |

FOREIGN PATENT DOCUMENTS

| | | |
|---|---|---|
| CN | ON 104271703 A | 1/2015 |
| CN | 103232843 B | 2/2015 |
| CN | 104812750 A | 7/2015 |
| CN | 104885247 A | 9/2015 |
| CN | 104995187 A | 10/2015 |
| CN | 105153130 A | 12/2015 |
| CN | 105315219 A | 2/2016 |
| CN | 105315265 A | 2/2016 |
| CN | 105359290 A | 2/2016 |
| CN | 105473684 A | 4/2016 |
| CN | 105601612 A | 5/2016 |
| CN | 107093677 A | 8/2017 |
| CN | 107325090 A | 11/2017 |
| CN | 108290854 A | 7/2018 |
| EP | 2 966 706 A2 | 1/2016 |
| EP | 3 268 449 A1 | 2/2016 |
| JP | 2014/040423 A | 3/2014 |
| JP | 2014-123687 A | 7/2014 |
| JP | 5541167 B2 | 7/2014 |
| JP | 2014-157947 A | 8/2014 |
| JP | 5847420 B2 | 1/2016 |
| JP | 2016/019002 A | 2/2016 |
| JP | 2016-506414 A | 3/2016 |
| JP | 2016-525081 A | 8/2016 |
| JP | 2018-514081 A | 5/2018 |
| KR | 10-2011-0096453 | 8/2011 |
| KR | 10-2010-0118690 | 11/2011 |
| KR | 10-2012-0129733 A | 11/2012 |
| KR | 10-2013-0036048 A | 4/2013 |
| KR | 10-2013-0061371 | 6/2013 |
| KR | 10-2014-0005804 A | 1/2014 |
| KR | 10-2014-0010133 | 1/2014 |
| KR | 10-1423067 B1 | 7/2014 |
| KR | 10-2014-0144550 A | 12/2014 |
| KR | 10-2015-0036736 | 4/2015 |
| KR | 10-2015-0042335 A | 4/2015 |
| KR | 10-2015-0070860 A | 6/2015 |
| KR | 10-1542714 B1 | 7/2015 |
| KR | 10-2015-0116776 A | 10/2015 |
| KR | 10-2015-0129282 A | 11/2015 |
| KR | 10-2015-0131998 A | 11/2015 |
| KR | 10-2015-0136942 | 12/2015 |
| KR | 10-2016-0006633 A | 1/2016 |
| KR | 10-1593465 B1 | 2/2016 |
| KR | 10-2016-0028524 A | 3/2016 |
| KR | 10-2016-0034528 A | 3/2016 |
| KR | 2016-37909 | 3/2016 |
| KR | 10-2016-0038006 A | 4/2016 |
| KR | 10-2016-0055556 A | 5/2016 |
| KR | 10-2016-0080090 A | 7/2016 |
| KR | 10-2016-0110078 A | 9/2016 |
| KR | 10-2017-0022865 | 3/2017 |
| KR | 10-2017-0089599 A | 8/2017 |
| KR | 10-2017-0116992 A | 10/2017 |
| KR | 10-2017-0141144 A | 12/2017 |
| TW | 201609712 A | 3/2016 |
| TW | 201619152 A | 6/2016 |
| WO | WO 2010-044342 A1 | 4/2010 |
| WO | WO 2013/077352 A1 | 5/2013 |
| WO | WO 2014/054912 A1 | 4/2014 |
| WO | WO 2014208755 A1 | 12/2014 |
| WO | WO 2015/000549 A1 | 1/2015 |
| WO | WO 2015/156587 A1 | 10/2015 |
| WO | WO 2015/160224 A1 | 10/2015 |
| WO | WO 2016/076384 A1 | 5/2016 |
| WO | WO 2016084962 A1 | 6/2016 |
| WO | WO-2016148390 A1 * | 9/2016 .......... C07F 15/0033 |
| WO | WO 2016/172414 A1 | 10/2016 |
| WO | WO 2017/016630 A1 | 2/2017 |
| WO | WO 2017/146466 A1 | 8/2017 |
| WO | WO 2017/171420 A1 | 10/2017 |
| WO | WO 2018/016742 A1 | 1/2018 |
| WO | WO 2018/021663 A1 | 2/2018 |
| WO | WO 2018/062659 A1 | 4/2018 |
| WO | WO 2018/093026 A1 | 5/2018 |
| WO | WO 2018/097461 A1 | 5/2018 |
| WO | WO 2018/128255 A1 | 7/2018 |

OTHER PUBLICATIONS

U.S. Office action received in co pending U.S. Appl. No. 16/099,507, dated Apr. 16, 2021.
U.S. Office action received in co pending U.S. Appl. No. 16/099,523, dated Apr. 19, 2021.
Office action received in copending related U.S. Appl. No. 16/097,657.
U.S. Office Action dated Jan. 13, 2021 from Co-pending U.S. Appl. No. 16/468,779.
European Search Report dated Dec. 19, 2019, Application No. 17820373.3.
European Search Report dated Jan. 8, 2020, Application No. 17820372.5.
International Search Report dated Apr. 24, 2017.

(56) References Cited

OTHER PUBLICATIONS

Extended European Search Report dated Feb. 17, 2020, European Patent Application No. 17827792.7.
Extended European Search Report dated Feb. 28, 2020, corresponding European Patent Application No. 17834608.6.
Provisional double patenting rejection over claims of the above-identified application; USPTO Office action dated Feb. 19, 2021, in U.S. Appl. No. 15/769,141.
Japanese Office action dated Sep. 29, 2020, received in Japanese Application No. 2018-568699.
Japanese Notice of Allowance dated Oct. 6, 2020, received in Japanese Application No. 2019-503551.
European Office action dated Mar. 25, 2021.
Final Office action received in Co-pending related U.S. Appl. No. 16/099,507, dated Sep. 24, 2021.
Office Action received in Co-pending U.S. Appl. No. 16/099,523 dated Oct. 7, 2021.
U.S. Advisory action received in copending U.S. Appl. No. 16/099,507 dated Dec. 1, 2021.

* cited by examiner

【Figure 1】
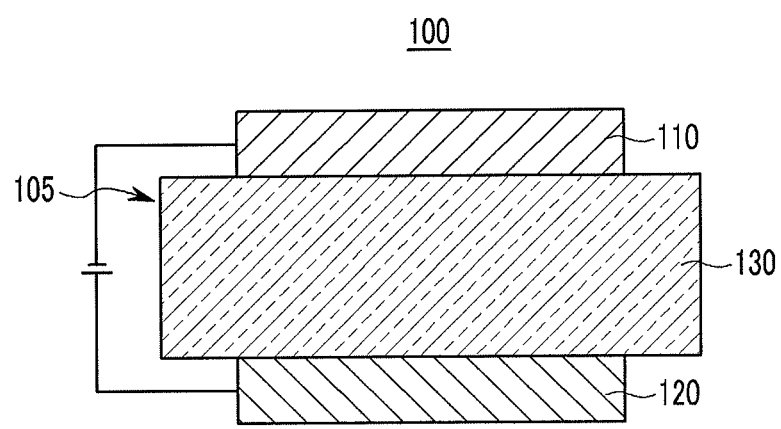
【Figure 2】
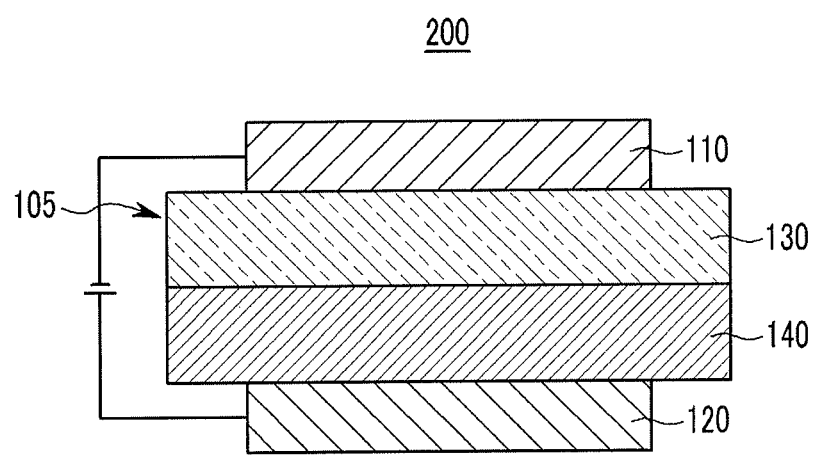

COMPOSITION FOR ORGANIC OPTOELECTRONIC ELEMENT, ORGANIC OPTOELECTRONIC ELEMENT, AND DISPLAY DEVICE

CROSS REFERENCE TO RELATED APPLICATIONS

This is the U.S. national phase application based on PCT Application No. PCT/KR2017/004835, filed May 10, 2017, which is based on Korean Patent Application No. 10-2016-0097205, filed Jul. 29, 2016, the entire contents of all of which are hereby incorporated by reference.

TECHNICAL FIELD

A composition for an organic optoelectronic device, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a composition for an organic optoelectronic device capable of realizing an organic optoelectronic device having high efficiency and a long life-span.

Another embodiment provides an organic optoelectronic device including the composition.

Yet another embodiment provides a display device including the organic optoelectronic device.

Technical Solution

According to an embodiment, a composition for an organic optoelectronic device includes a first compound for an organic optoelectronic device represented by Chemical Formula 1; and a second compound for an organic optoelectronic device consisting of a moiety represented by Chemical Formula 2 and a moiety represented by Chemical Formula 3.

[Chemical Formula 1]

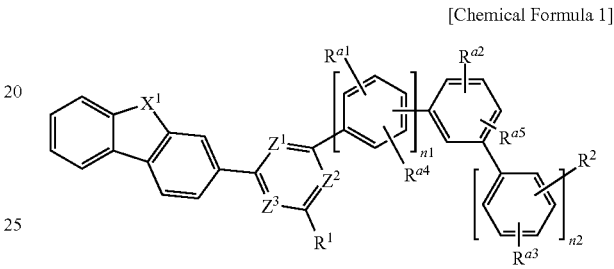

In Chemical Formula 1,
$Z^1$ to $Z^3$ are independently N or $CR^b$,
at least two of $Z^1$ to $Z^3$ are N,
$X^1$ is O or S,
$R^1$ and $R^2$ are independently a substituted or unsubstituted C6 to C30 aryl group, a substituted or unsubstituted C2 to C30 heterocyclic group, or a combination thereof,
$R^{a1}$ to $R^{a5}$ and $R^b$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C20 heterocyclic group, or a combination thereof, and
n1 and n2 are independently one of integers of 0 to 2;

[Chemical Formula 2]

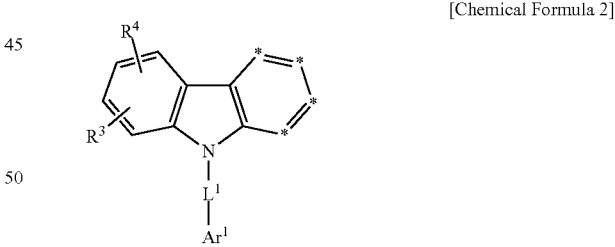

[Chemical Formula 3]

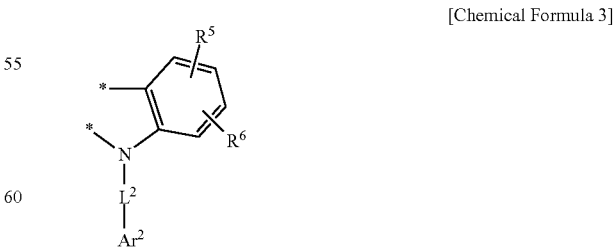

wherein, in Chemical Formulae 2 and 3,
$Ar^1$ and $Ar^2$ are independently a substituted or unsubstituted C6 to C30 aryl group, a substituted or unsubstituted C2 to C30 heterocyclic group, or a combination thereof, two adjacent *'s of Chemical Formula 2 are bound to two adjacent *'s of Chemical Formula 3 to provide a fused ring and *'s of not providing the fused ring in Chemical Formula 2 are independently C-$L^a$-$R^c$, $R^c$ and $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^a$, $L^1$, and $L^2$ are independently a single bond, a substituted or unsubstituted C6 to C30 arylene group, a substituted or unsubstituted C2 to C30 heteroarylene group, or a combination thereof;

wherein the "substituted" of Chemical Formulae 1 to 3 refers to replacement of at least one hydrogen by deuterium, a C1 to C4 alkyl group, a C6 to C18 aryl group, or a C2 to C18 heteroaryl group.

According to another embodiment, an organic optoelectronic device includes an anode and a cathode facing each other and at least one organic layer disposed between the anode and the cathode, wherein the organic layer includes the composition for an organic optoelectronic device.

According to yet another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a fluoro group, a C1 to C10 trifluoroalkyl group, a cyano group, or a combination thereof.

In examples of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, specific examples of the present invention, the "substituted" refers to replacement of at least one hydrogen of a substituent or a compound by deuterium, a methyl group, an ethyl group, a propyl group, a butyl group, a phenyl group, a biphenyl group, a terphenyl group, a naphthyl group, a triphenylene group, a fluorenyl group, a pyridinyl group, a pyrimidinyl group, a carbazolyl group, a dibenzofuranyl group, or a dibenzothiophenyl group. In the most specific examples of the present invention, the "substituted" for example refers to replacement of at least one hydrogen of a substituent or a compound by a phenyl group, a para-biphenyl group, a meta-biphenyl group, a naphthyl group, a triphenylene group, a pyridinyl group, a pyrimidinyl group, a 9-carbazolyl group, a 2-dibenzofuranyl group, a 3-dibenzofuranyl group, a 2-dibenzothiophenyl group, or a 3-dibenzothiophenyl group.

In the present specification when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes a first compound for an organic optoelectronic device; and a second compound for an organic optoelectronic device.

The first compound for an organic optoelectronic device may be represented by Chemical Formula 1.

[Chemical Formula 1]

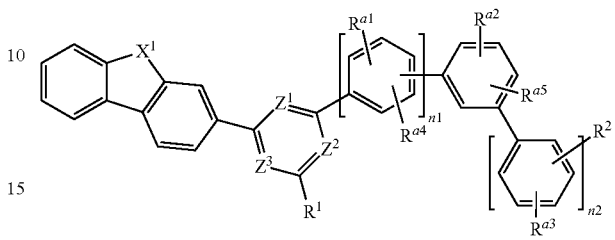

In Chemical Formula 1,
$Z^1$ to $Z^3$ are independently N or $CR^b$,
at least two of $Z^1$ to $Z^3$ are N,
$X^1$ is O or S,
$R^1$ and $R^2$ are independently a substituted or unsubstituted C6 to C30 aryl group, a substituted or unsubstituted C2 to C30 heterocyclic group, or a combination thereof,
$R^{a1}$ to $R^{a5}$ and $R^b$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C20 heterocyclic group, or a combination thereof, and
n1 and n2 are independently one of integers of 0 to 2.

The "substituted" of Chemical Formula 1 refers to replacement of at least one hydrogen by deuterium, a C1 to C4 alkyl group, a C6 to C18 aryl group, or a C2 to C18 heteroaryl group. In one example of the present invention, the "substituted" of Chemical Formula 1 refers to replacement of at least one hydrogen by deuterium, a C1 to C4 alkyl group, a C6 to C12 aryl group, or a C2 to C12 heteroaryl group. In a specific example of the present invention, the "substituted" of Chemical Formula 1 refers to replacement of at least one hydrogen by deuterium, a phenyl group, a meta-biphenyl group, a para-biphenyl group, a naphthyl group, a dibenzofuranyl group, a dibenzothiophenyl group, a pyrimidinyl group, or a triazinyl group.

A compound for an organic optoelectronic device according to the present invention includes an ET core including an N-containing 6-membered ring that includes a substituent directly linked with dibenzofuran or dibenzothiophene at a position No. 3 without a linking group, and thereby a LUMO energy band is effectively expanded, planarity of a molecular structure is increased, and the compound may become a structure capable of accepting electrons when an electric field is applied, and accordingly an organic optoelectronic device including the compound for an organic optoelectronic device may exhibit a lowered driving voltage. Such a LUMO expansion and ring fusion increase stability for electrons of the ET core and life-span of a device is effectively improved.

In addition, interactions with adjacent molecules may be suppressed and crystallization is decreased due to steric hinderance characteristics by at least one meta-bound arylene and accordingly efficiency and life-span characteristics of an organic optoelectronic device including the compound for an organic optoelectronic device may be improved.

A kinked moiety such as the meta-bound arylene increases a glass transition temperature (Tg) of a compound and stability of a compound may be increased and degradation may be suppressed when it is applied to a device.

Particularly, when the second compound for an organic optoelectronic device having relatively strong hole characteristics is used with the first compound for an organic optoelectronic device in a light emitting layer, charges in the light emitting layer are balanced and an organic light emitting diode having a long life-span may be realized.

In one example of the present invention, $R^{a1}$ to $R^{a5}$ and $R^b$ may independently be hydrogen, deuterium, a substituted or unsubstituted C1 to C4 alkyl group, or a substituted or unsubstituted C6 to C18 aryl group. In addition, $R^{a1}$ to $R^{a5}$ and $R^b$ may independently be hydrogen, a phenyl group, a naphthyl group, a biphenyl group, a triphenylene group, or a terphenyl group.

In an example embodiment of the present invention, an ET core consisting of the $Z^1$ to $Z^3$ may be pyrimidine where at least two OF $Z^1$ to $Z^3$ are N and triazine where all $Z^1$ to $Z^3$ are N. When the $Z^1$ to $Z^3$ are $CR^b$, $R^b$ may be for example hydrogen, deuterium, a cyano group, a nitro group, a substituted or unsubstituted C1 to C4 alkyl group, or a substituted or unsubstituted C6 to C12 aryl group, in a specific example embodiment of the present invention, the $R^b$ may be hydrogen, deuterium, or a phenyl group, and in the most specific example embodiment of the present invention, all $R^b$ may be hydrogen.

For example, Chemical Formula 1 may be represented by Chemical Formula 1-I, Chemical Formula 1-II, or Chemical Formula 1-III, and may be specifically represented by Chemical Formula 1-I or Chemical Formula 1-II.

In an example embodiment of the present invention, the $R^1$ and $R^2$ may independently be a substituted or unsubstituted C6 to C20 aryl group, or a substituted or unsubstituted C2 to C30 heterocyclic group, specifically a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, or a substituted or unsubstituted quinoxalinyl group, and more specifically substituted or unsubstituted phenyl group, a substituted or unsubstituted biphenyl group, a substituted or unsubstituted terphenyl group, a substituted or unsubstituted dibenzofuranyl group, a substituted or unsubstituted dibenzothiophenyl group, a substituted or unsubstituted pyrimidinyl group, or a substituted or unsubstituted triazinyl group.

For example, they may be selected from substituents of Group I.

[Chemical Formula 1-I]

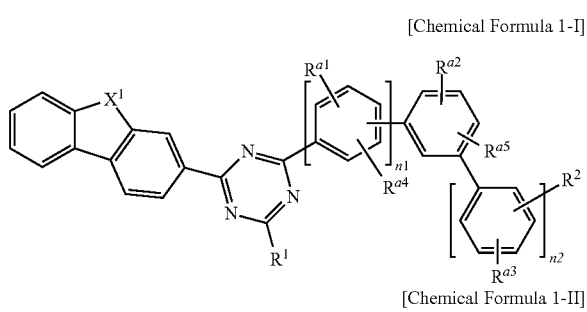

[Chemical Formula 1-II]

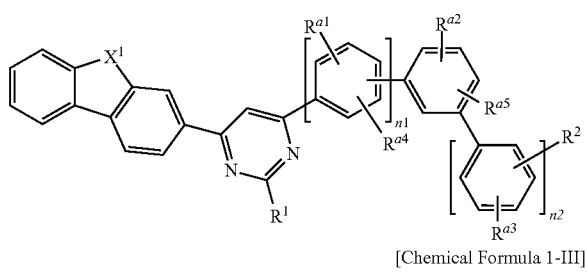

[Chemical Formula 1-III]

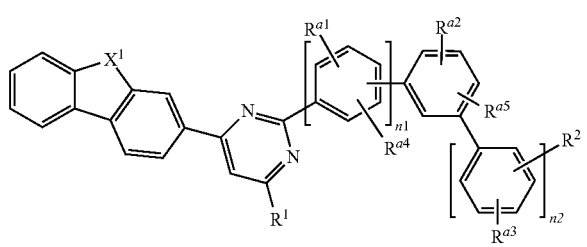

[Group I]

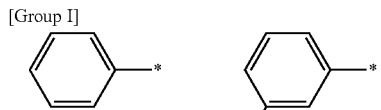
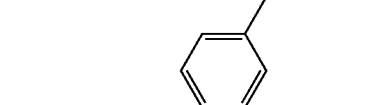
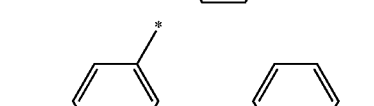
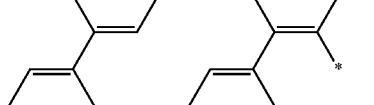
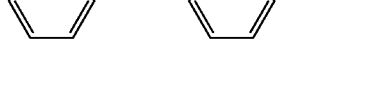
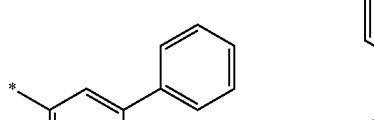

In Chemical Formula 1-I, Chemical Formula 1-II and Chemical Formula 1-III, $X^1$, $R^1$ and $R^2$, $R^{a1}$ to $R^{a5}$, n1, and n2 are the same as described above.

-continued

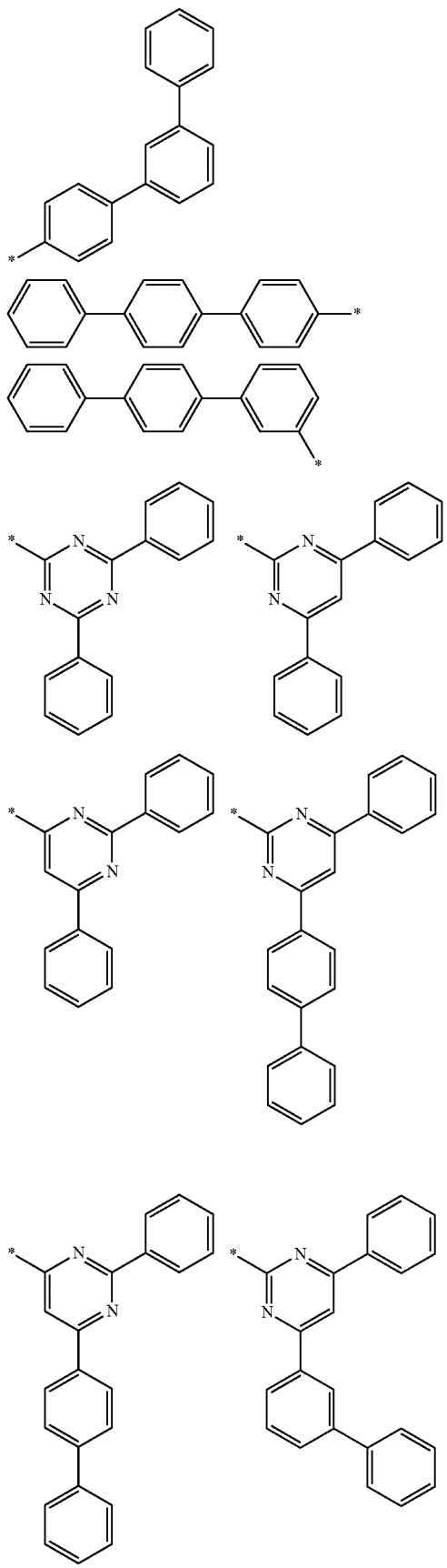

-continued

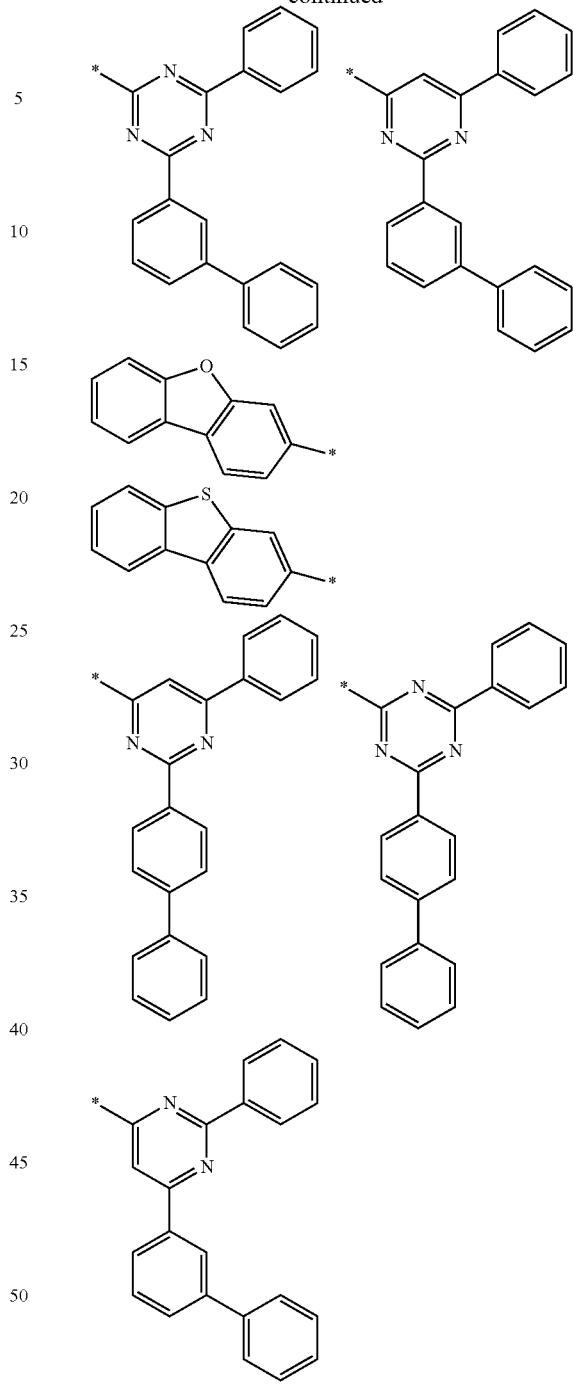

In Group I, * is a linking point with an adjacent atom.

In addition, in an example embodiment of the present invention, the $R^{a1}$ to $R^{a5}$ may independently be hydrogen, deuterium, a substituted or unsubstituted C1 to C4 alkyl group, a substituted or unsubstituted C6 to C20 aryl group, or a substituted or unsubstituted C2 to C20 heterocyclic group, specifically is hydrogen, a substituted or unsubstituted C1 to 04 alkyl group or a substituted or unsubstituted C6 to C20 aryl group, and more specifically substituted or unsubstituted phenyl group, a substituted or unsubstituted meta-biphenyl group, a substituted or unsubstituted para-biphenyl group, a substituted or unsubstituted naphthyl group, or a substituted or unsubstituted fluorenyl group.

In the most specific example embodiment of the present invention, all $R^{a1}$ to $R^{a5}$ may be hydrogen or one of the $R^{a2}$ and the $R^{a5}$ may be a substituted or unsubstituted C1 to C4 alkyl group or a substituted or unsubstituted C6 to C20 aryl group, for example, a phenyl group, a biphenyl group, a terphenyl group, or a naphthyl group, and most specifically a substituted or unsubstituted phenyl group, and all $R^{a1}$, $R^{a3}$ and $R^{a4}$ may be hydrogen.

For example, $R^{a2}$ of Chemical Formula 1 may be substituted at a meta position and Chemical Formula 1 may be represented by Chemical Formula 1-(1). Herein, when $R^{a2}$ is the substituent except hydrogen, phenylene substituted $R^{a2}$ may include kinked terphenyl structure.

[Chemical Formula 1-(1)]

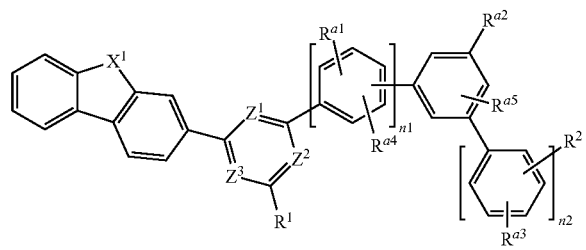

In Chemical Formula 1-(1), $Z^1$ to $Z^3$, $X^1$, $R^1$ and $R^2$, $R^{a1}$ to $R^{a5}$, n1, and n2 are the same as described above.

When the kinked terphenyl structure is included, a glass transition temperature (Tg) may be increased very effectively and a compound having a low molecular weight and a high glass transition temperature (Tg) may be designed and thereby thermal characteristics may be improved and stability may be ensured.

The glass transition temperature (Tg) may have a relation with thermal stability of a compound and a device including the same. That is, a compound for an organic optoelectronic device having a high glass transition temperature (Tg) is applied to an organic light emitting diode in a thin film form, in subsequent processes after depositing the compound for an organic optoelectronic device, for example in an encapsulation process, degradation by a temperature may be prevented and thus life-span characteristics of an organic compound and a device may be ensured.

On the other hand, in Chemical Formula 1, each linking group of

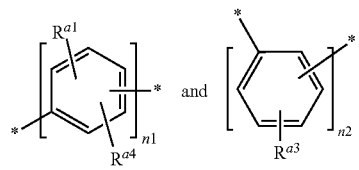

is linked at a meta or para position, and Chemical Formula 1 may be for example represented by one of Chemical Formula 1-(2), Chemical Formula 1-(3), Chemical Formula 1-(4), and Chemical Formula 1-(5).

[Chemical Formula 1-(2)]

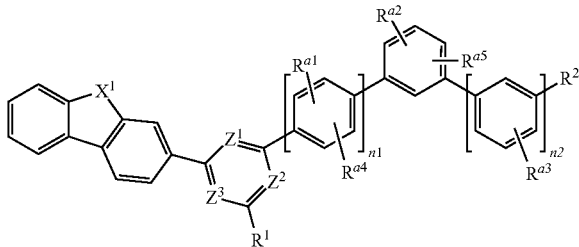

[Chemical Formula 1-(3)]

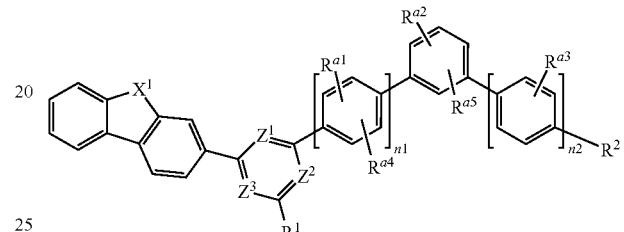

[Chemical Formula 1-(4)]

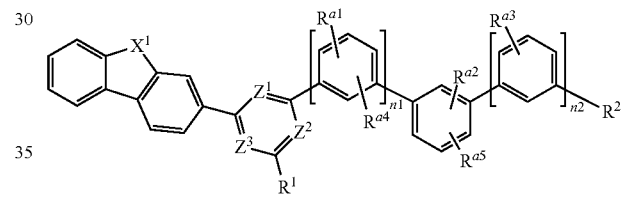

[Chemical Formula 1-(5)]

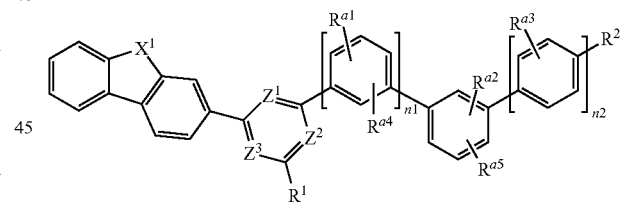

In Chemical Formula 1-(2), Chemical Formula 1-(3), Chemical Formula 1-(4), and Chemical Formula 1-(5), $X^1$, $R^1$ and $R^2$, $R^{a1}$ to $R^{a5}$, n1, and n2 are the same as described above.

In an example embodiment of the present invention, the n1 and n2 may independently be an integer of 0 or 1, for example all n1 and n2 may be 0; or at least one of n1 and n2 may be 1.

In an example embodiment of the present invention, when each of n1 and n2 is 0, it indicates a single bond.

For example, when the n1 is 0, Chemical Formula 1 may be represented by Chemical Formula 1-(6), when n2 is 0, Chemical Formula 1 may be represented by Chemical Formula 1-(7), and when the n1 and n2 are simultaneously 0, Chemical Formula 1 may be represented by Chemical Formula 1-(8).

[Chemical Formula 1-(6)]

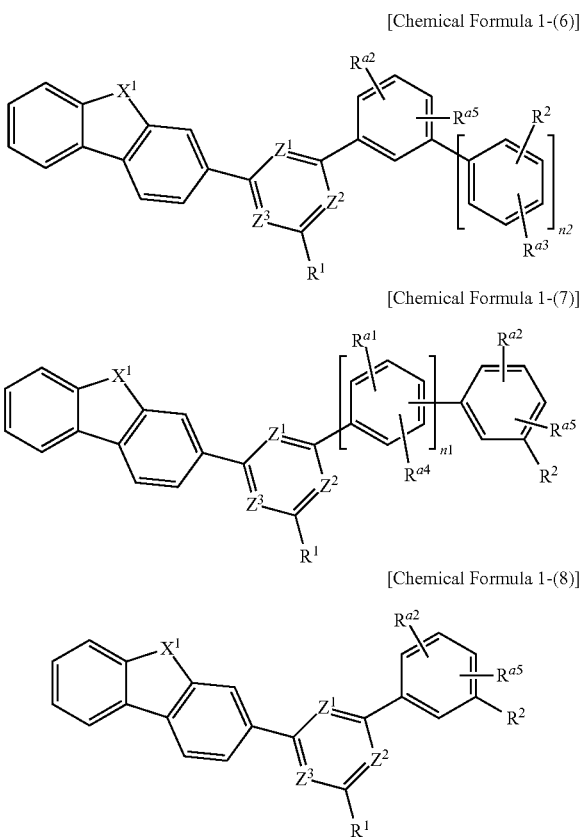

[Chemical Formula 1-(7)]

[Chemical Formula 1-(8)]

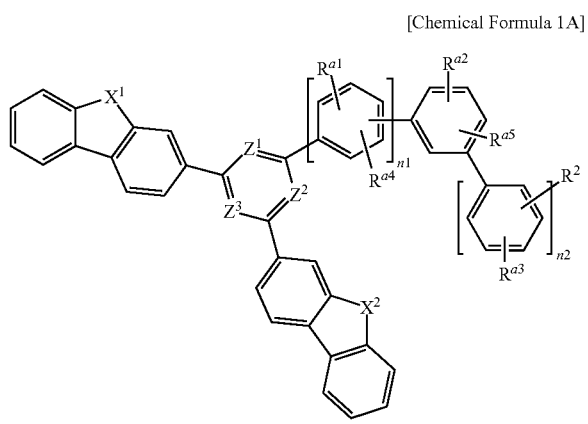

In Chemical Formulae 1-(6) to 1-(8), $Z^1$ to $Z^3$, $X^1$, $R^1$ and $R^2$, $R^{a1}$ to $R^{a5}$, n1, and n2 are the same as described above.

In an example embodiment of the present invention, when all n1 and n2 are 1, Chemical Formula 1 may be represented by Chemical Formula 1-(3), Chemical Formula 1-(4), or Chemical Formula 1-(5).

In a specific example embodiment of the present invention, the $R^1$ is a substituted or unsubstituted dibenzofuranyl group, or a substituted or unsubstituted dibenzothiophenyl group and the $R^2$ is a substituted or unsubstituted C6 to C20 aryl group, wherein Chemical Formula 1 may be for example represented by Chemical Formula 1A.

[Chemical Formula 1A]

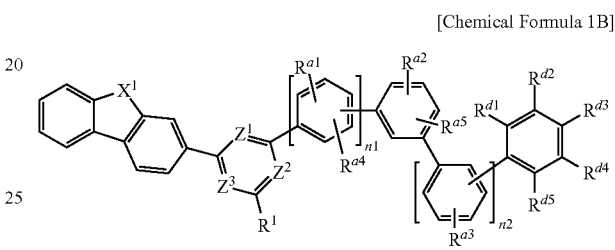

In Chemical Formula 1A, $Z^1$ to $Z^3$, $X^1$ and $X^2$, $R^2$, $R^{a1}$ to $R^{a5}$, n1, and n2 are the same as described above.

$R^2$ of Chemical Formula 1A may be a substituted or unsubstituted phenyl group, a substituted or unsubstituted biphenyl group, a substituted or unsubstituted terphenyl group, a substituted or unsubstituted naphthyl group, or a substituted or unsubstituted fluorenyl group, and more specifically, a substituted or unsubstituted phenyl group, a substituted or unsubstituted biphenyl group, or a substituted or unsubstituted terphenyl group.

In another example embodiment of the present invention, the $R^1$ may be a substituted or unsubstituted C6 to C20 aryl group and the $R^2$ may be a substituted or unsubstituted C6 to C20 aryl group, a substituted or unsubstituted dibenzofuranyl group, or a substituted or unsubstituted dibenzothiophenyl group, wherein Chemical Formula 1 may be for example represented by Chemical Formula 1B.

[Chemical Formula 1B]

In Chemical Formula 1B, $Z^1$ to $Z^3$, $X^1$, $R^1$, $R^{a1}$ to $R^{a5}$, n1, and n2 are the same as above, $R^{d1}$ to $R^{d5}$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C20 heterocyclic group, or a combination thereof, and $R^{d1}$ to $R^{d5}$ are independently present or adjacent groups thereof are linked with each other to form a substituted or unsubstituted aliphatic, aromatic, or heteroaromatic monocyclic or polycyclic ring.

Specifically the $R^1$ may be a substituted or unsubstituted phenyl group, a substituted or unsubstituted biphenyl group, a substituted or unsubstituted naphthyl group, a substituted or unsubstituted terphenyl group, or a substituted or unsubstituted fluorenyl group, and more specifically, a substituted or unsubstituted phenyl group, a substituted or unsubstituted biphenyl group, or a substituted or unsubstituted terphenyl group, and the $R^{d1}$ to $R^{d5}$ are independently a substituted or unsubstituted phenyl group, a substituted or unsubstituted biphenyl group, a substituted or unsubstituted terphenyl group, a substituted or unsubstituted dibenzofuranyl group, or a substituted or unsubstituted dibenzothiophenyl group; or adjacent groups of $R^{d1}$ to $R^{d5}$ are linked with each other to form a substituted or unsubstituted aliphatic, aromatic or heteroaromatic polycyclic ring.

The "linking of the adjacent groups" refers to the phenyl group linked with $R^{d1}$ to $R^{d5}$ and two adjacent substituents of $R^{d1}$ to $R^{d5}$ are fused with each other to provide a substituted or unsubstituted aliphatic, aromatic, or heteroaromatic monocyclic or polycyclic ring. For example, each of $R^{d1}$ and $R^{d2}$, $R^{d2}$ and $R^{d3}$, $R^{d3}$ and $R^{d4}$, and $R^{d4}$ and $R^{d5}$ are linked with each other to form a heteroaromatic polycyclic ring with the phenyl group. Herein, examples of the formed heteroaromatic polycyclic ring may be a substituted or unsubstituted dibenzofuranyl group, a substituted or unsubstituted dibenzothiophenyl group, and the like, for example adjacent groups of the $R^{d1}$ to $R^{d5}$ are linked with each other and linked with the phenyl group may form a heteroaromatic polycyclic ring represented by Chemical Formula A.

For example, a heteroaromatic polycyclic ring represented by Chemical Formula A may be formed.

[Chemical Formula A]

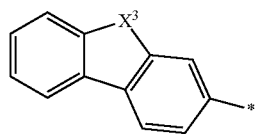

In Chemical Formula A, $X^3$ is O or S and * is a point linked with adjacent substituted or unsubstituted phenylene.

Specific examples of heteroaromatic polycyclic rings where adjacent groups of the $R^{d1}$ to $R^{d5}$ are linked with each other may be "Compound B-10" of specific compounds of the present invention which will be described later.

In another specific example embodiment of the present invention, the $R^1$ may be a substituted or unsubstituted C6 to C20 aryl group and the $R^2$ may be a substituted or unsubstituted C2 to C20 heteroaryl group and, wherein Chemical Formula 1 may be for example represented by Chemical Formula 1C.

[Chemical Formula 1C]

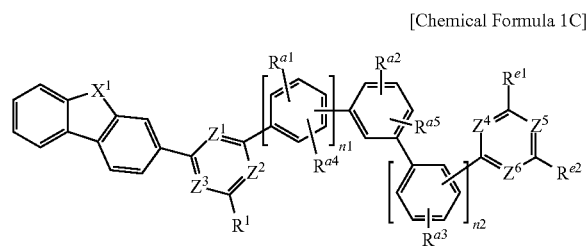

In Chemical Formula 1C, $Z^1$ to $Z^3$, $X^1$, $R^1$, $R^{a1}$ to $R^{a5}$, n1, and n2 are the same as above, $Z^4$ to $Z^6$ are independently N or $CR^e$, at least two of $Z^4$ to $Z^6$ are N, and $R^e$, $R^{e1}$, and $R^{e2}$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C30 heterocyclic group, or a combination thereof, and the $R^e$, $R^{e1}$, and $R^{e2}$ are independently present or adjacent groups thereof are linked with each other to form a monocyclic or polycyclic ring.

In one example of the present invention, the $R^e$, $R^{e1}$, and $R^{e2}$ may independently be hydrogen, deuterium, a cyano group, a nitro group, a substituted or unsubstituted C1 to C4 alkyl group, or a substituted or unsubstituted C6 to C18 aryl group. In more specific example, the $R^e$, $R^{e1}$, and $R^{e2}$ may be a phenyl group, a biphenyl group, a naphthyl group, a terphenyl group, or a triphenylene group.

Specifically the $R^1$ may be a substituted or unsubstituted phenyl group, a substituted or unsubstituted biphenyl group, a substituted or unsubstituted naphthyl group, a substituted or unsubstituted terphenyl group, or a substituted or unsubstituted fluorenyl group, and specifically, a substituted or unsubstituted phenyl group, a substituted or unsubstituted biphenyl group, or a substituted or unsubstituted terphenyl group, and a hexagonal ring consisting of the $Z^4$ to $Z^6$ may be a substituted or unsubstituted pyrimidine or a substituted or unsubstituted triazine where each of $R^e$, $R^{e1}$, and $R^{e2}$ are independently substituted or adjacent groups of $R^e$, $R^{e1}$, and $R^{e2}$ are linked with other to form a substituted or unsubstituted quinolinyl group, a substituted or unsubstituted isoquinolinyl group, a substituted or unsubstituted quinazolinyl group, or a substituted or unsubstituted quinoxalinyl group.

More specifically, the hexagonal ring consisting of the $Z^4$ to $Z^6$ may be a substituted or unsubstituted pyrimidine or a substituted or unsubstituted triazine, and the $R^{e1}$ and $R^{e2}$ are independently a substituted or unsubstituted C6 to C30 aryl group, and more specifically a substituted or unsubstituted phenyl group, a substituted or unsubstituted biphenyl group, or a substituted or unsubstituted terphenyl group.

The compound for an organic optoelectronic device represented by Chemical Formula 1 may be for example selected from compounds of Group 1, but is not limited thereto.

[Group 1]

[A-1]

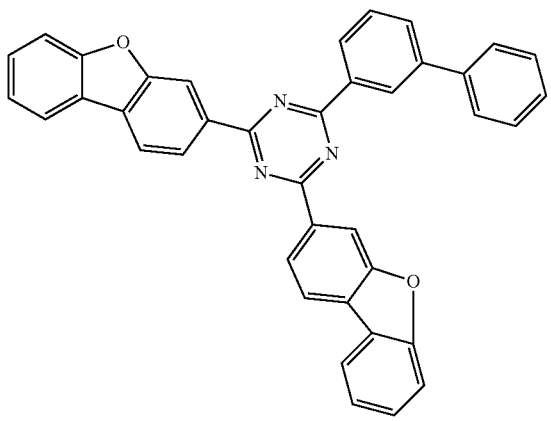

[A-2]

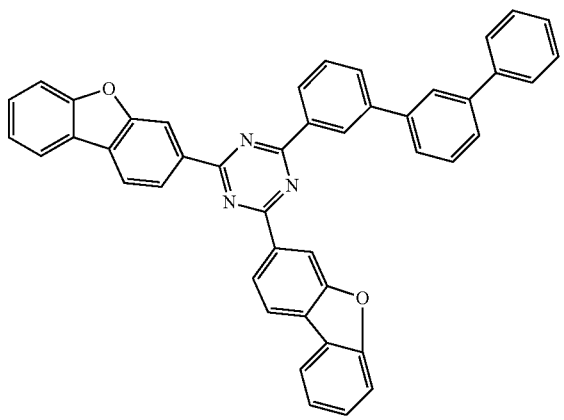

-continued
[A-3]
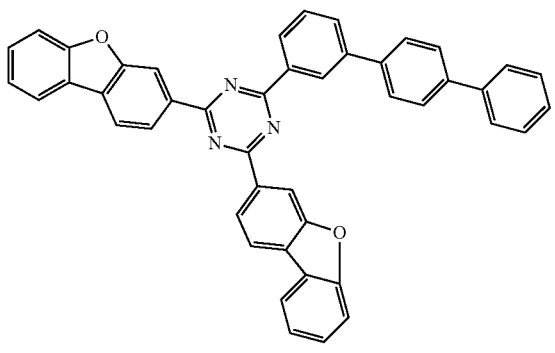
[A-4]
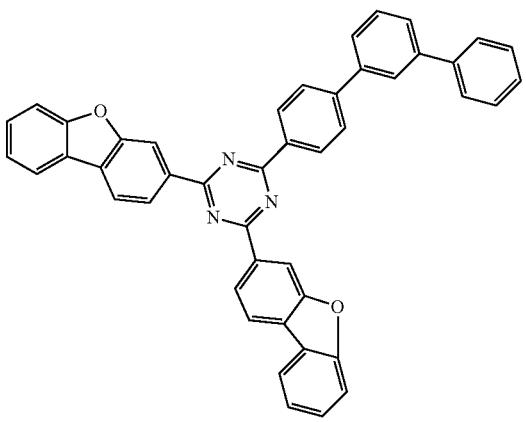
[A-5]
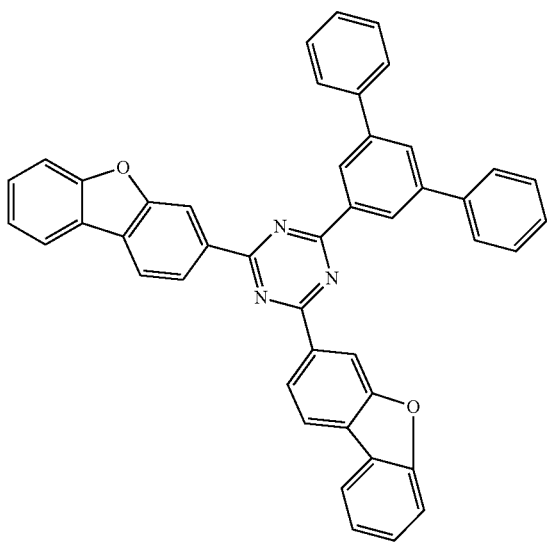
[A-6]
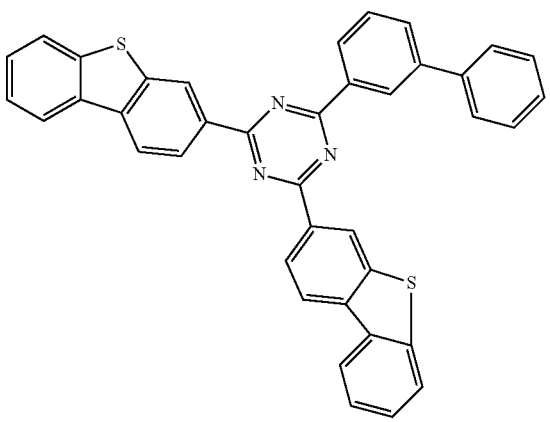
[A-7]
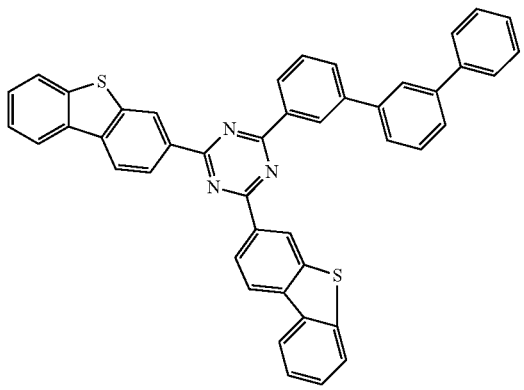
[A-8]
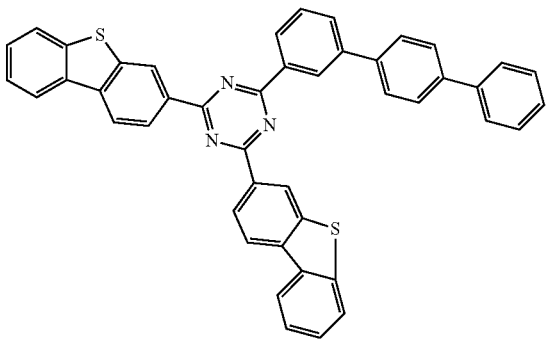

-continued
[A-9]
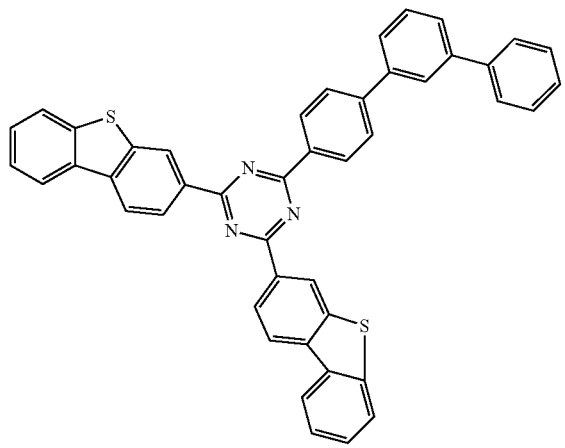
[A-10]
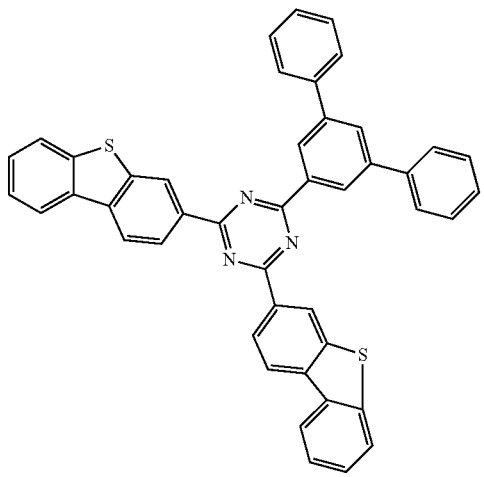
[A-11]
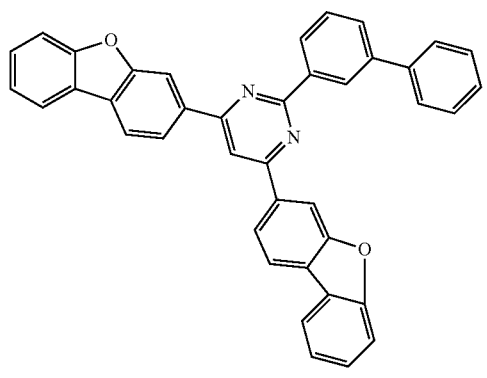
[A-12]
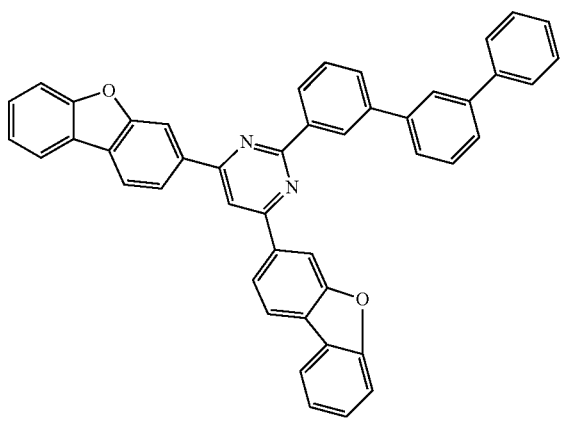
[A-13]
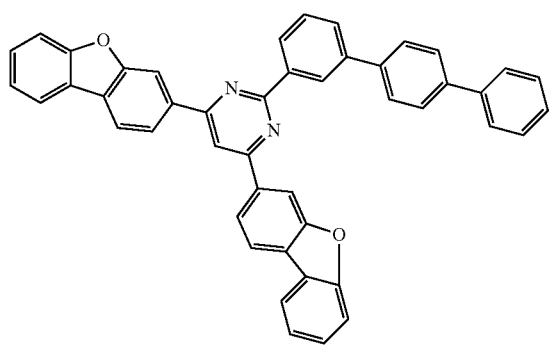
[A-14]
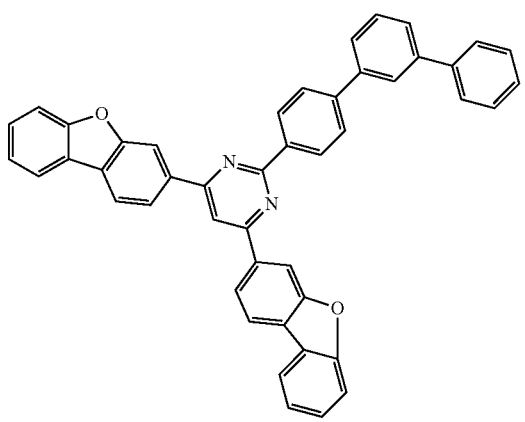

-continued
[A-15]
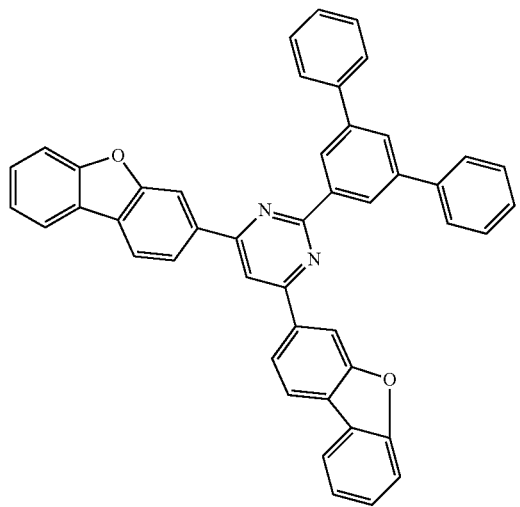
[A-16]
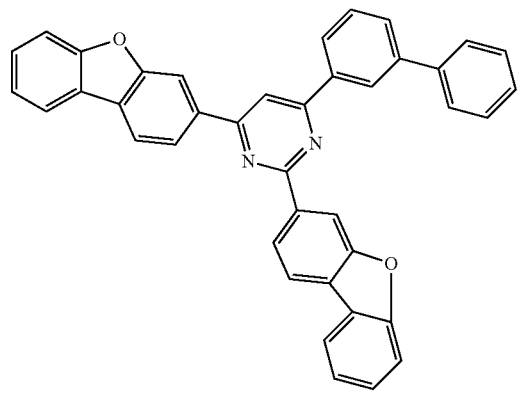
[A-17]
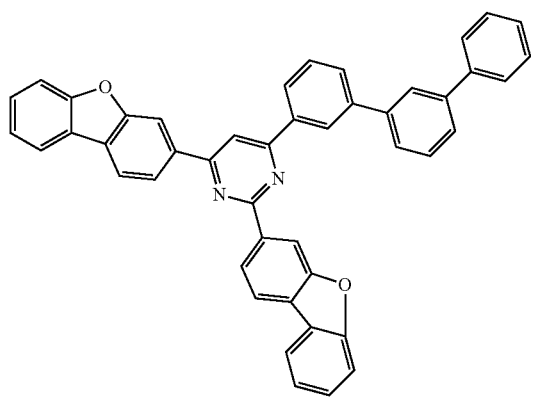
[A-18]
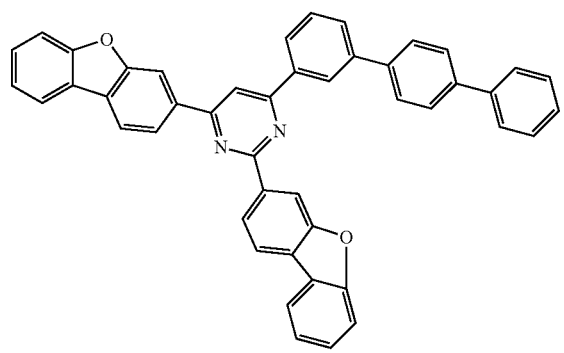
[A-19]
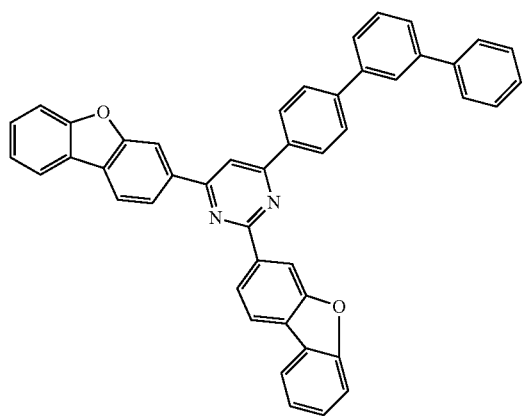
[A-20]
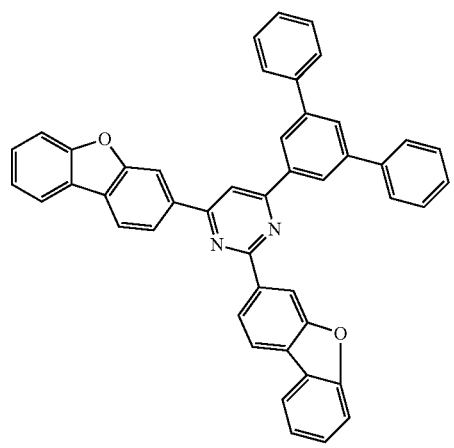

-continued
[A-21]
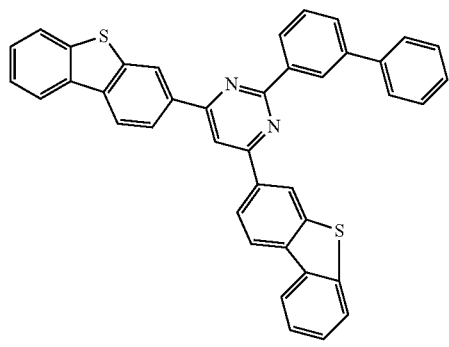
[A-22]
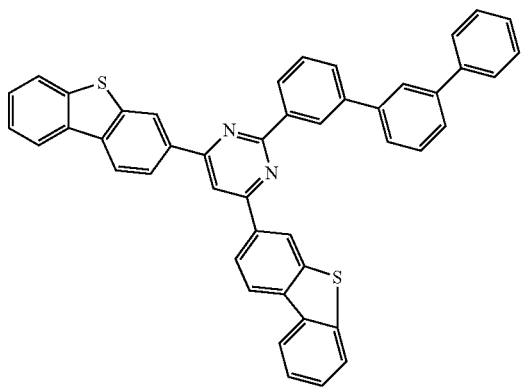
[A-23]
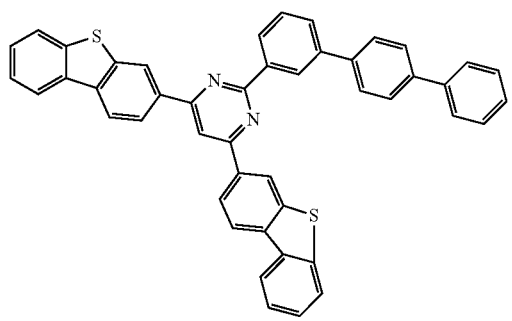
[A-24]
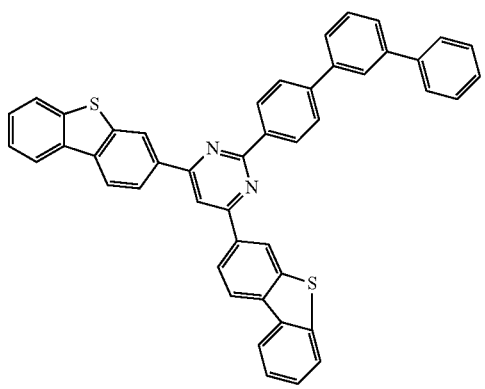
[A-25]
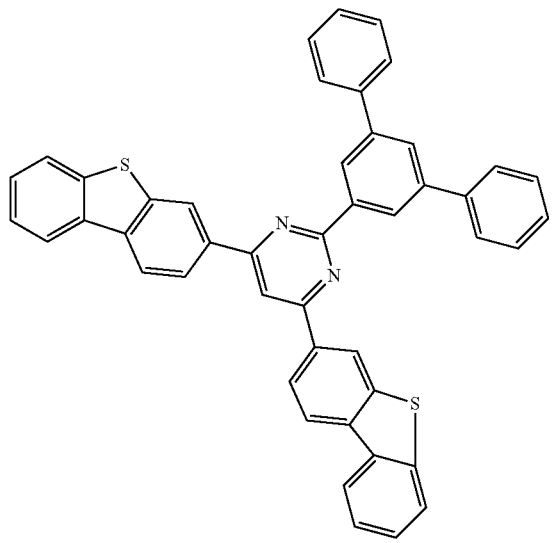
[A-26]
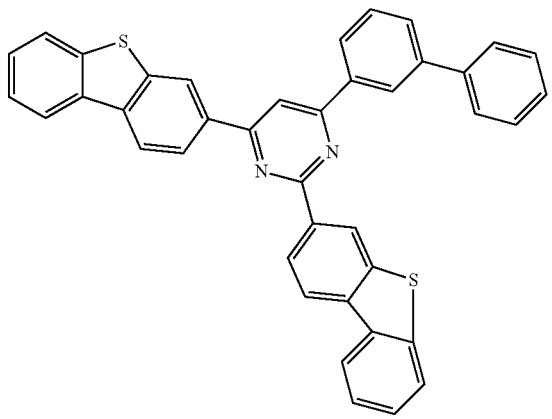

-continued
[A-27]
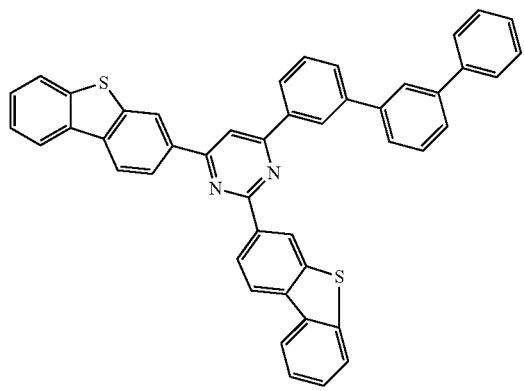
[A-28]
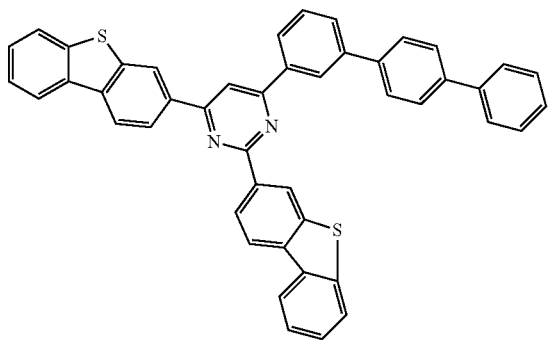
[A-29]
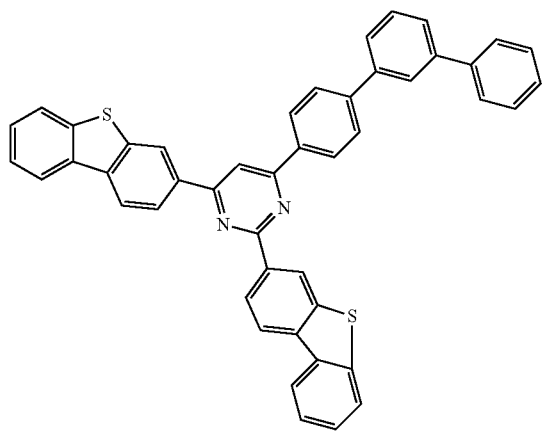
[A-30]
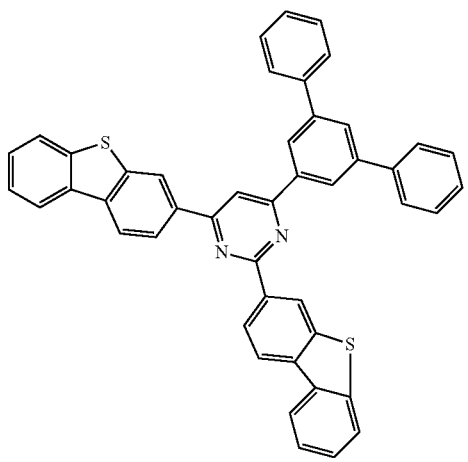
[B-1]
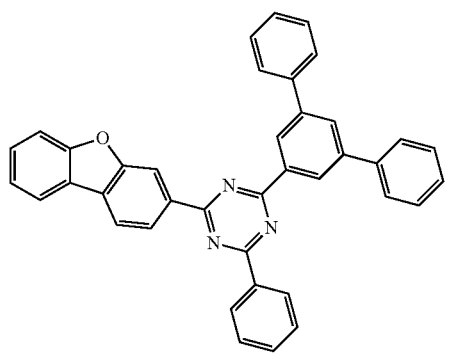
[B-2]
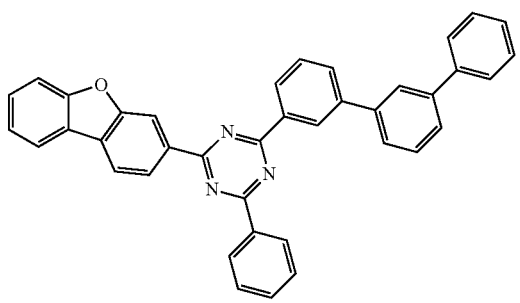
[B-3]
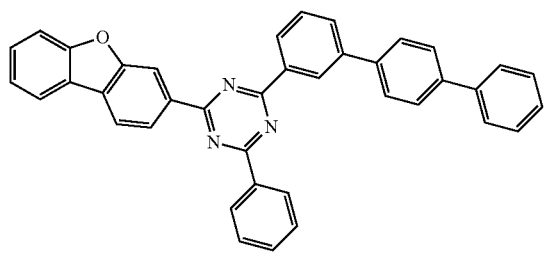
[B-4]
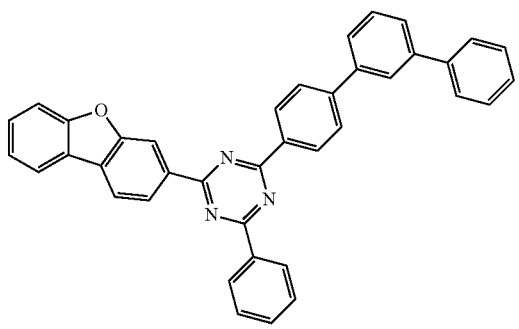

-continued
[B-5]
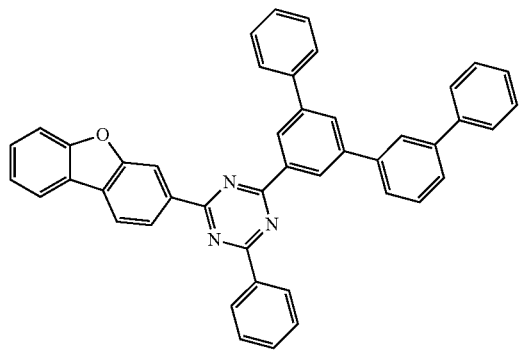
[B-6]
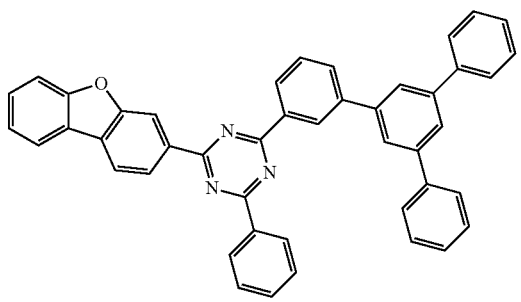
[B-7]
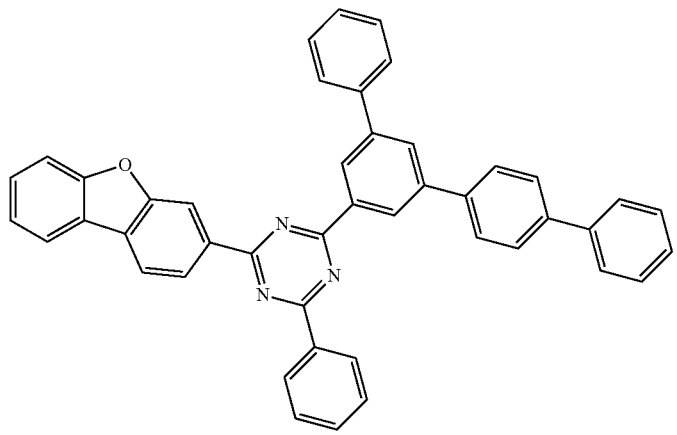
[B-8]
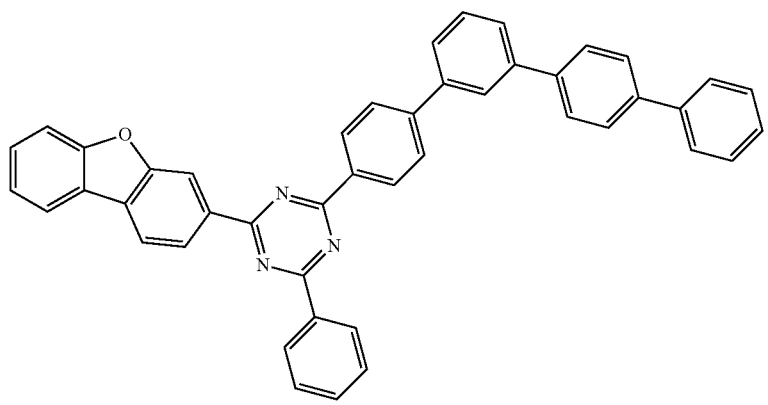

-continued
[B-9]
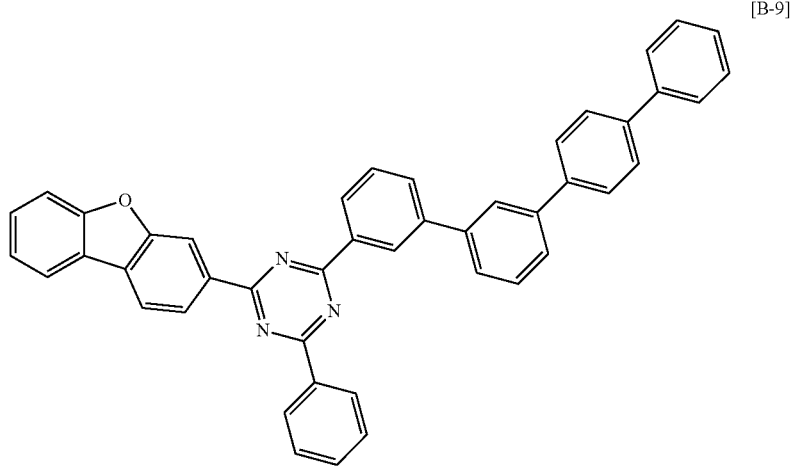
[B-10]
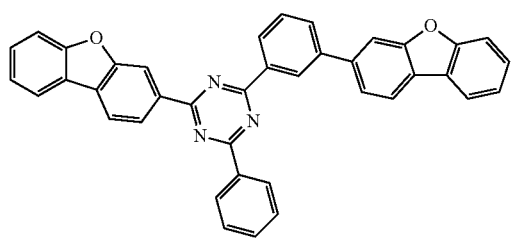
[B-11]
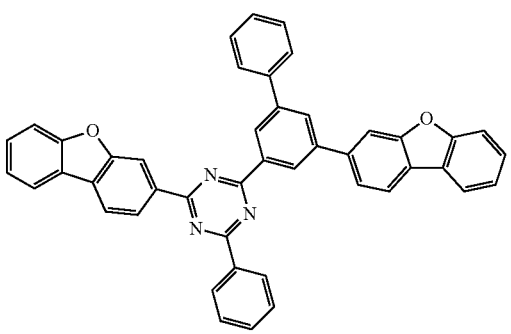
[B-12]
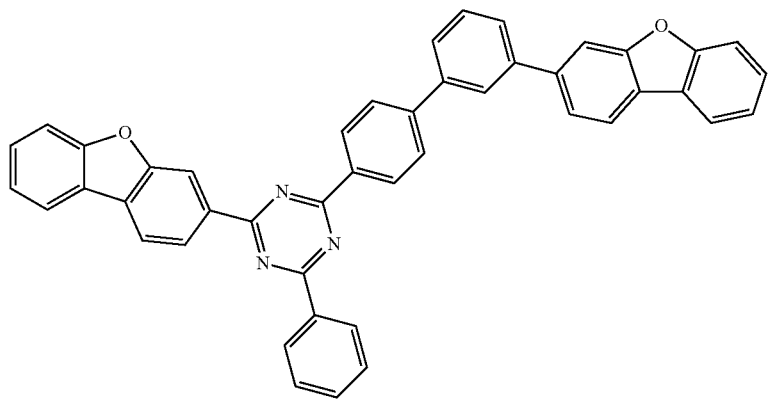
[B-13]
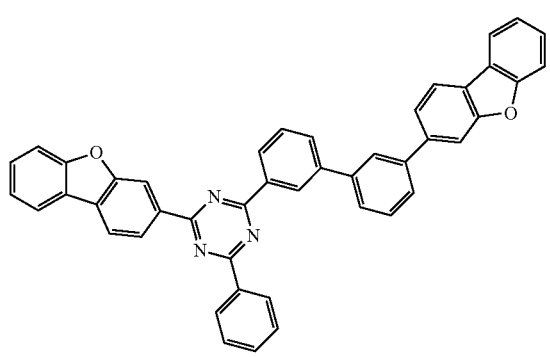
[B-14]
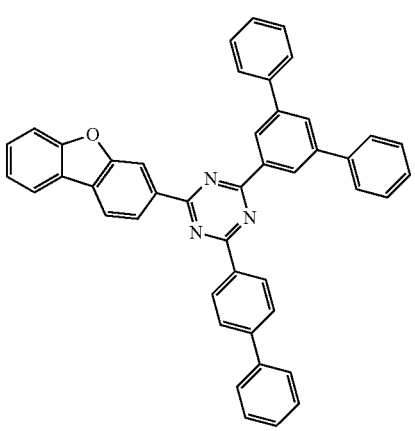

-continued
[B-15]
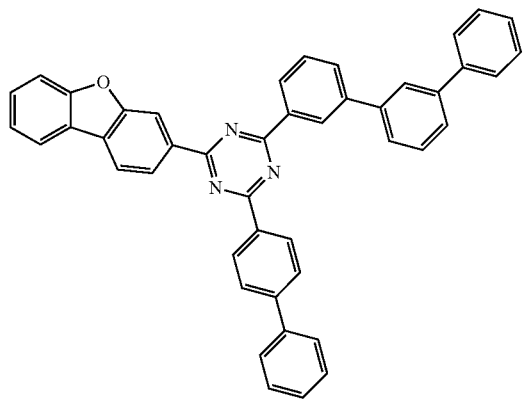
[B-16]
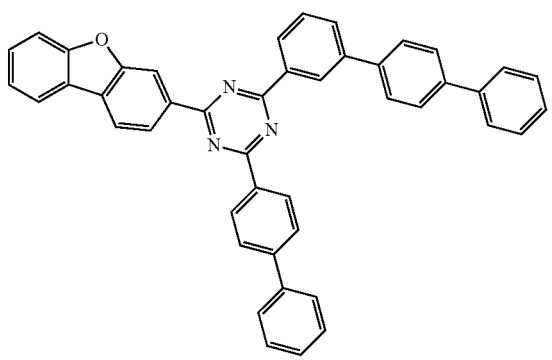
[B-17]
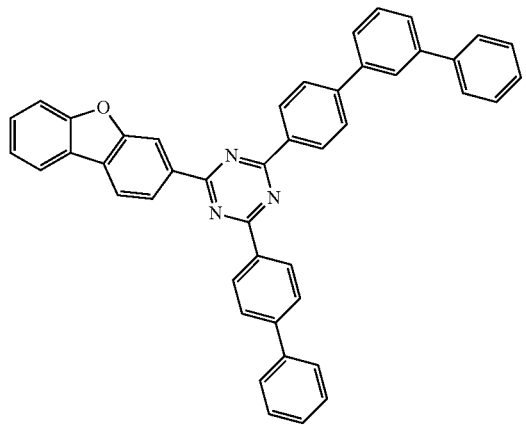
[B-18]
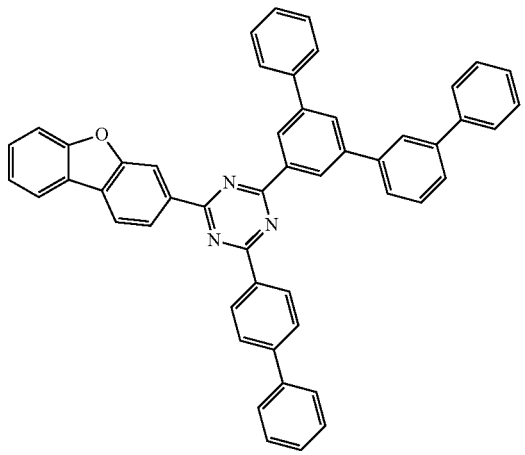
[B-19]
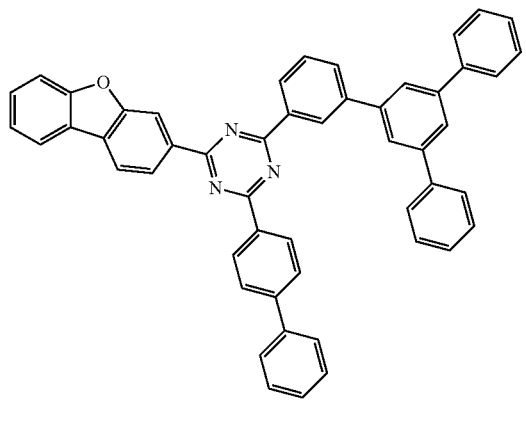
[B-20]
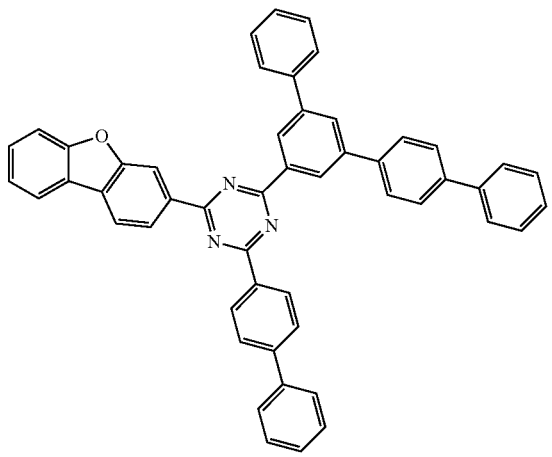

[B-21]
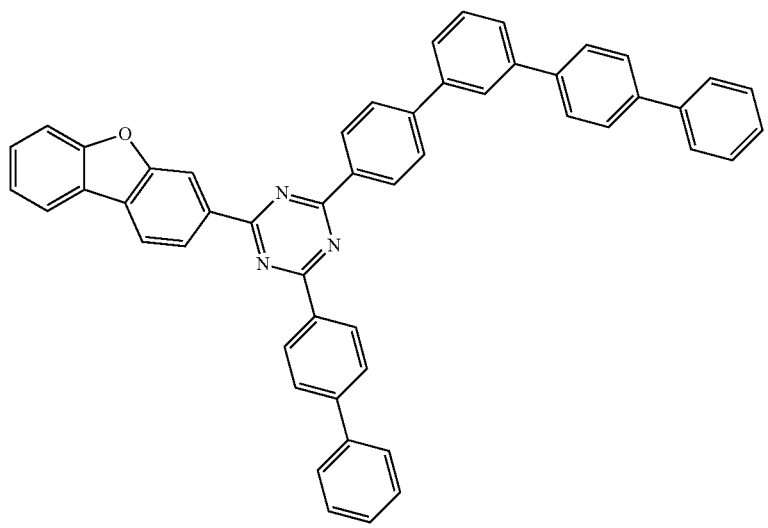
[B-22]     [B-23]
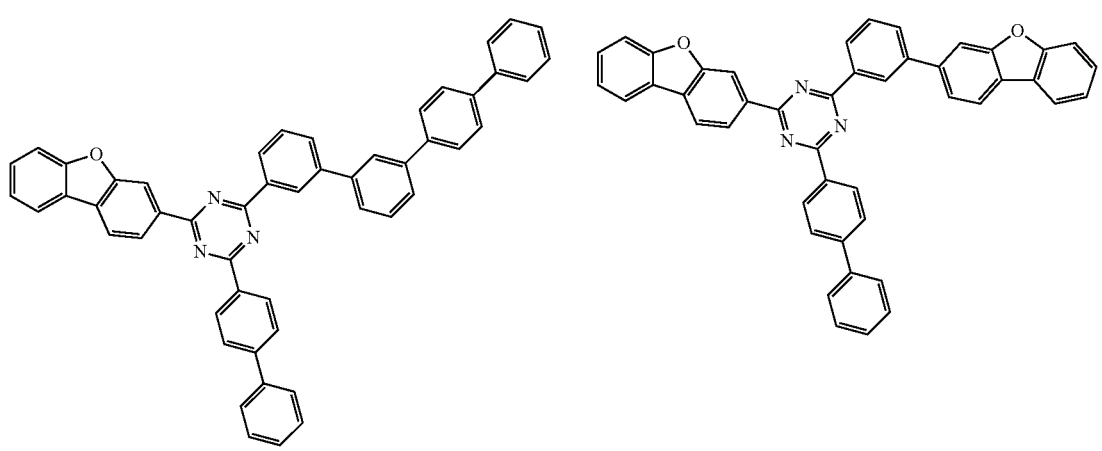
[B-24]
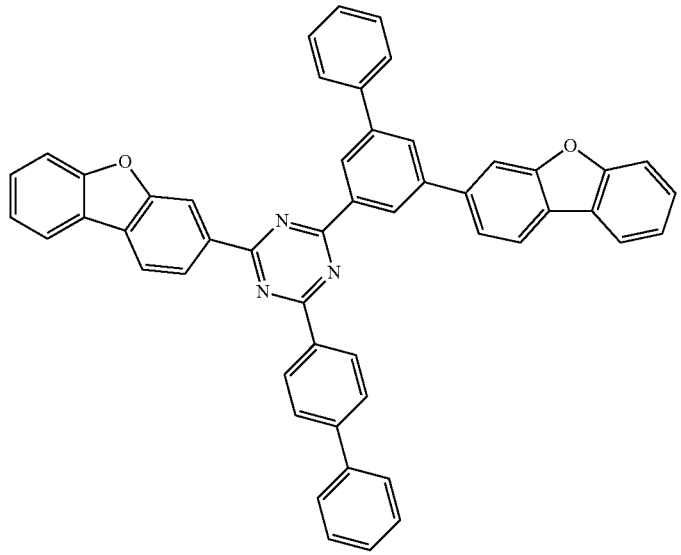

[B-25]
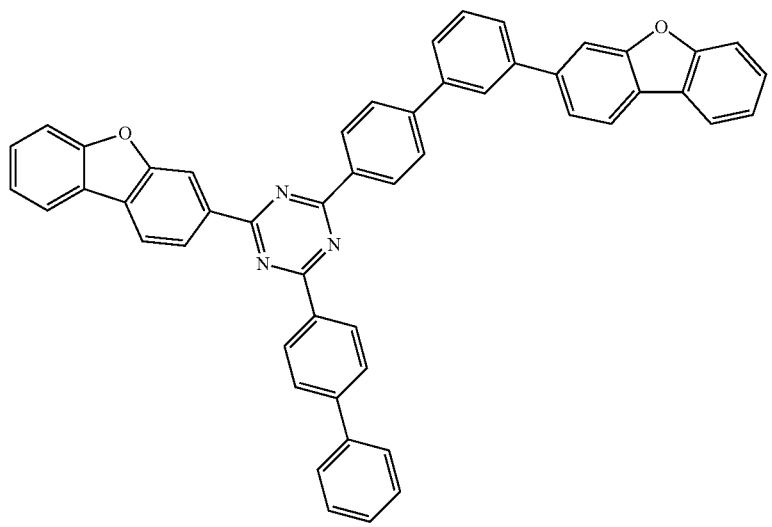
[B-26]
[B-27]
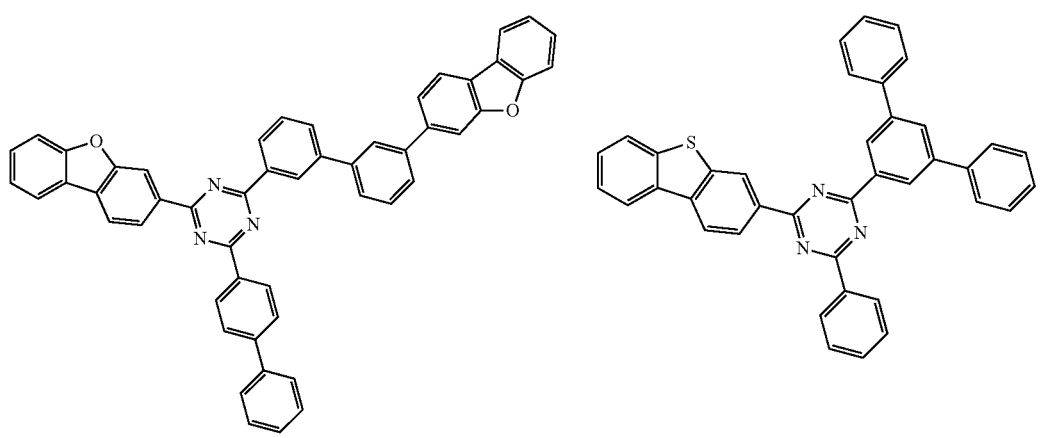
[B-28]
[B-29]
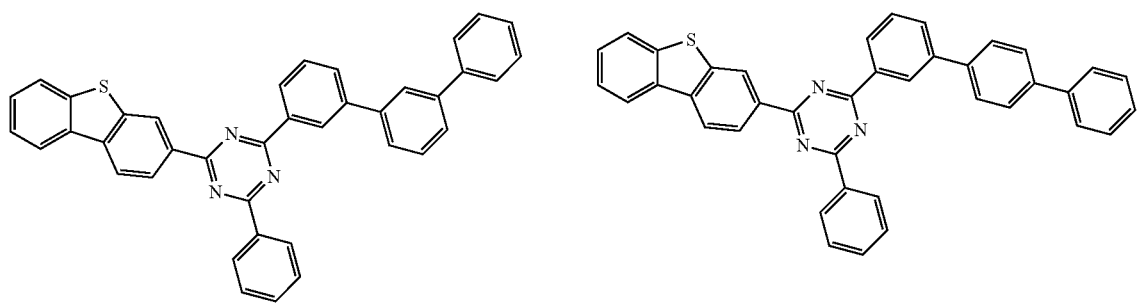

-continued
[B-30] 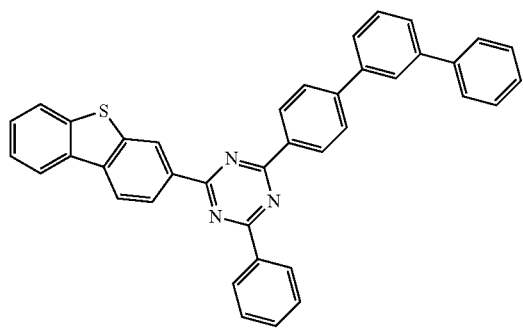
[B-31] 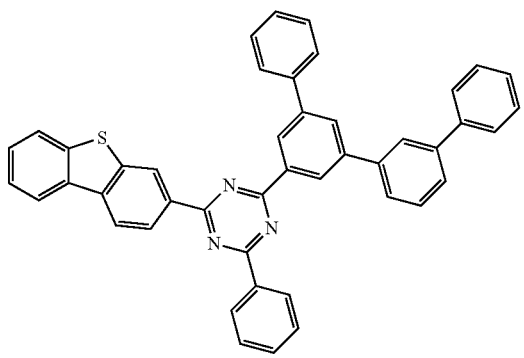
[B-32] 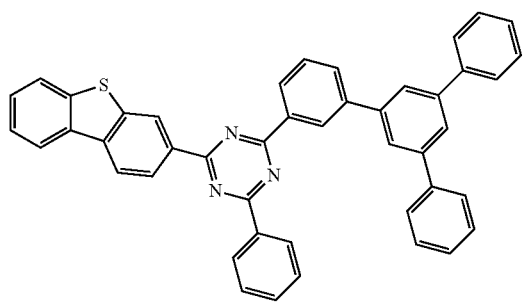
[B-33] 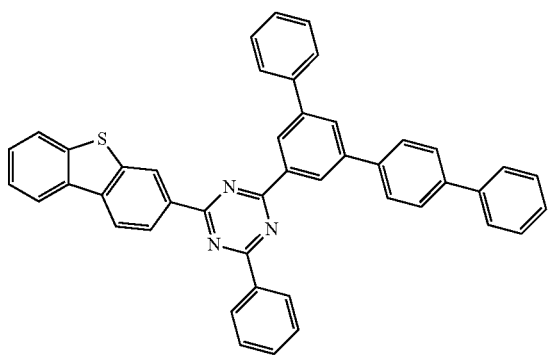
[B-34] 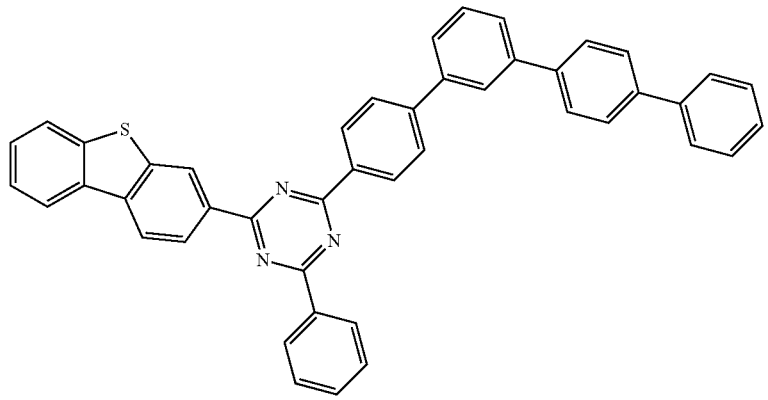
[B-35] 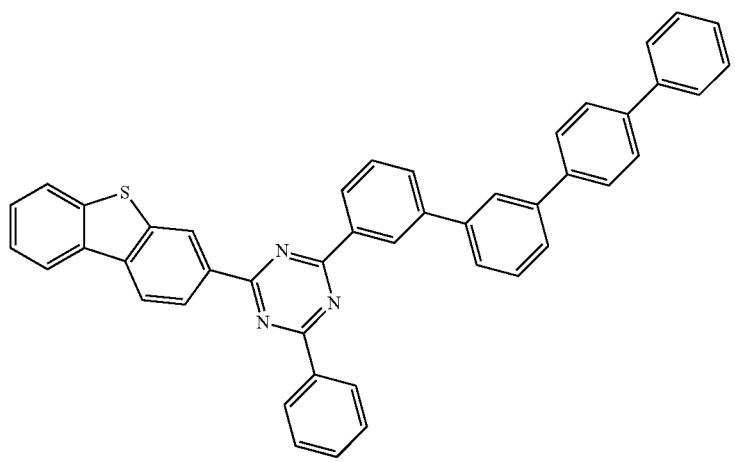

-continued
[B-36]
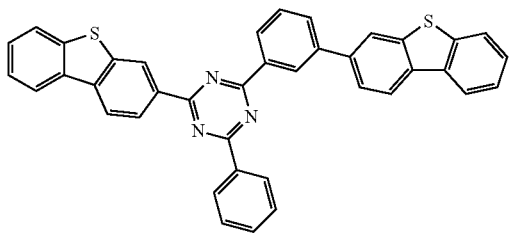
[B-37]
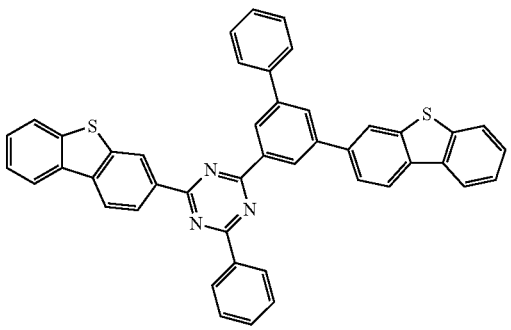
[B-38]
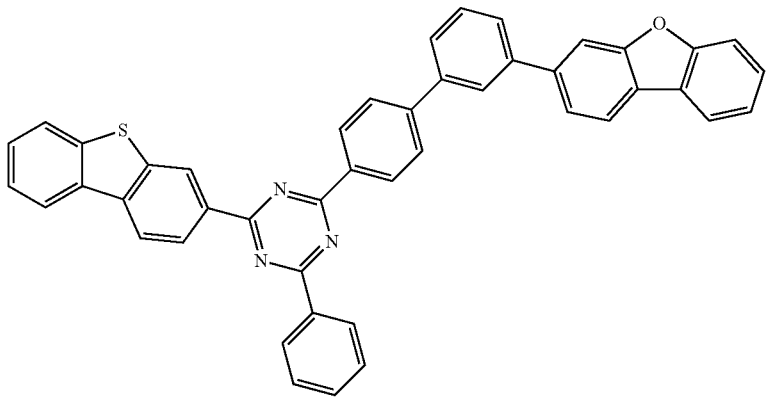
[B-39]
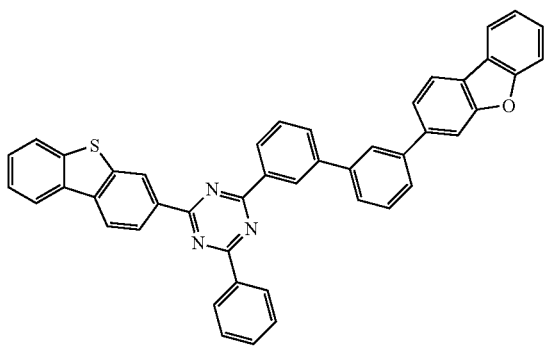
[B-40]
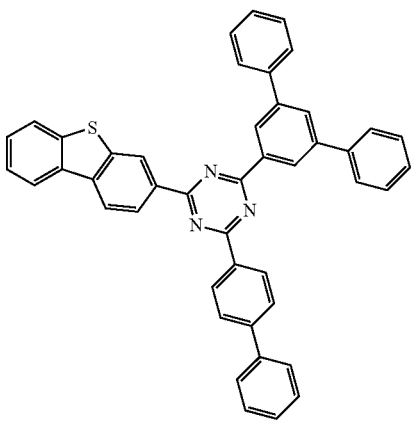
[B-41]
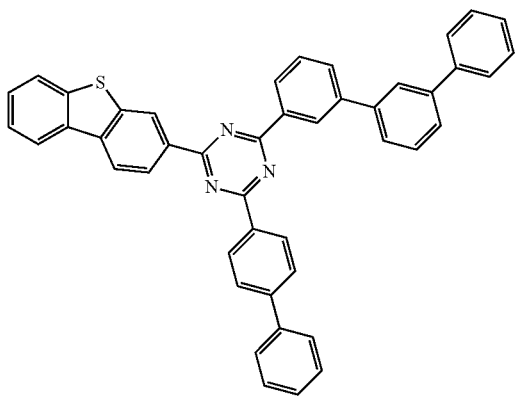
[B-42]
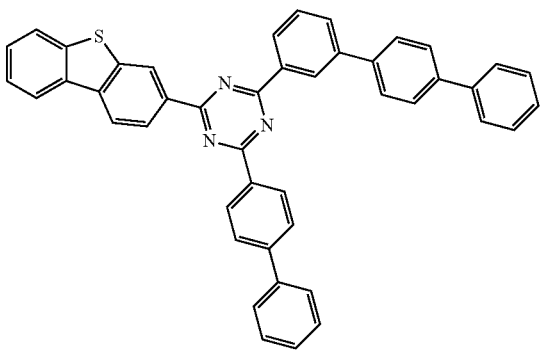

-continued
[B-43] [B-44]
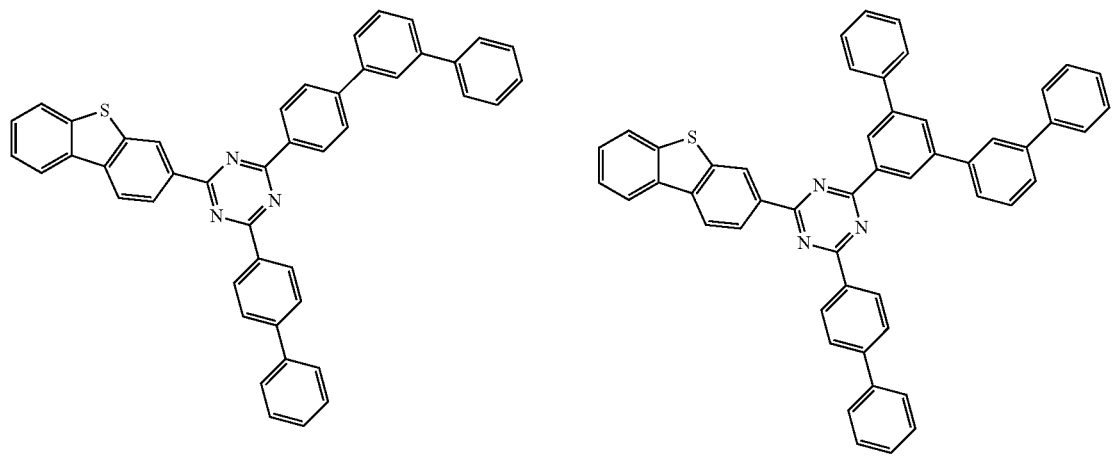
[B-45] [B-46]
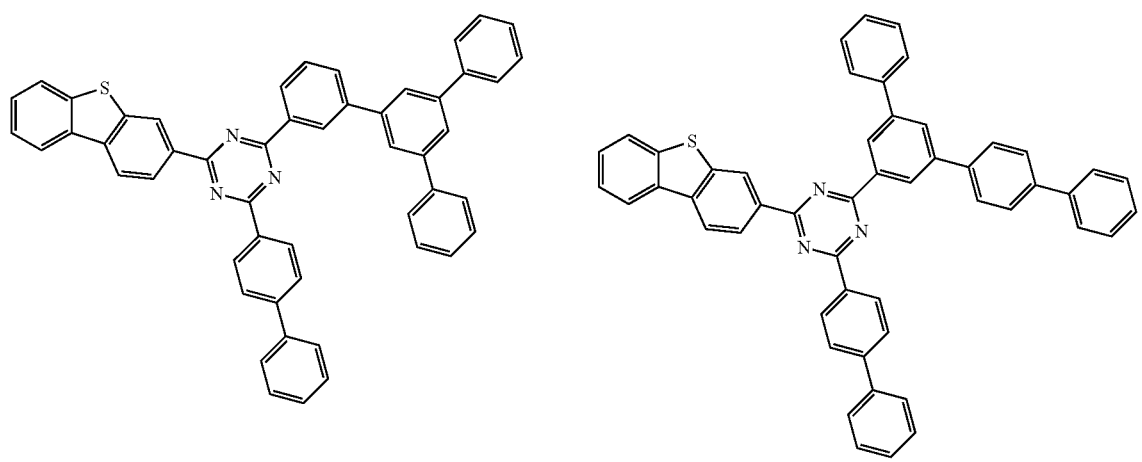
[B-47]
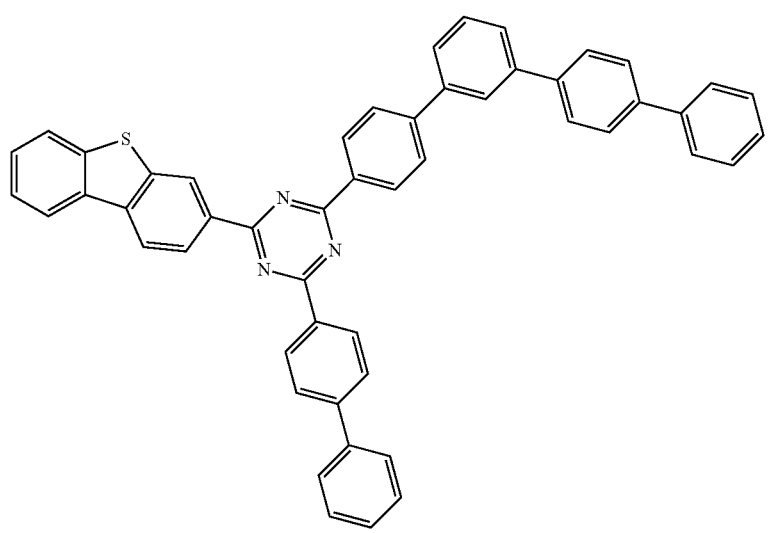

[B-48]
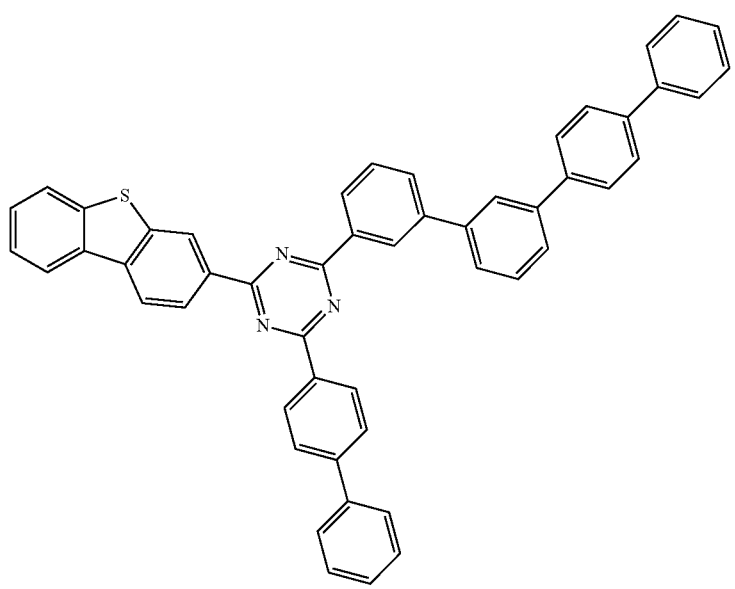
[B-49]
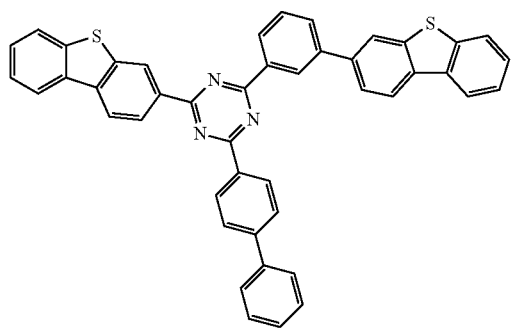
[B-50]
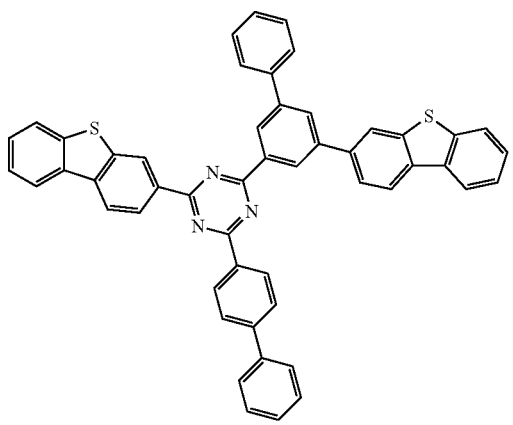
[B-51]
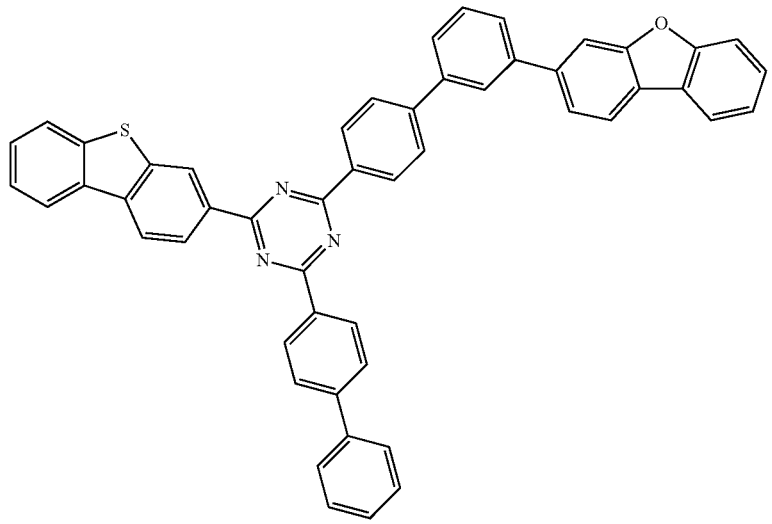

-continued
[B-52]
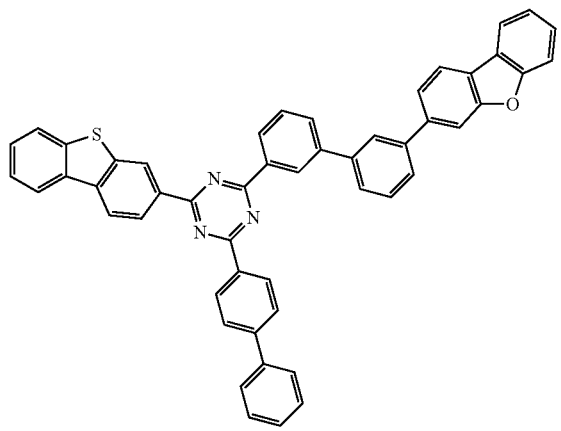
[B-53]
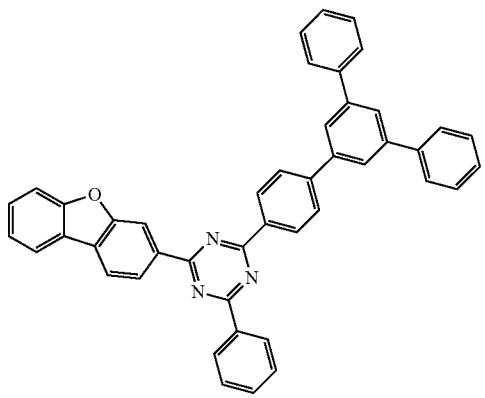
[B-54]
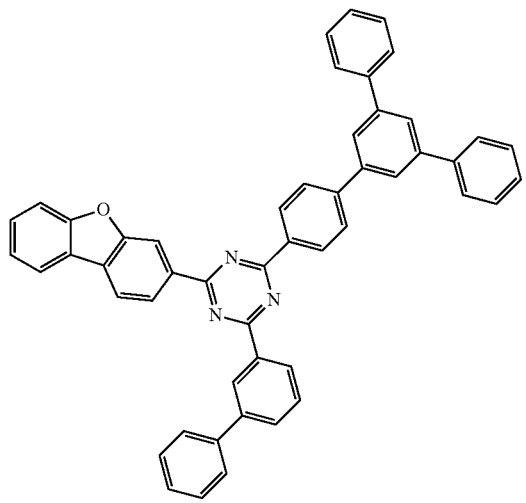
[B-55]
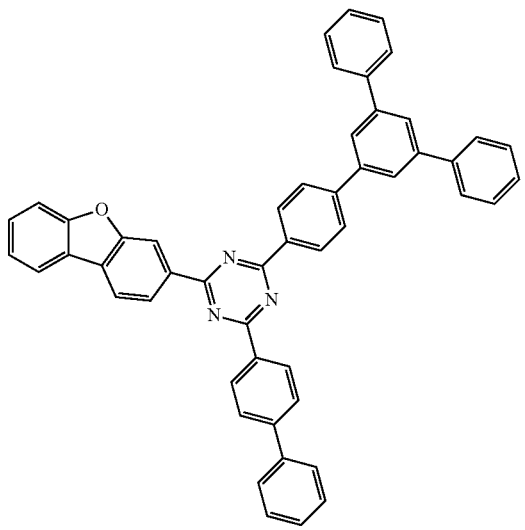
[B-56]
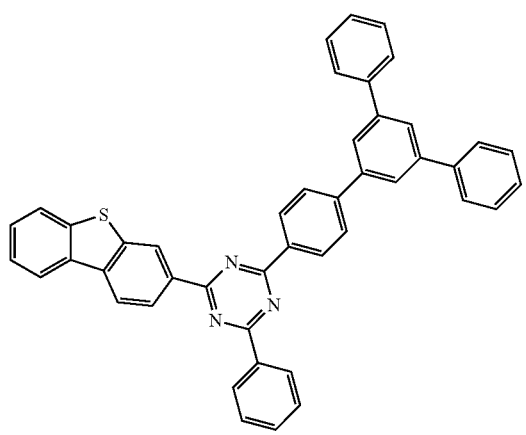
[B-57]
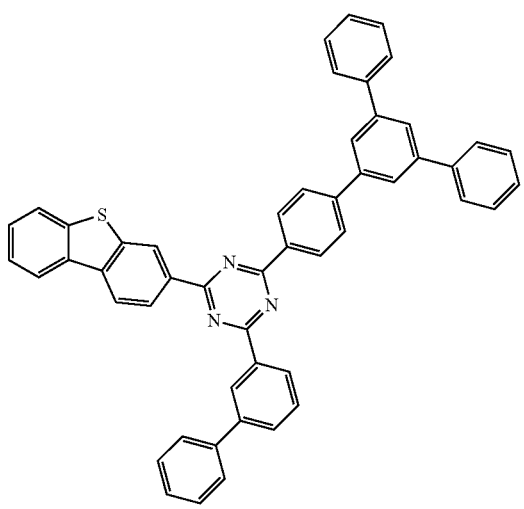

-continued
[B-58]
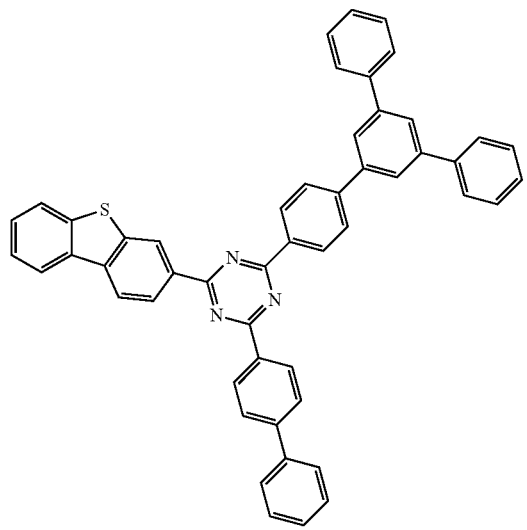
[B-59]
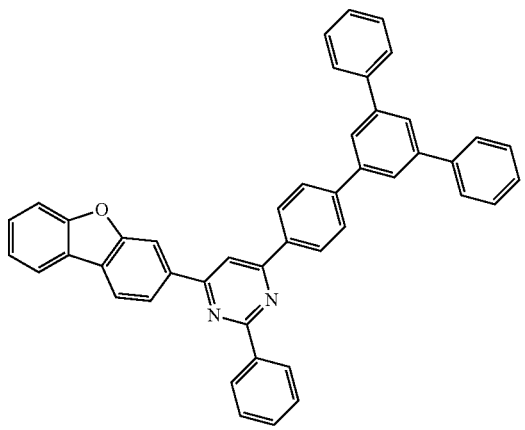
[B-60]
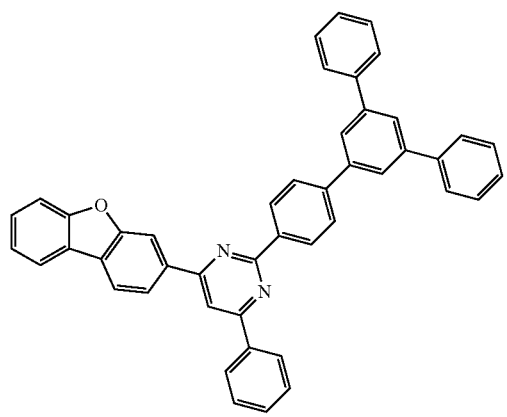
[B-61]
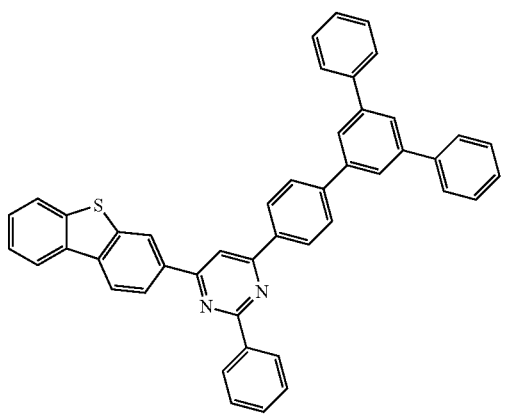
[B-62]
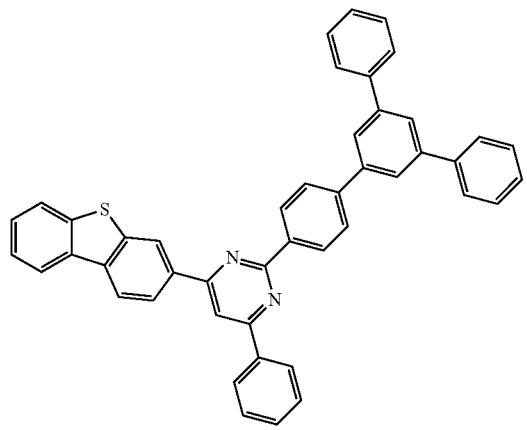
[B-63]
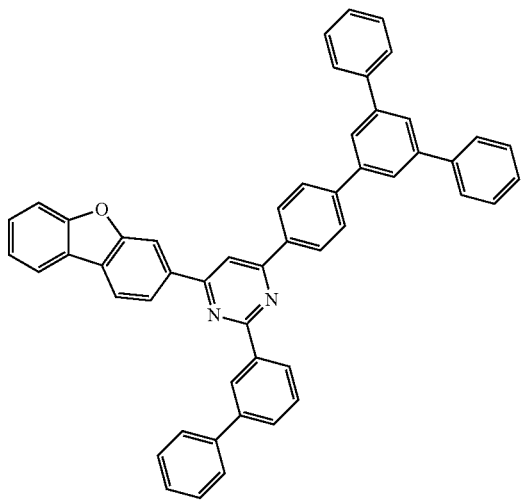

-continued
[B-64]
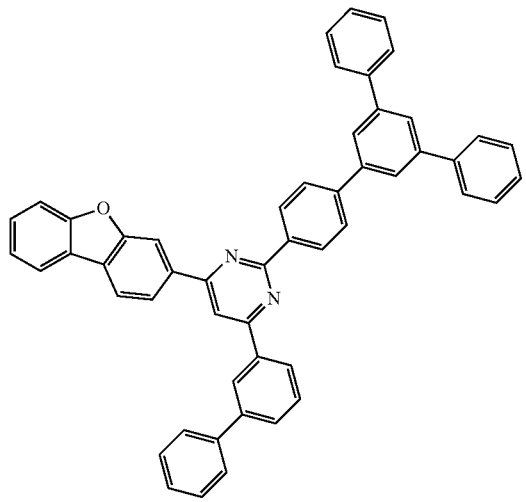
[B-65]
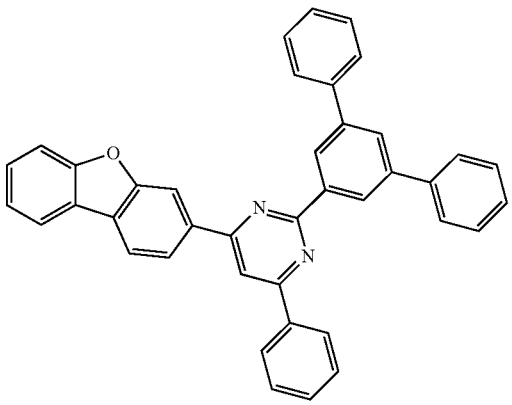
[B-66]
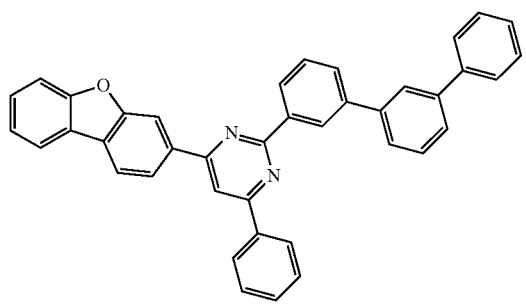
[B-67]
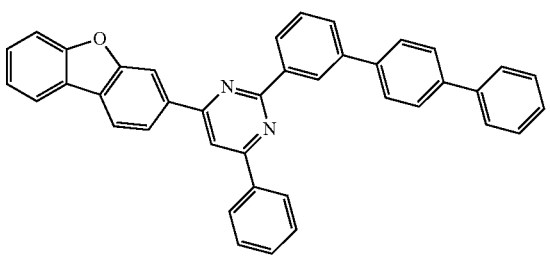
[B-68]
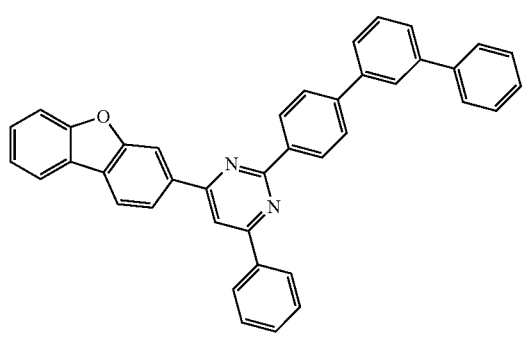
[B-69]
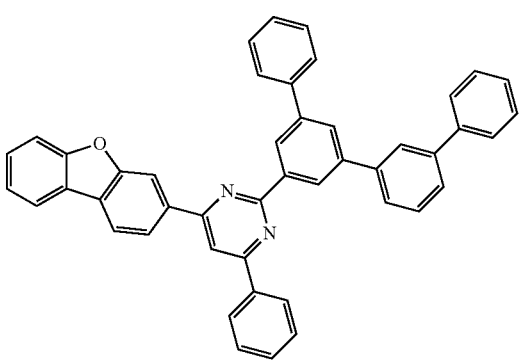

-continued
[B-70]
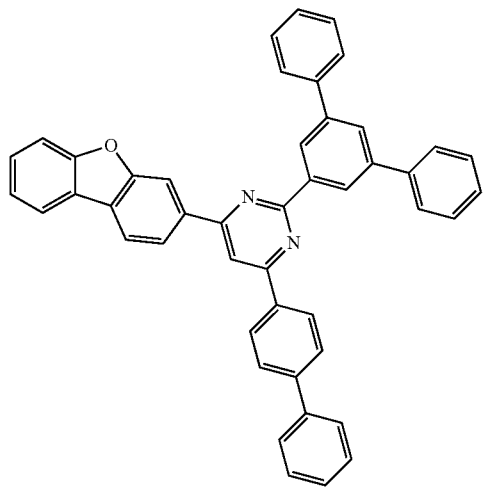
[B-71]
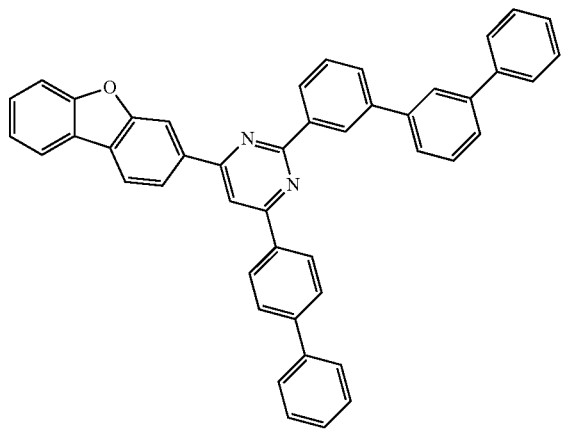
[B-72]
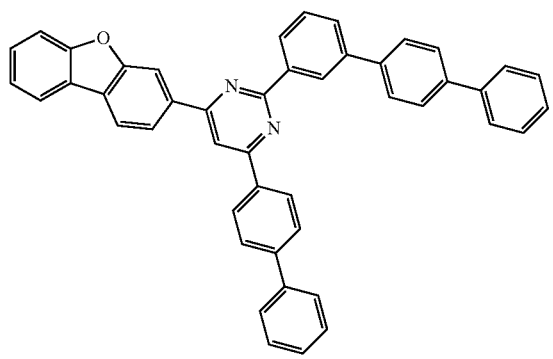
[B-73]
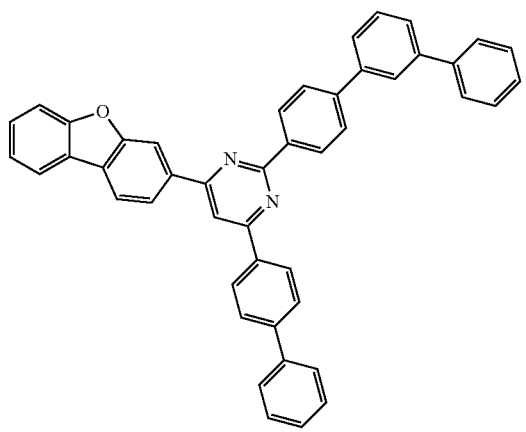
[B-74]
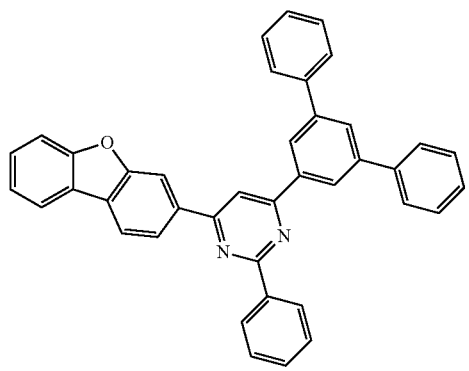
[B-75]
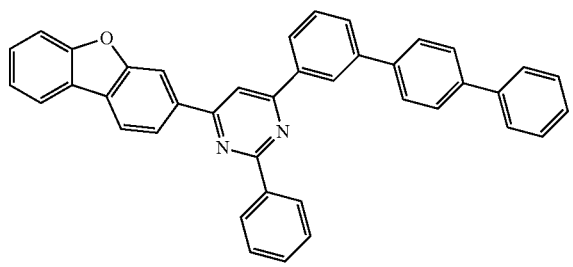

-continued
[B-76]
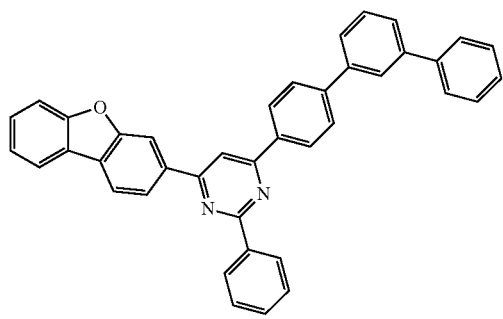
[B-77]
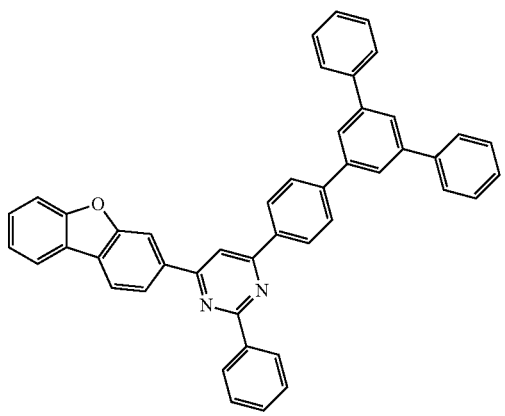
[B-78]
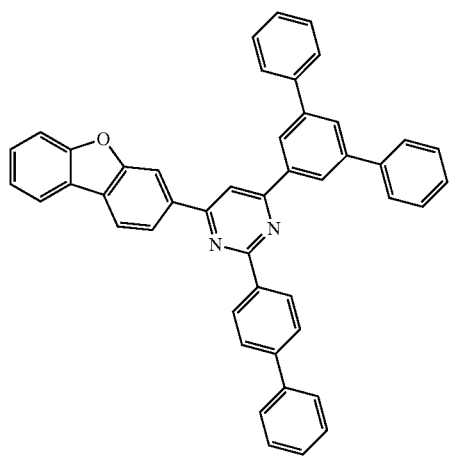
[B-79]
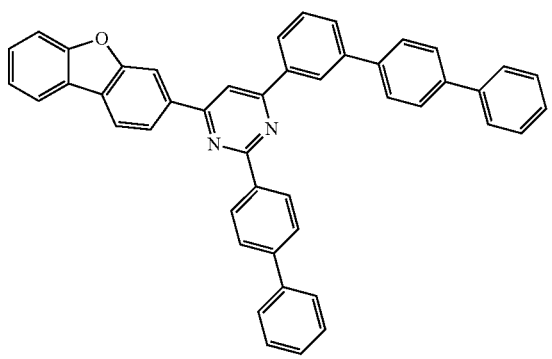
[B-80]
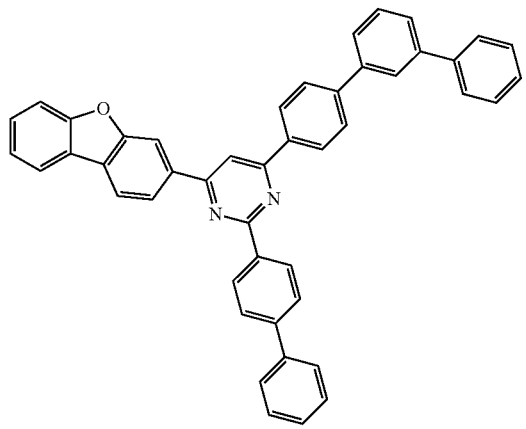
[B-81]
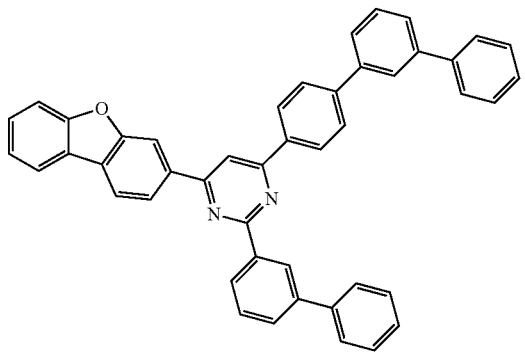
[C-1]
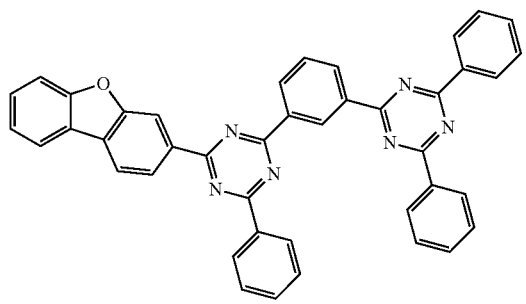
[C-2]
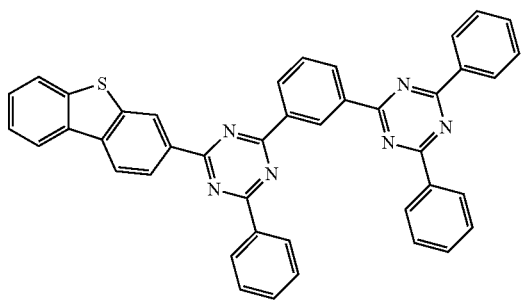

-continued
[C-3]
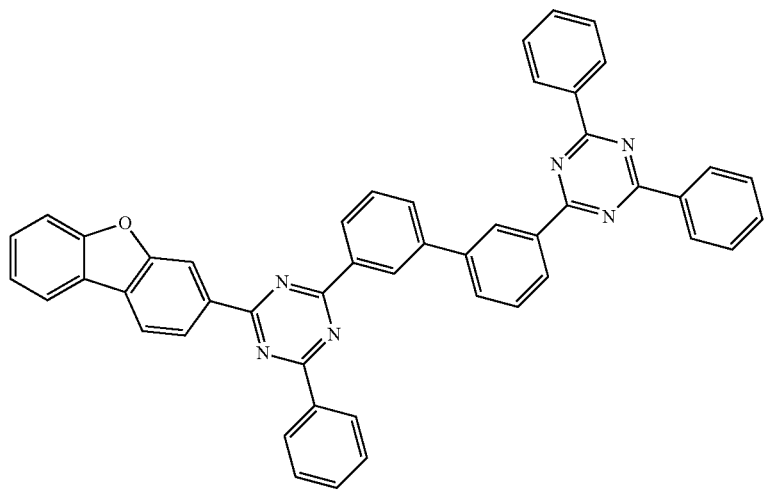
[C-4]
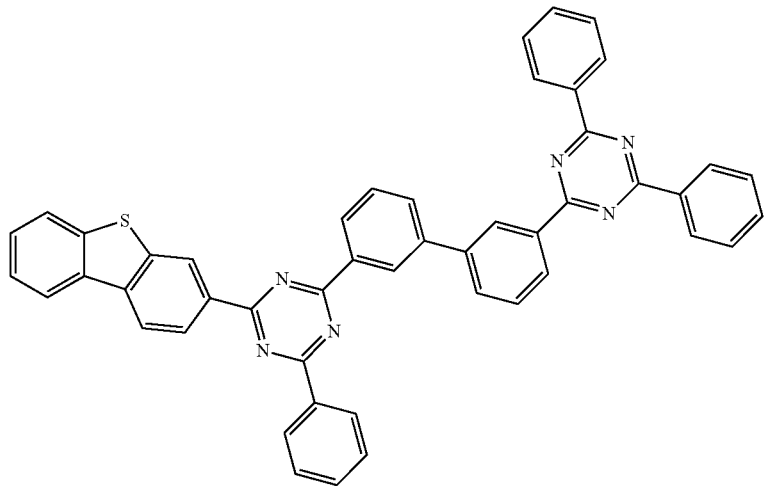
[C-5]
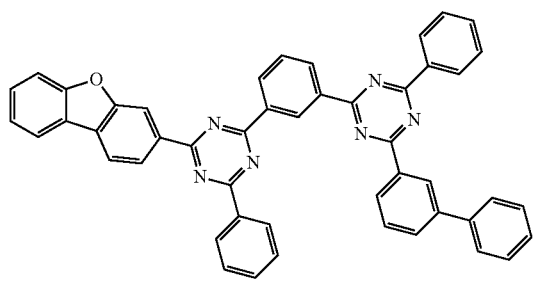
[C-6]
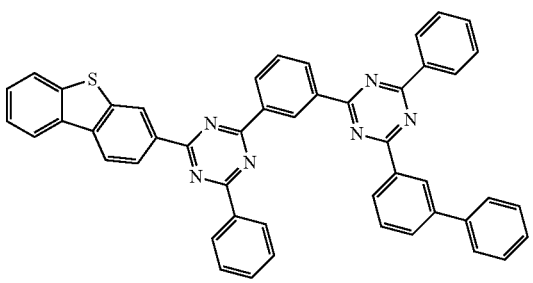
[C-7]
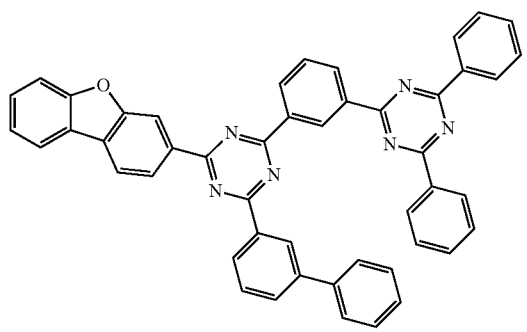
[C-8]
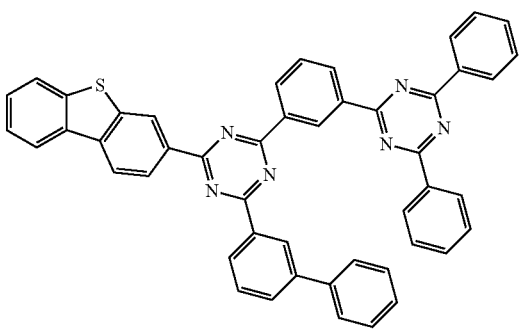

-continued
[C-9]
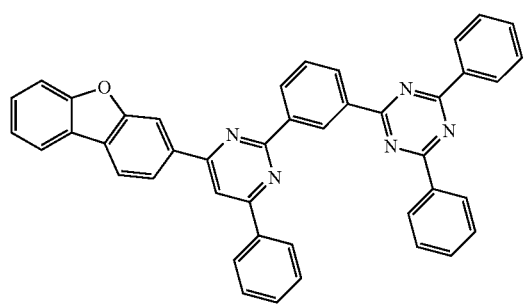
[C-10]
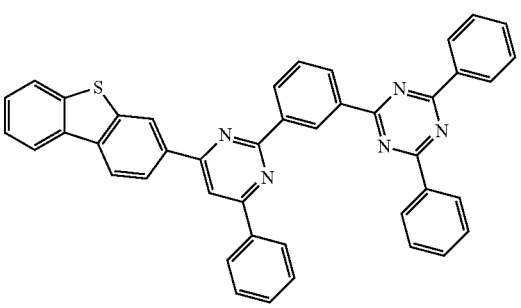
[C-11]
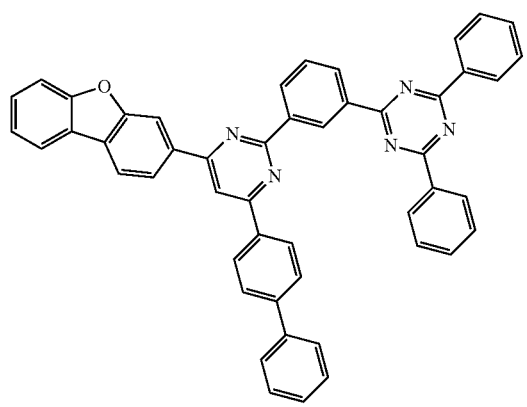
[C-12]
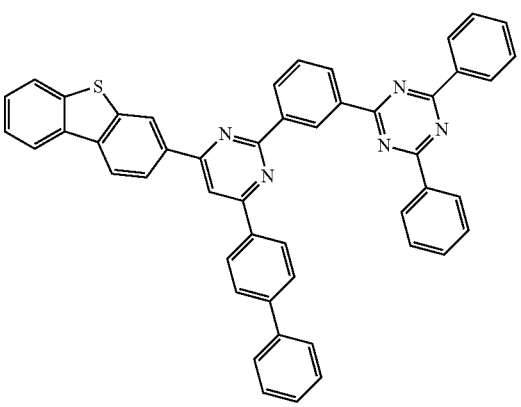
[C-13]
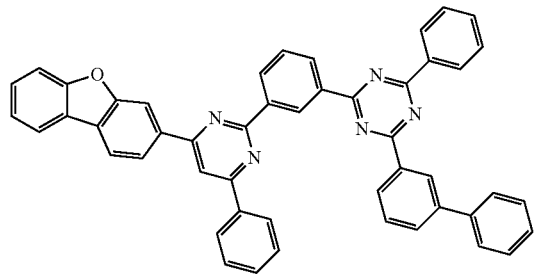
[C-14]
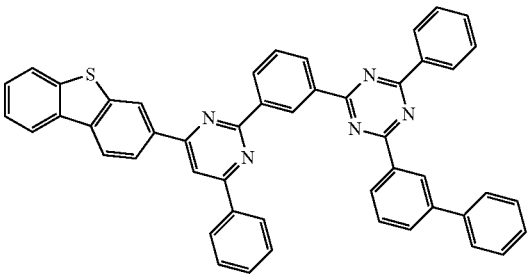
[C-15]
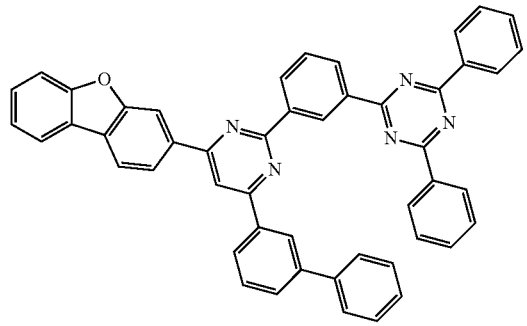
[C-16]
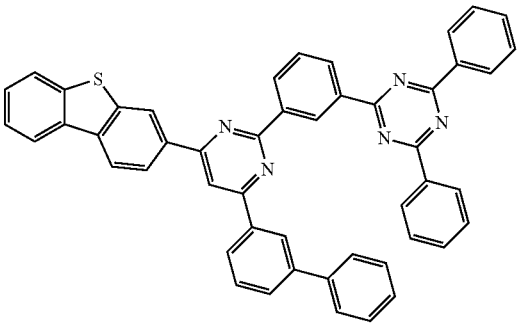

-continued
[C-17]
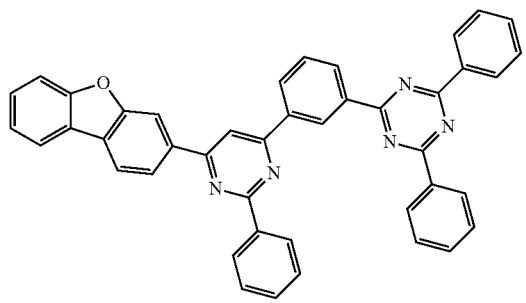
[C-18]
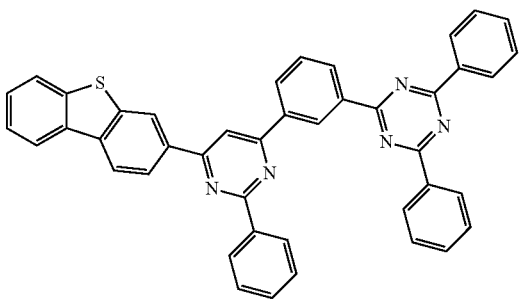
[C-19]
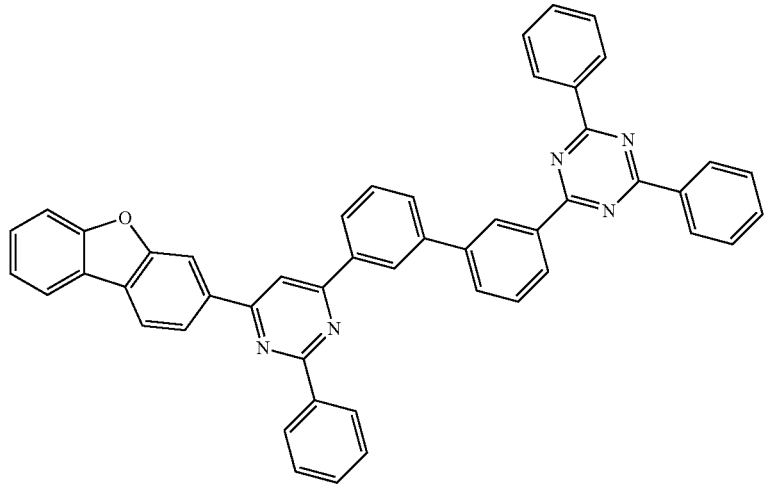
[C-20]
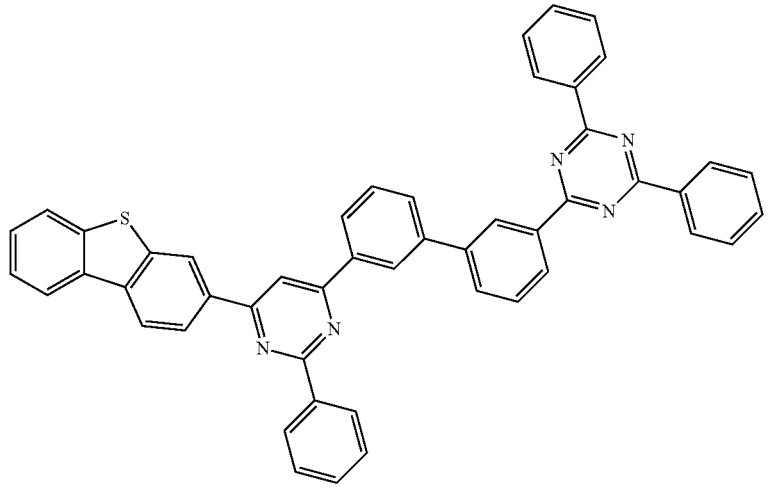
[C-21]
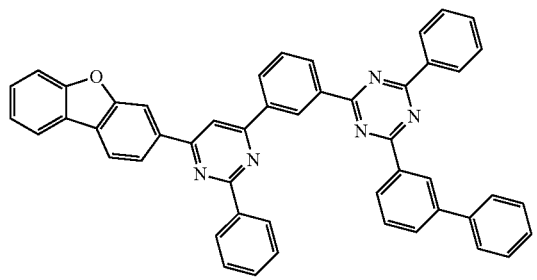
[C-22]
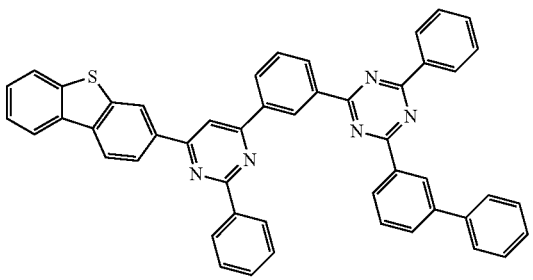

[C-23]
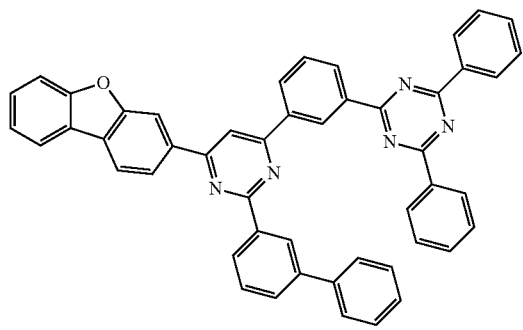
[C-24]
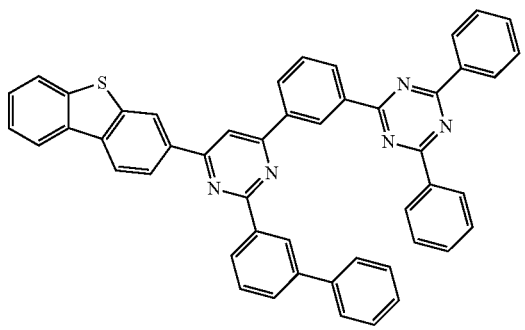
[C-25]
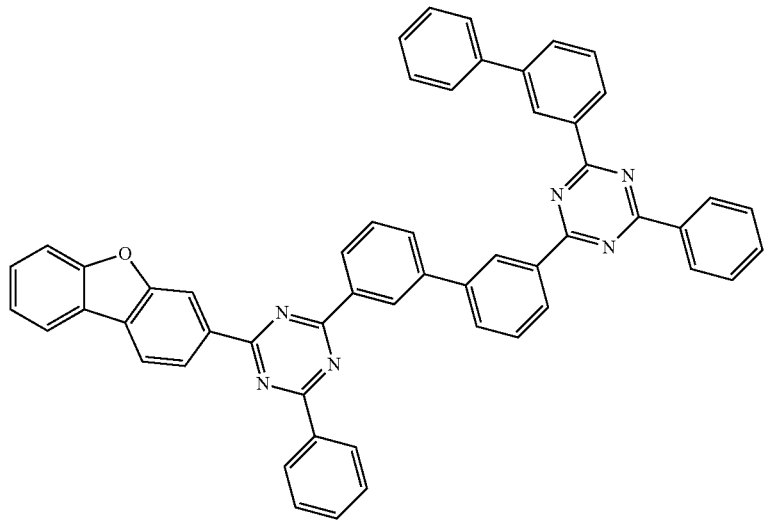
[C-26]
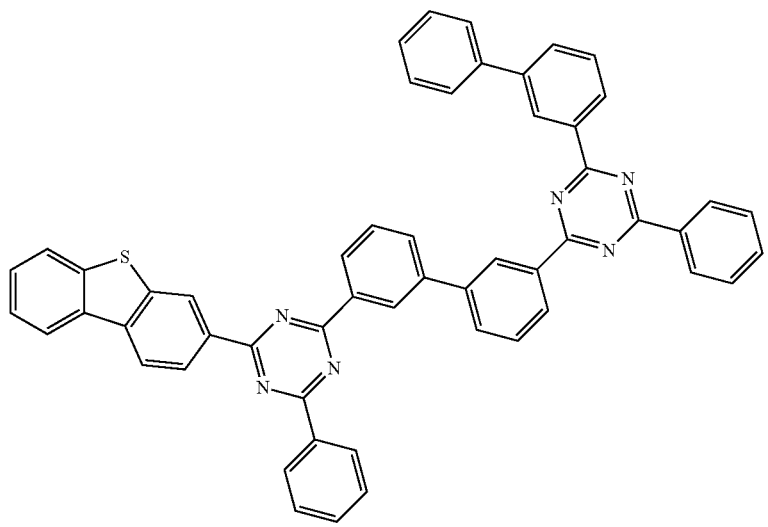

-continued
[C-27]
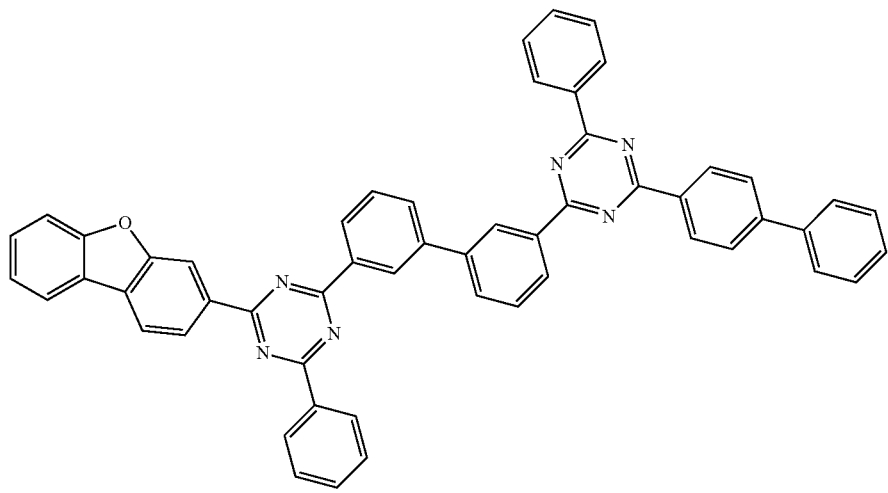
[C-28]
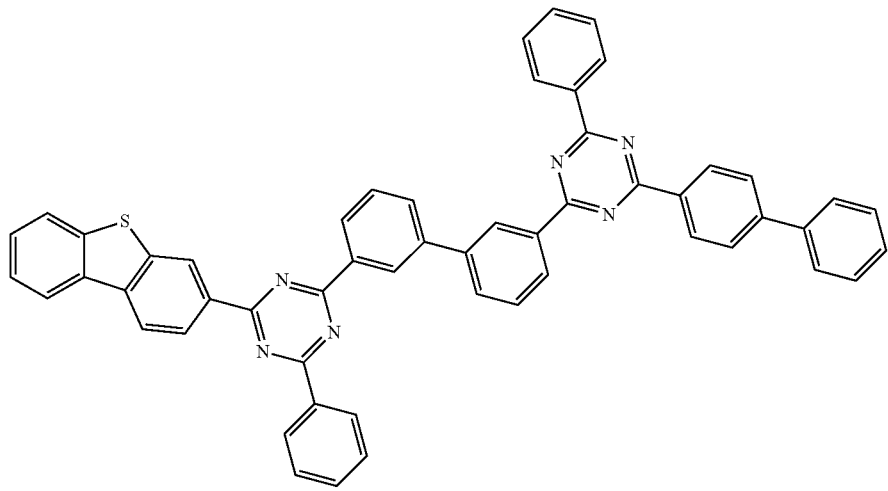
[C-29]
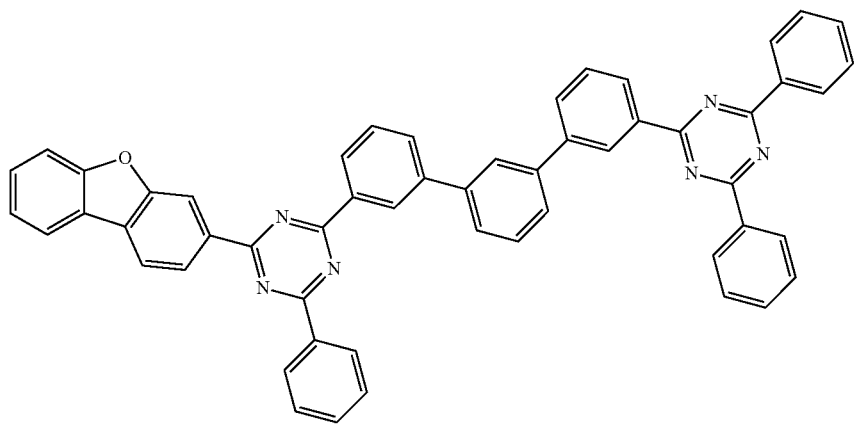

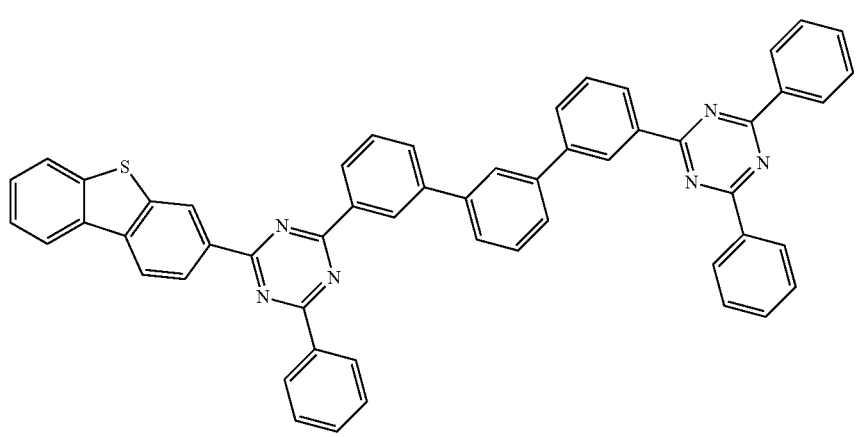
[C-30]
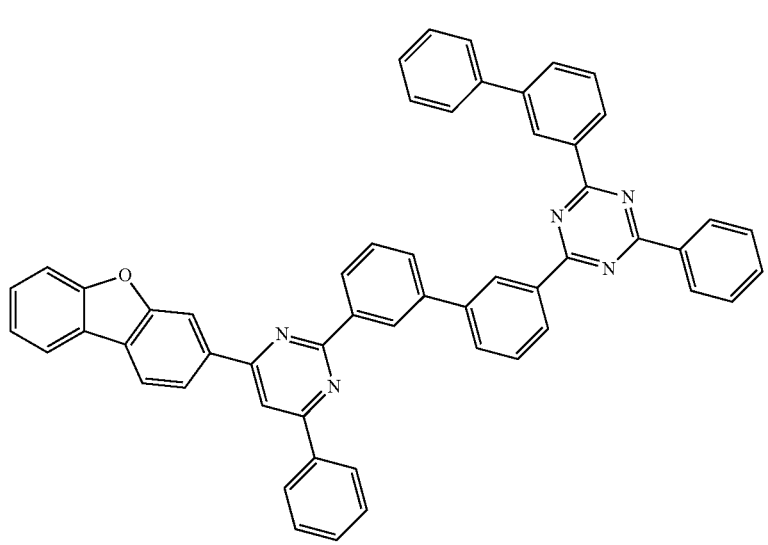
[C-31]
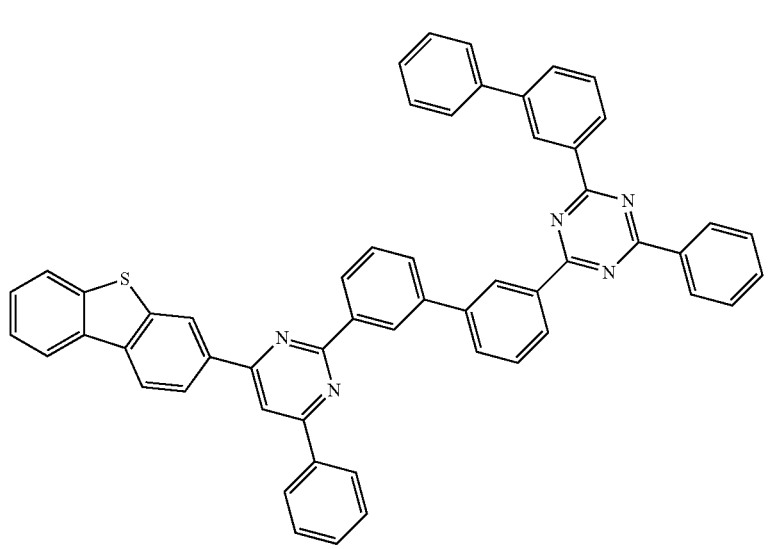
[C-32]

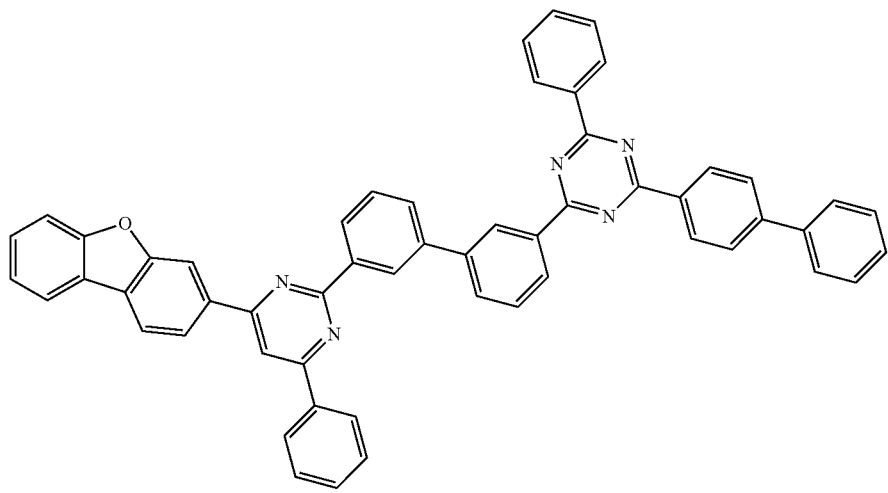
[C-33]
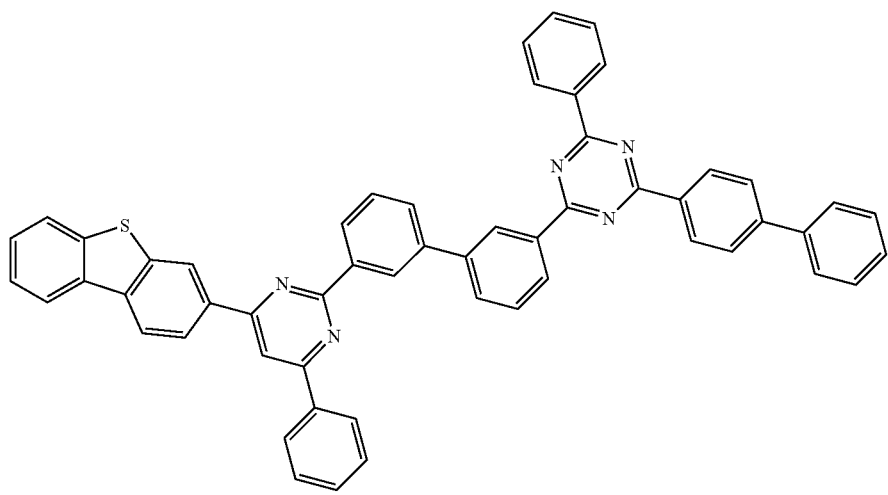
[C-34]
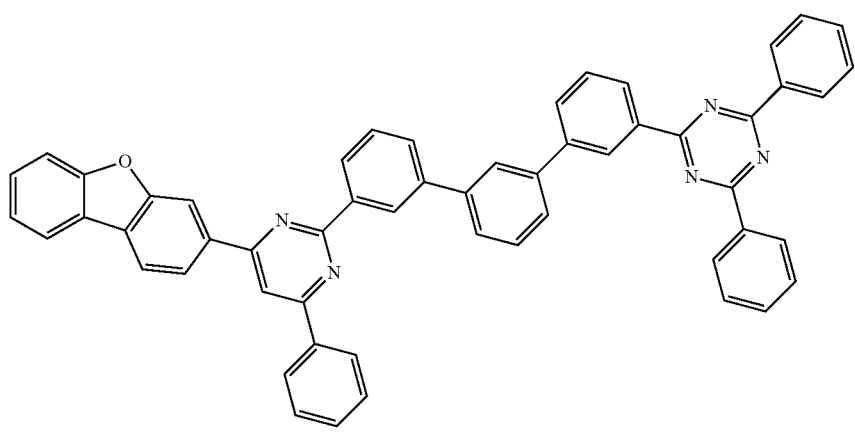
[C-35]

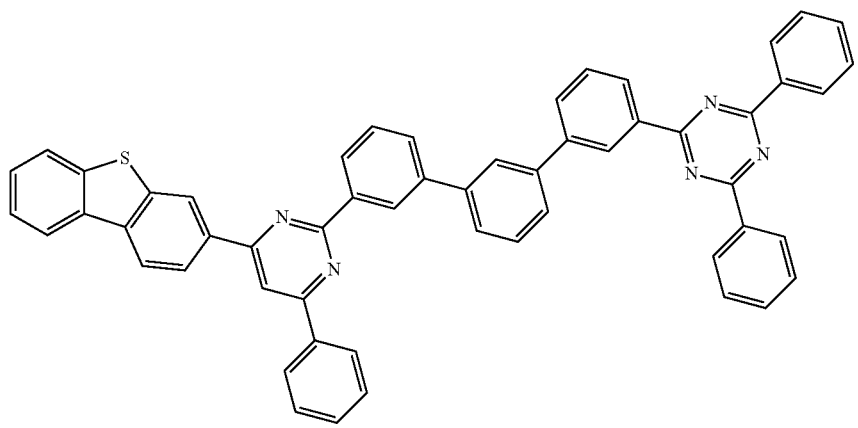
[C-36]
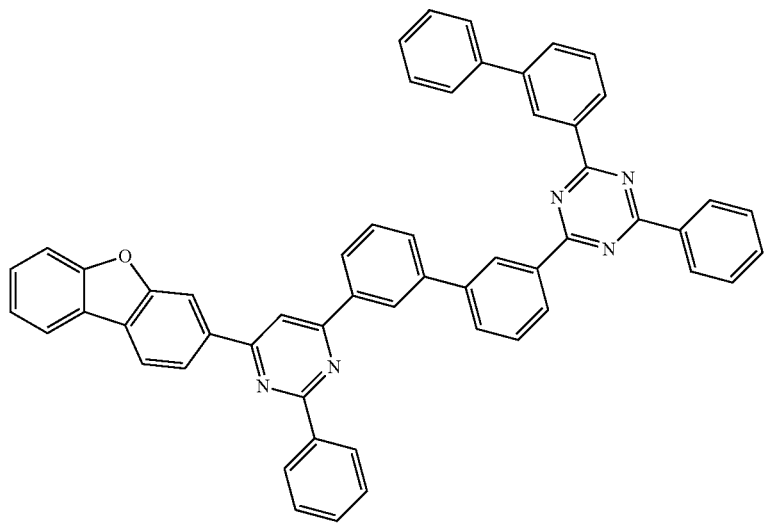
[C-37]
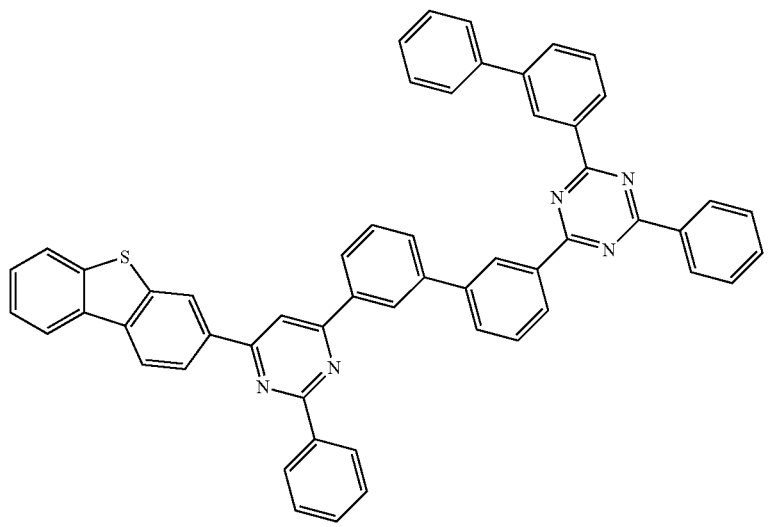
[C-38]

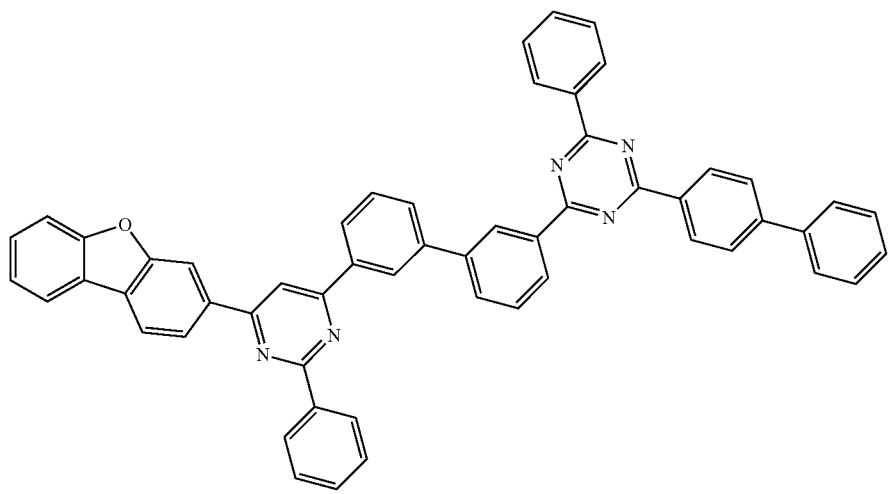
[C-39]
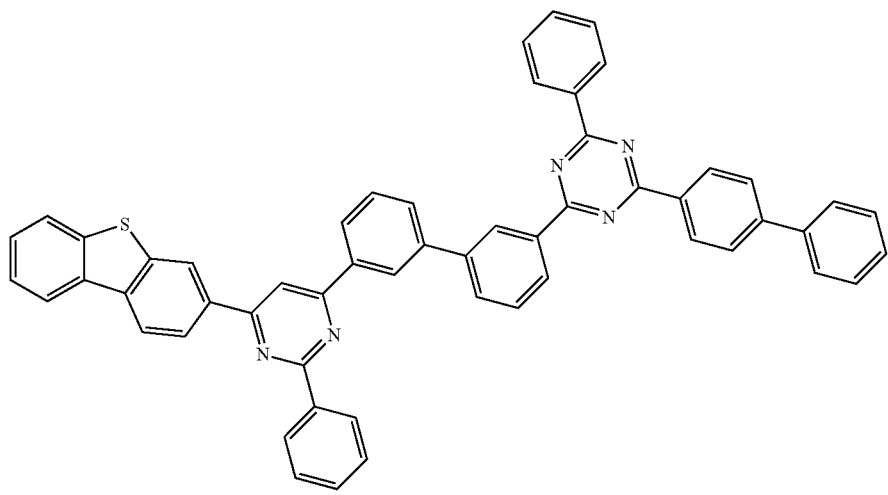
[C-40]
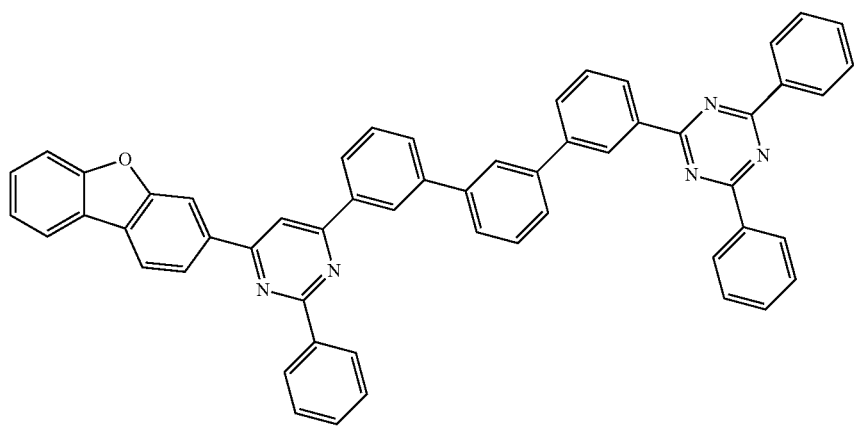
[C-41]

[C-42]
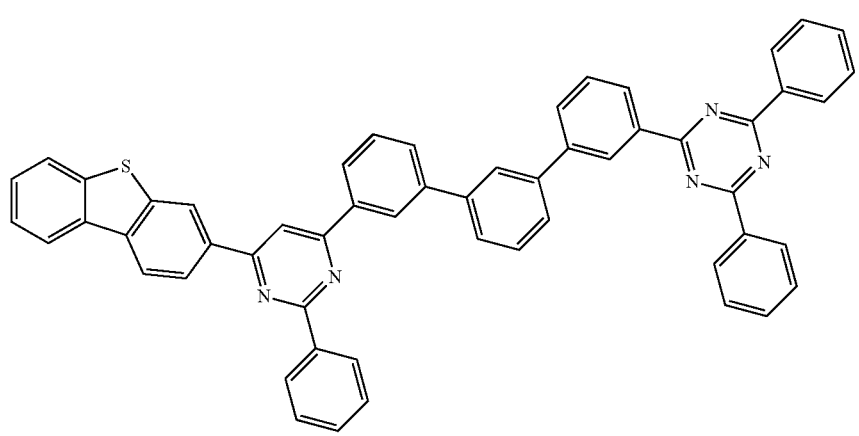
[C-43]
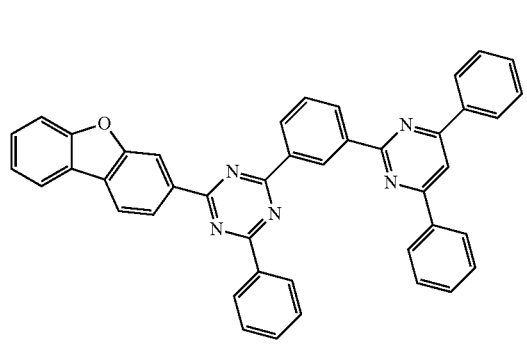
[C-44]
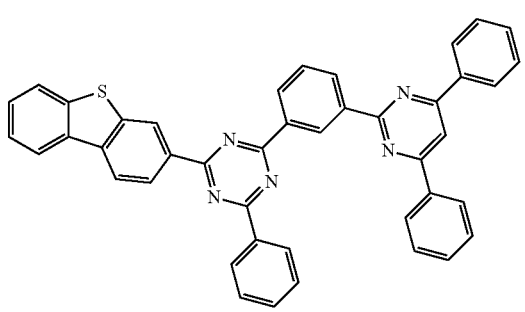
[C-45]
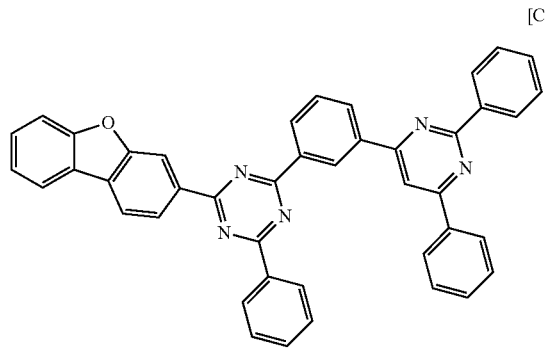
[C-46]
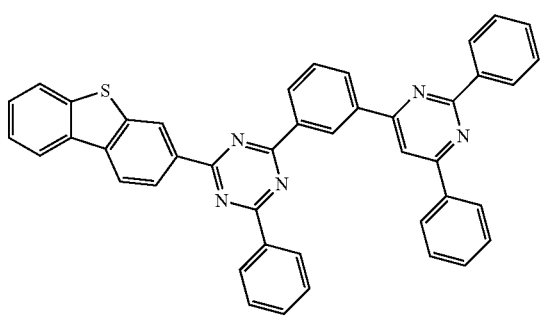
[C-47]
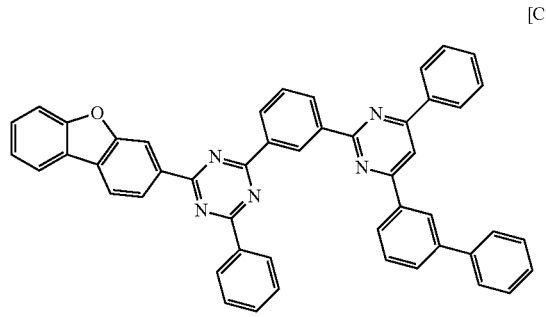
[C-48]
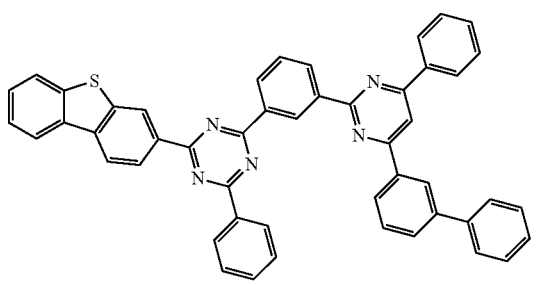

-continued
[C-49]
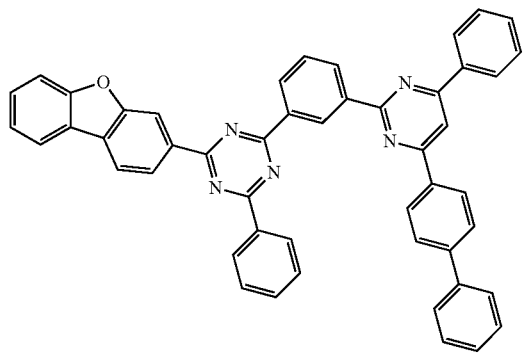
[C-50]
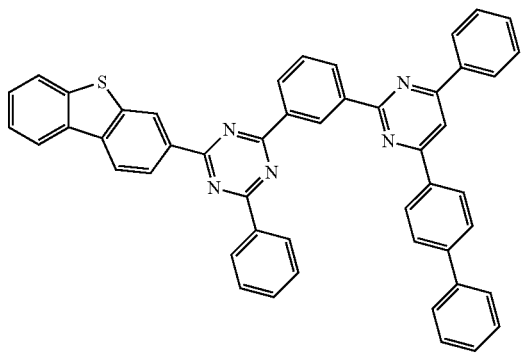
[C-51]
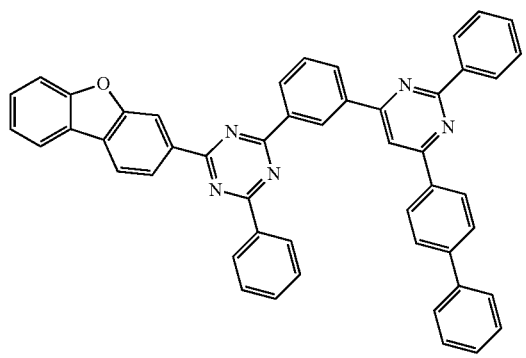
[C-52]
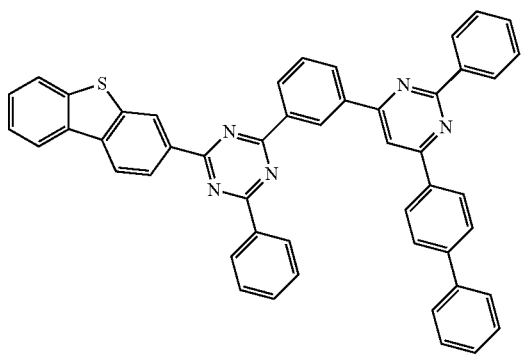
[C-53]
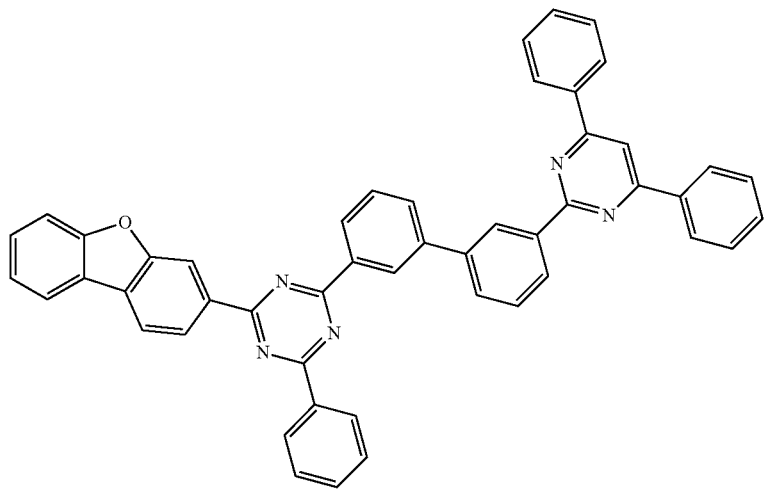

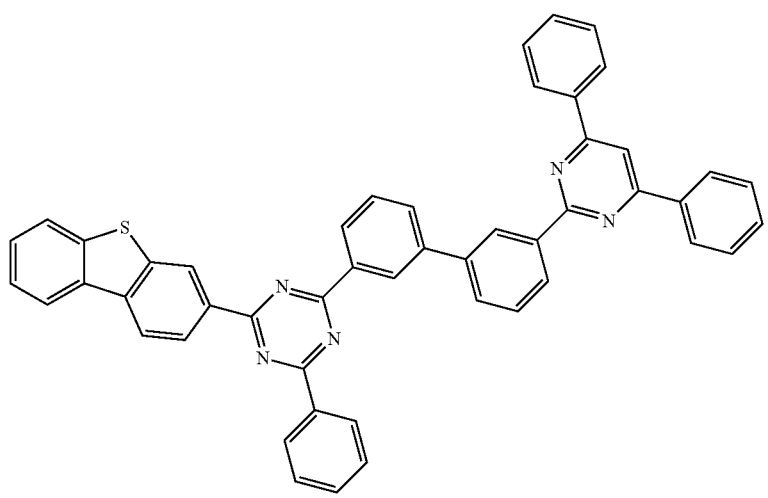
[C-54]
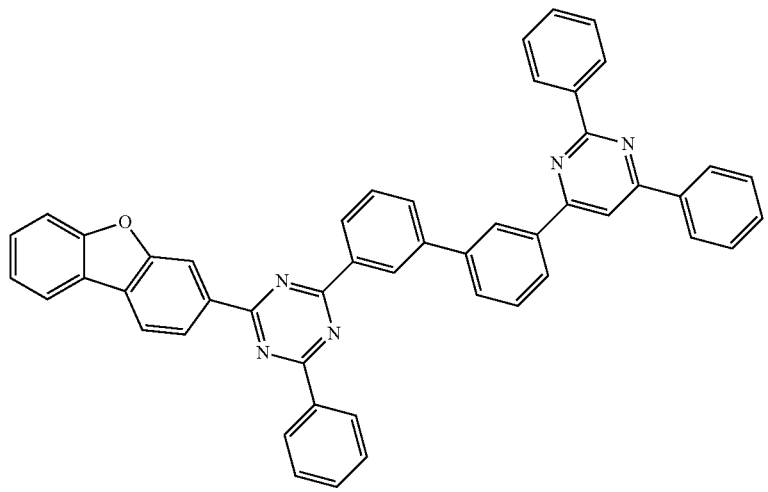
[C-55]
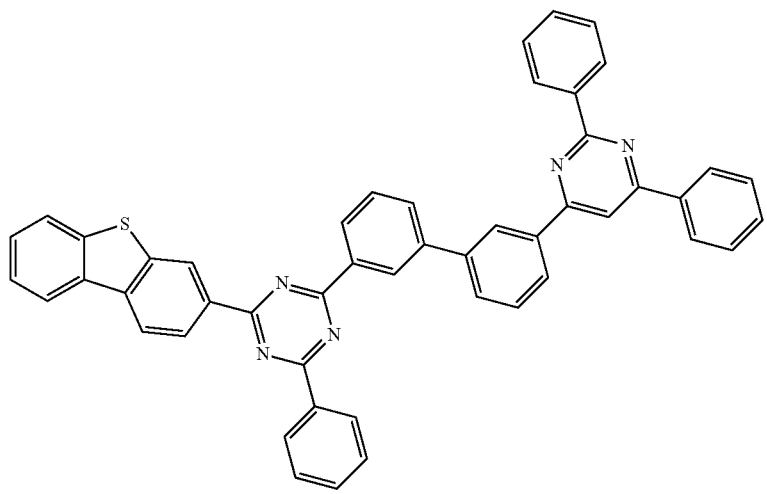
[C-56]

The second compound for an organic optoelectronic device that is used as a form of a composition with the first compound for an organic optoelectronic device may consist of a moiety represented by Chemical Formula 2 and a moiety represented by Chemical Formula 3.

[Chemical Formula 2]

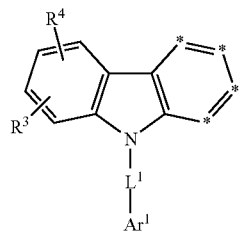

[Chemical Formula 3]

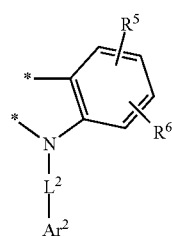

In Chemical Formulae 2 and 3, $Ar^1$ and $Ar^2$ are independently a substituted or unsubstituted C6 to C30 aryl group, a substituted or unsubstituted C2 to C30 heterocyclic group, or a combination thereof, two adjacent *'s of Chemical Formula 2 are bound to two adjacent *'s of Chemical Formula 3 to provide a fused ring and *'s of not providing the fused ring in Chemical Formula 2 are independently C-$L^a$-$R^c$, $R^c$ and $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, $L^a$, $L^1$, and $L^2$ are independently a single bond, a substituted or unsubstituted C6 to C30 arylene group, a substituted or unsubstituted C2 to C30 heteroarylene group, or a combination thereof, and "substituted" of Chemical Formulae 2 and 3 refers to replacement of at least one hydrogen by deuterium, a C1 to C4 alkyl group, a C6 to C18 aryl group, or a C2 to C18 heteroaryl group. In one example of the present invention, "substituted" of Chemical Formulae 2 and 3 refers to replacement of at least one hydrogen by deuterium, a C1 to C4 alkyl group, a C6 to C12 aryl group, or a C2 to C12 heteroaryl group. In a specific example of the present invention, "substituted" of Chemical Formulae 2 and 3 refers to replacement of at least one hydrogen by deuterium, a phenyl group, a meta-biphenyl group, a para-biphenyl group, a naphthyl group, a triphenylene group, a carbazolyl group, a pyridinyl group, a pyrimidinyl group, or a triazinyl group.

The second compound for an organic optoelectronic device may be for example represented by at least one of Chemical Formulae 2-I to 2-V according to a fusion position of Chemical Formula 2 and Chemical Formula 3.

[Chemical Formula 2-I]

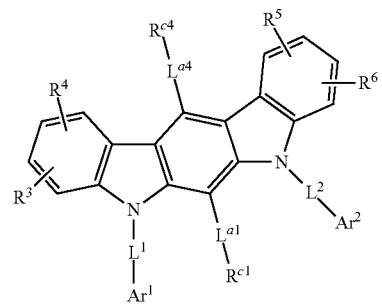

[Chemical Formula 2-II]

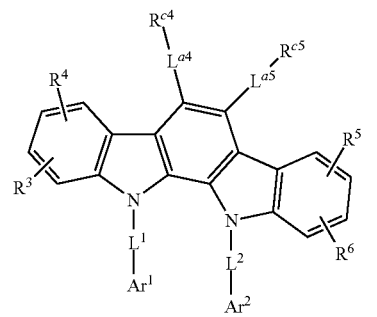

[Chemical Formula 2-III]

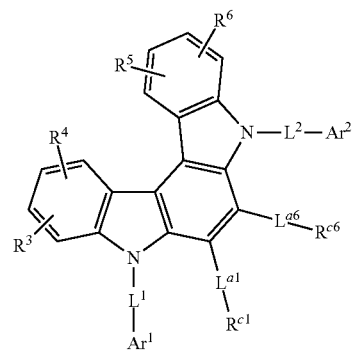

[Chemical Formula 2-IV]

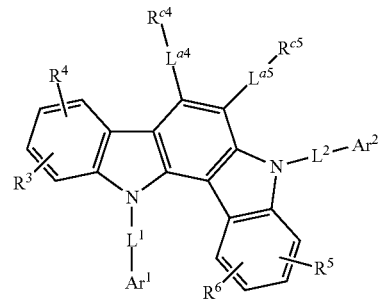

[Chemical Formula 2-V]

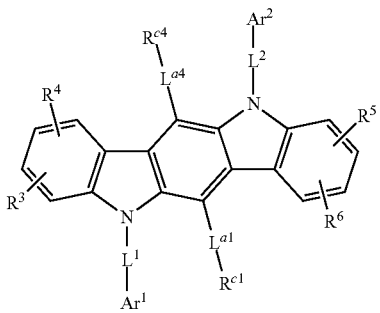

In Chemical Formulae 2-1 to 2-V, $L^1$ and $L^2$, $Ar^1$ and $Ar^2$, and $R^3$ to $R^6$ are the same as above, and the $R^{c1}$ and $R^{c4}$ to $R^{c6}$ may be the same as the definition of $R^c$, and may be for example independently hydrogen, deuterium, a substituted or unsubstituted C6 to C20 aryl group, or a substituted or unsubstituted C2 to C20 heterocyclic group.

Specifically, the $R^{c1}$ and $R^{c4}$ to $R^{c6}$ may independently be hydrogen, a substituted or unsubstituted carbazolyl group, a substituted or unsubstituted dibenzofuranyl group, or a substituted or unsubstituted dibenzothiophenyl group, and more specifically may be selected from substituents of Group III.

The $L^{a1}$ and $L^{a4}$ to $L^{a6}$ may be the same as the definition of $L^a$, and may be for example independently a single bond, or a substituted or unsubstituted C6 to C20 arylene group.

Specifically, the $L^{a1}$ and $L^{a4}$ to $L^{a6}$ may independently be a single bond, a substituted or unsubstituted para-phenylene group, a substituted or unsubstituted meta-phenylene group, or a substituted or unsubstituted biphenylene group.

In the most specific example embodiment of the present invention, $R^{c1}$ and $R^{c4}$ to $R^{c6}$ may independently be hydrogen, a substituted or unsubstituted carbazolyl group, a substituted or unsubstituted dibenzofuranyl group, or a substituted or unsubstituted dibenzothiophenyl group, provided that at least one of the $R^{c1}$ and $R^{c4}$ may be a substituted or unsubstituted carbazolyl group, a substituted or unsubstituted dibenzofuranyl group, or a substituted or unsubstituted dibenzothiophenyl group and the remainder is all hydrogen, and the $L^{a1}$ and $L^{a4}$ to $L^{a6}$ may independently be a single bond, or a substituted or unsubstituted C6 to C18 arylene group, provided that at least one of the $L^{a1}$ and $L^{a4}$ is a single bond, a substituted or unsubstituted para-phenylene group, a substituted or unsubstituted meta-phenylene group, or a substituted or unsubstituted biphenylene group and the remainder may be all single bonds. As more specific examples, the $R^{c1}$ and $R^{c4}$ to $R^{c6}$ may be all hydrogen and the $L^{a1}$ and $L^{a4}$ to $L^{a6}$ may be all single bonds.

In an example embodiment of the present invention, $L^1$ and $L^2$ may independently be a single bond, a substituted or unsubstituted phenylene group, a substituted or unsubstituted biphenylene group, a substituted or unsubstituted pyridylene group, or a substituted or unsubstituted pyrimidylene group, and the $Ar^1$ and $Ar^2$ may independently be a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted fluorenyl group, a substituted or unsubstituted carbazolyl group, a substituted or unsubstituted pyridyl group, a substituted or unsubstituted pyrimidinyl group, a substituted or unsubstituted triazinyl group, a substituted or unsubstituted dibenzofuranyl group, or a substituted or unsubstituted dibenzothiophenyl group.

In an example embodiment of the present invention, the $Ar^1$ and $Ar^2$ may be a substituted or unsubstituted phenyl group, a substituted or unsubstituted biphenyl group, a substituted or unsubstituted terphenyl group, a substituted or unsubstituted naphthyl group, a substituted or unsubstituted carbazolyl group, a substituted or unsubstituted dibenzofuranyl group, or a substituted or unsubstituted dibenzothiophenyl group, wherein "substituted" refers to replacement of one hydrogen by deuterium, a C1 to C5 alkyl group or a C6 to C18 aryl group.

In a more specific example embodiment of the present invention, the $L^1$ and $L^2$ may independently be selected from a single bond, or linking groups of Group II and the $Ar^1$ and $Ar^2$ may independently be selected from substituents of Group III.

[Group II]

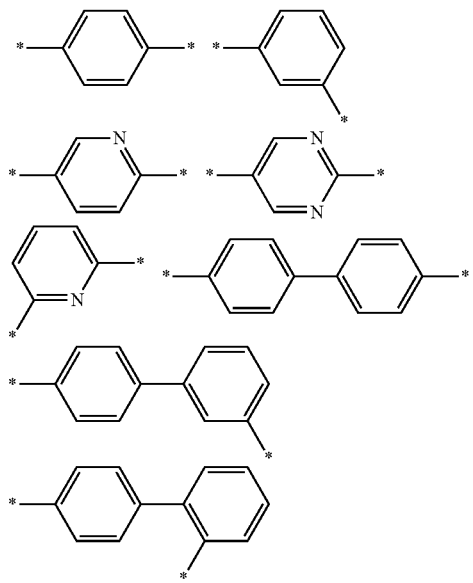

[Group III]

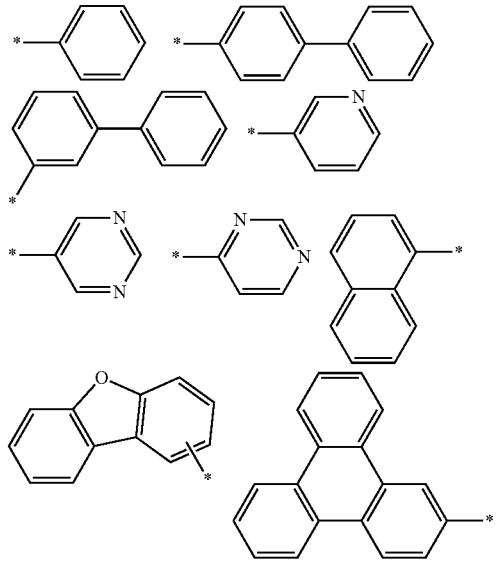

-continued

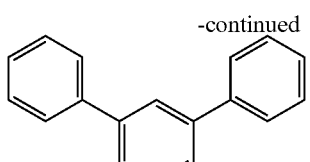
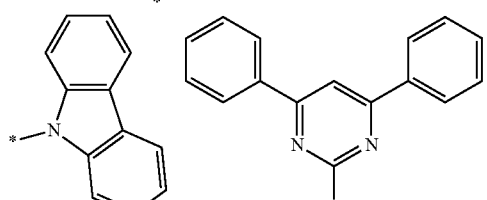
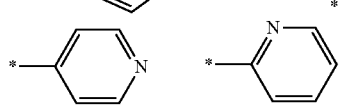
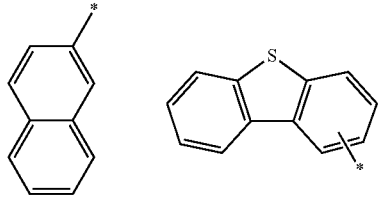
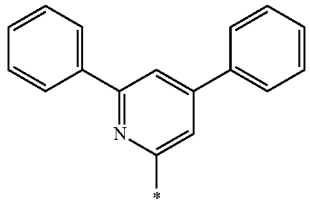
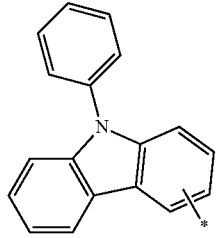
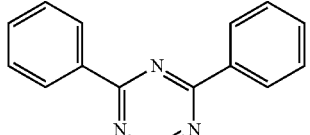
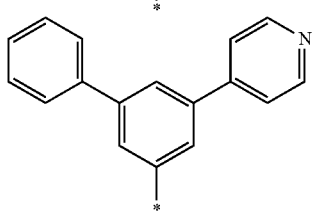

In Group II and Group III, * is a linking point with an adjacent atom.

In the most specific example embodiment of the present invention, the $L^1$ and $L^2$ may independently be a single bond, or a substituted or unsubstituted phenylene group and the $Ar^1$ and $Ar^2$ may independently be a substituted or unsubstituted phenyl group, a substituted or unsubstituted biphenyl group, or a substituted or unsubstituted carbazolyl group.

The second compound for an organic optoelectronic device consisting of a combination of the moiety represented by Chemical Formula 2 and the moiety represented by Chemical Formula 3 may be for example selected from compounds of Group 2, but is not limited thereto.

[Group 2]

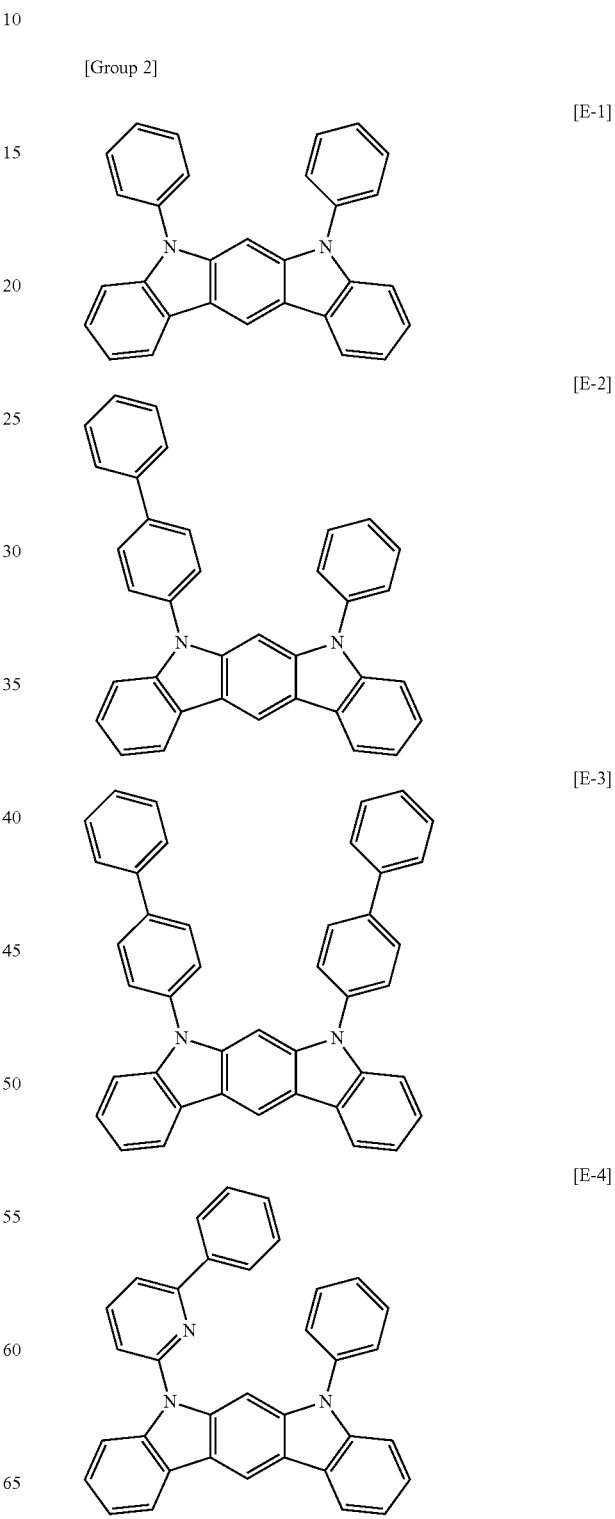

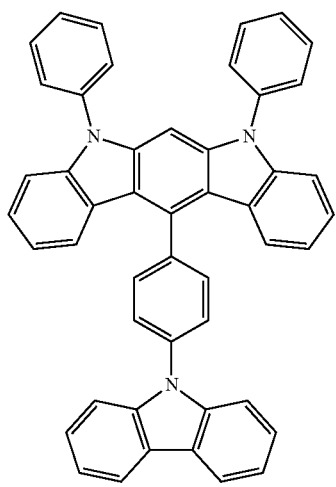
[E-5]
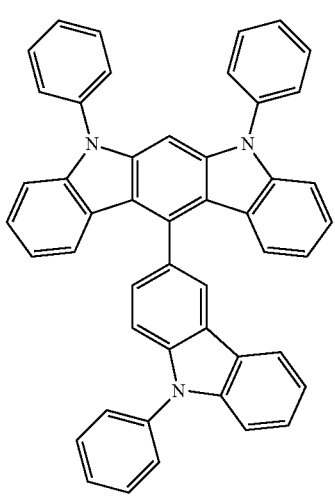
[E-8]
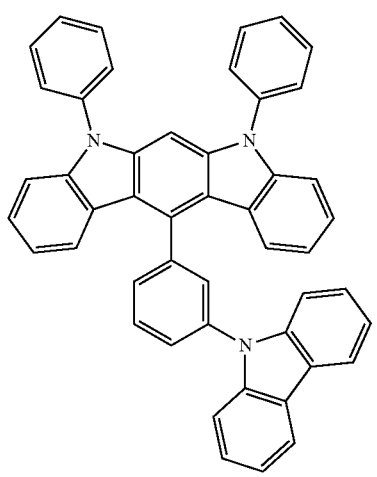
[E-6]
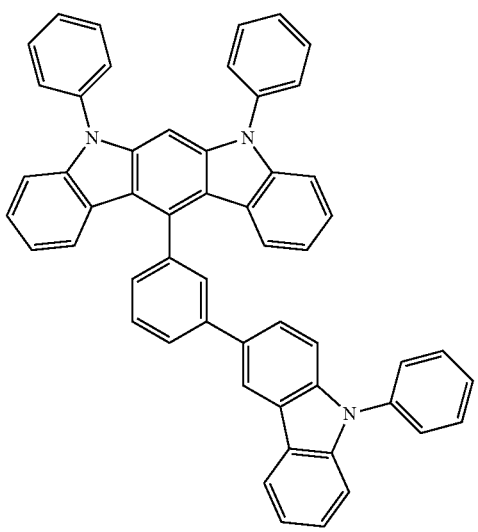
[E-9]
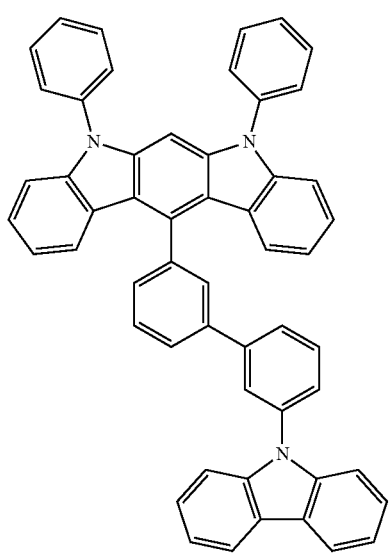
[E-7]
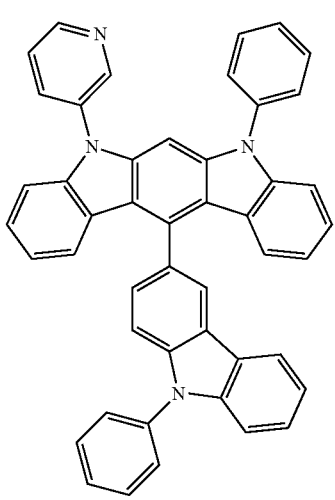
[E-10]

[E-11] 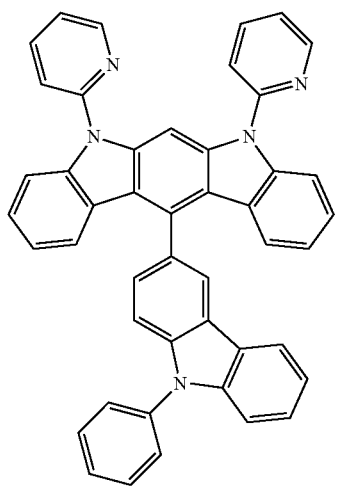
[E-12] 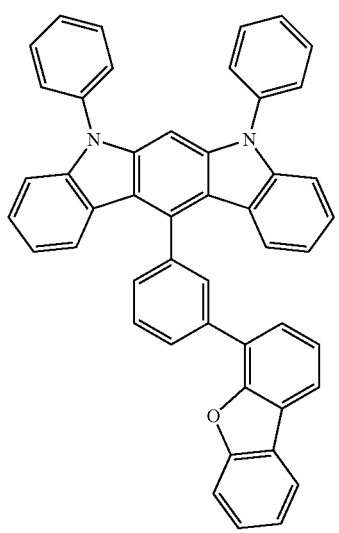
[E-13] 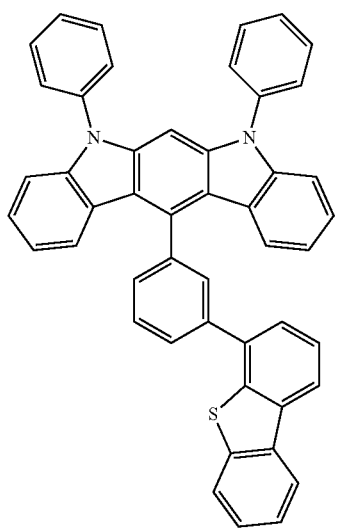
[E-14] 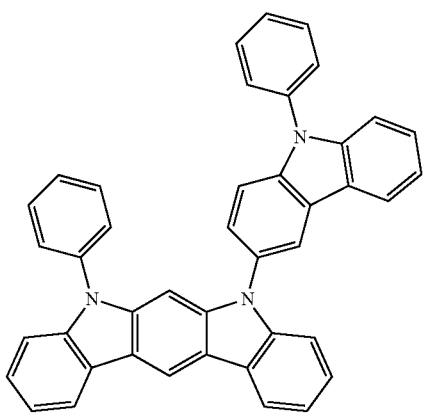
[E-15] 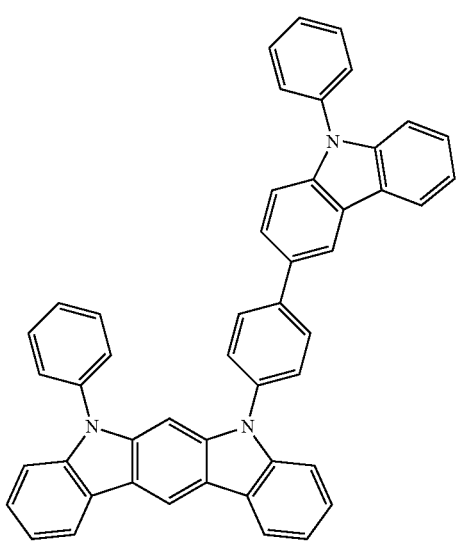
[E-16] 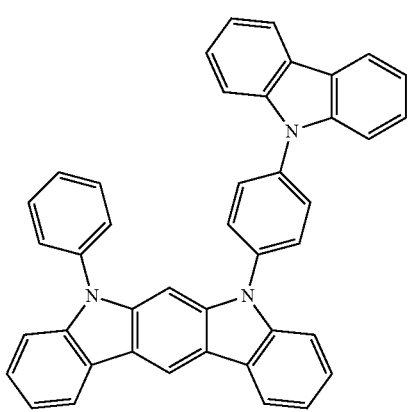

[E-17]
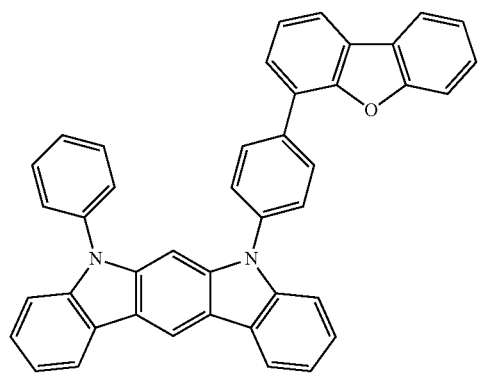
[E-18]
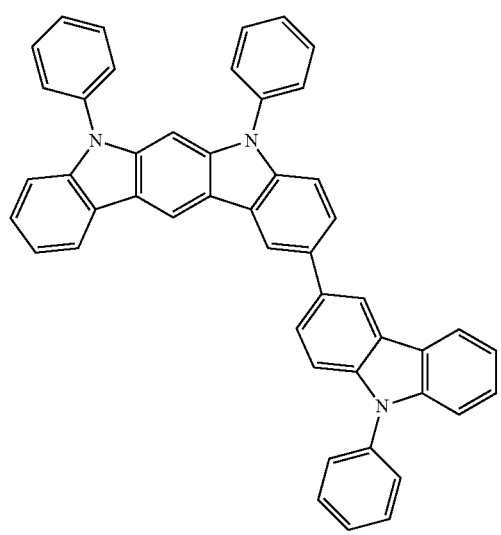
[E-19]
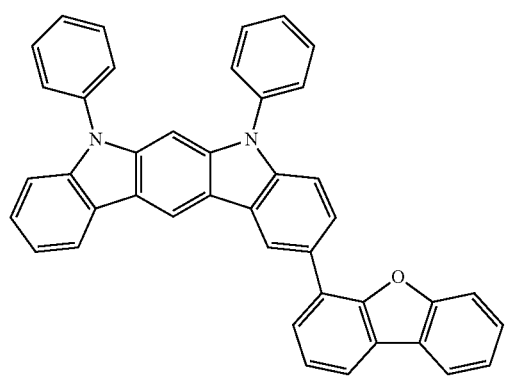
[E-20]
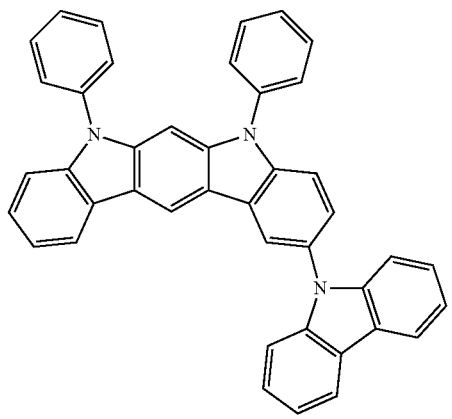
[E-21]
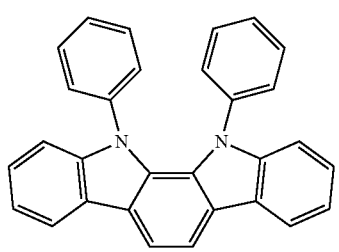
[E-22]
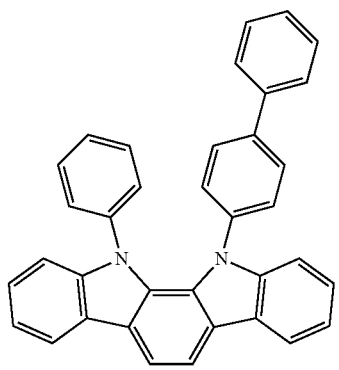
[E-23]
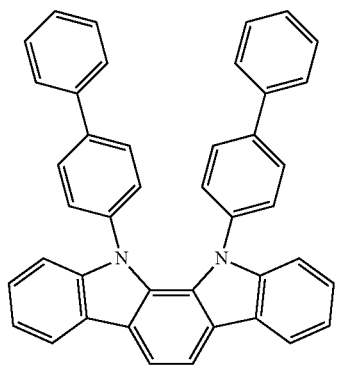

[E-24]
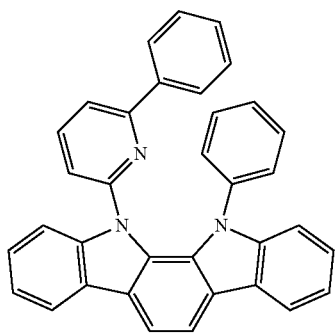
[E-25]
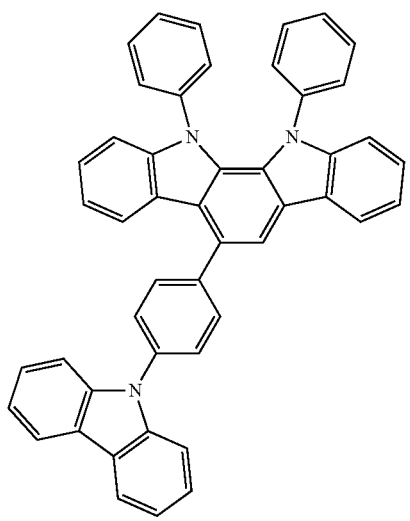
[E-26]
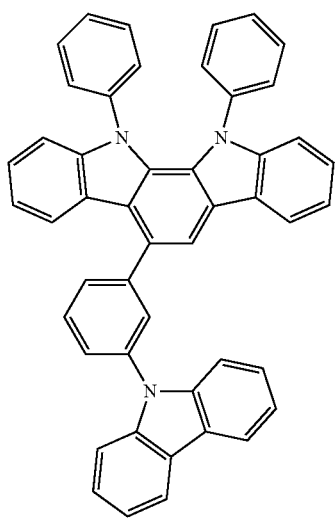
[E-27]
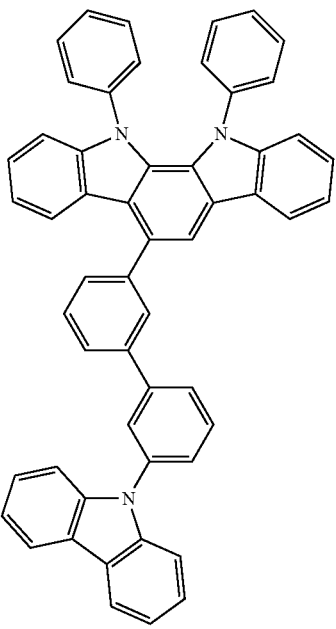
[E-28]
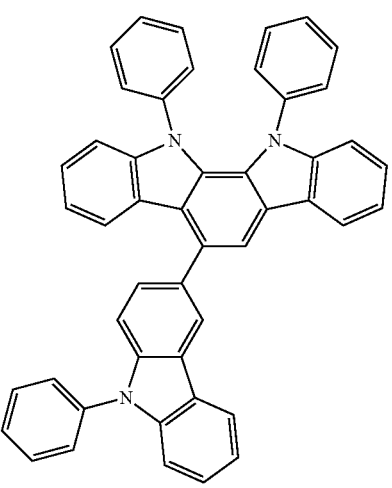

[E-29]
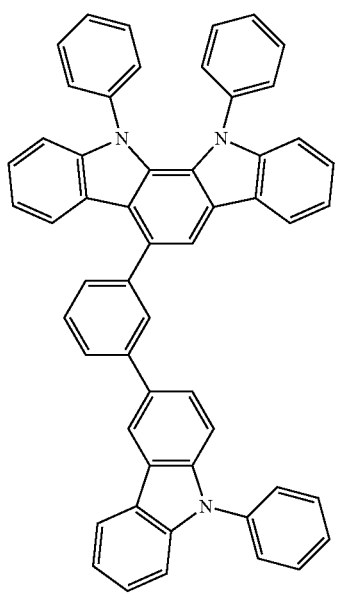
[E-30]
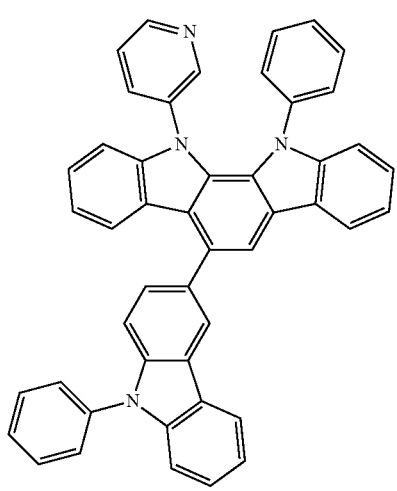
[E-31]
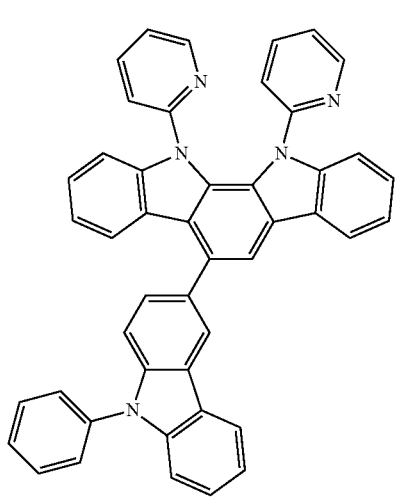
[E-32]
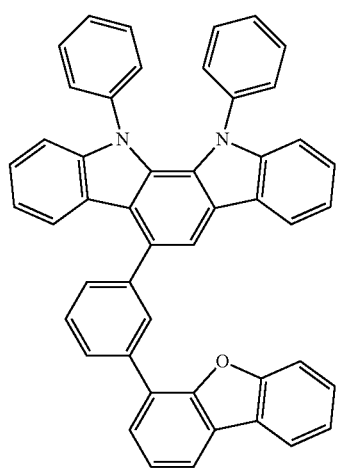
[E-33]
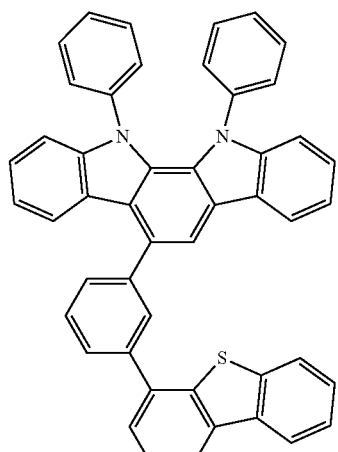
[E-34]
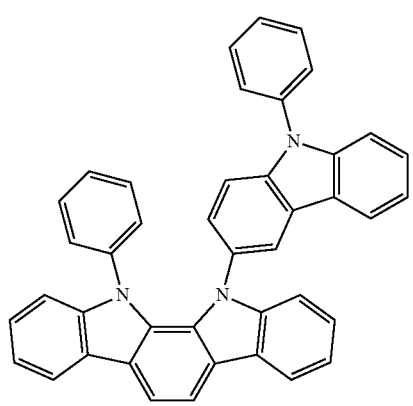

[E-35]
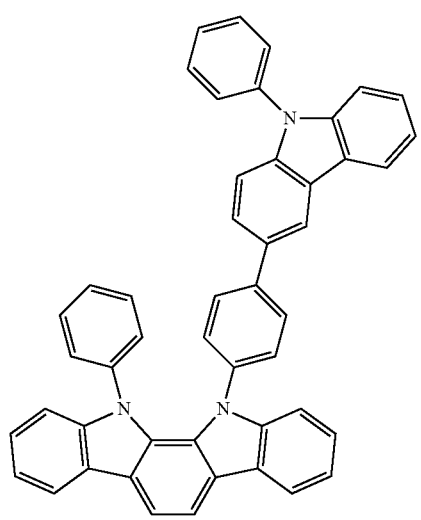
[E-36]
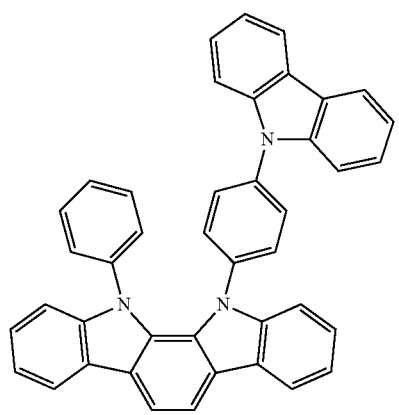
[E-37]
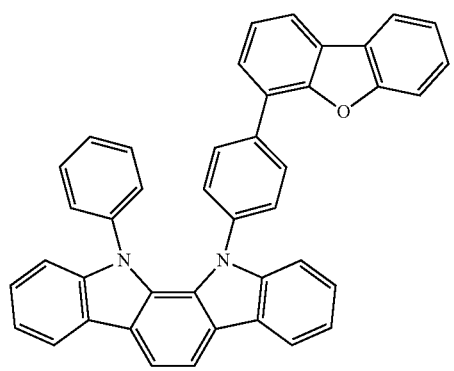
[E-38]
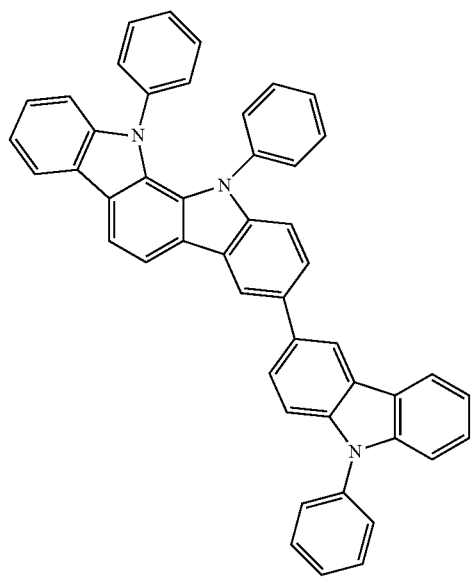
[E-39]
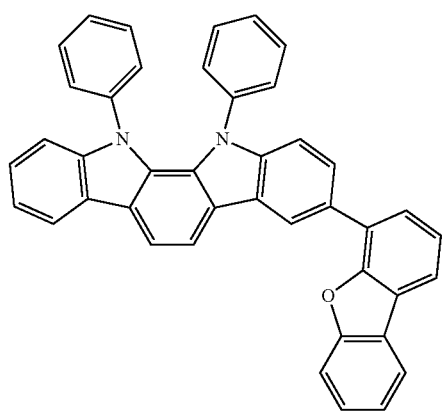
[E-40]
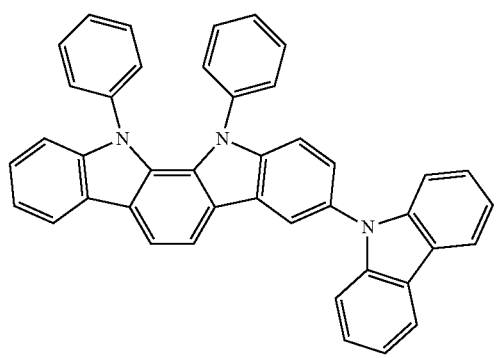
[E-41]
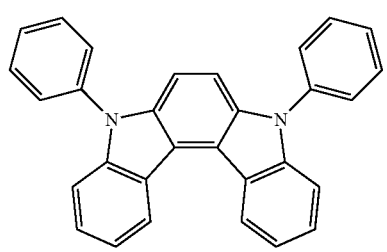

[E-42]
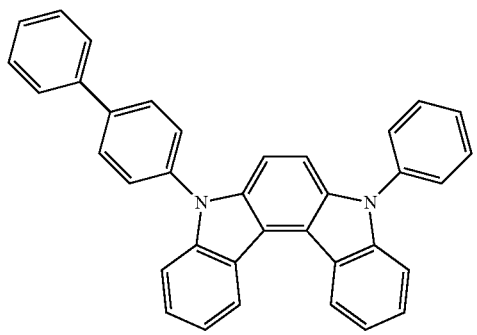
[E-45]
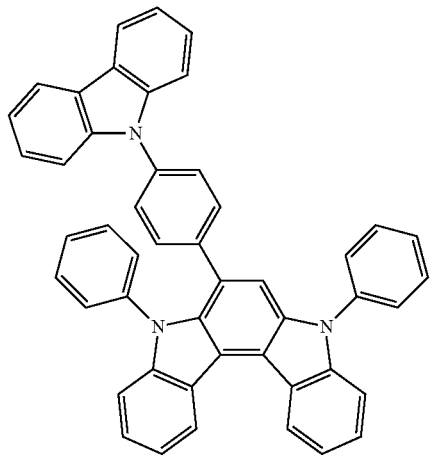
[E-43]
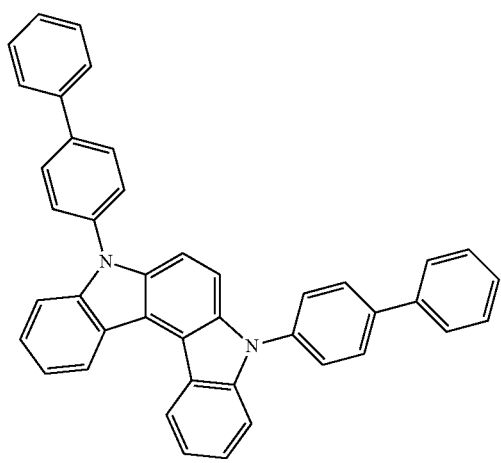
[E-46]
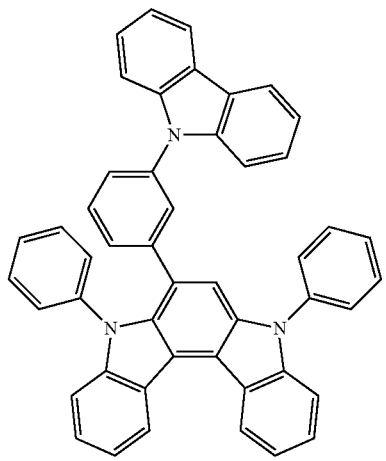
[E-44]
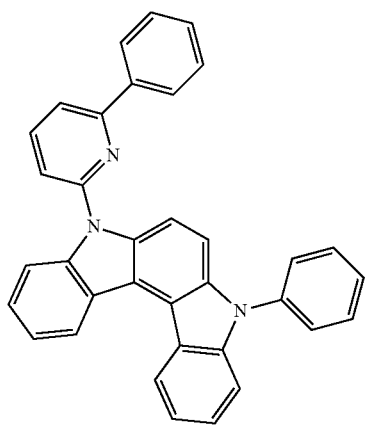
[E-47]
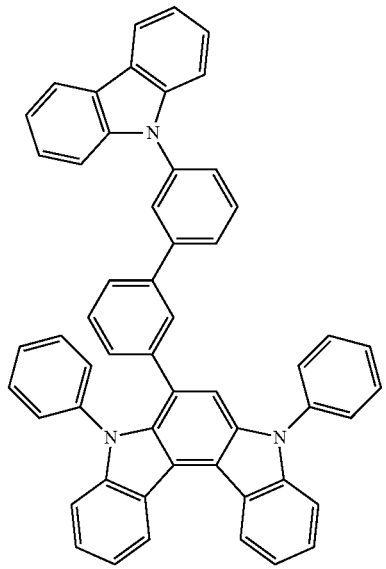

[E-48]
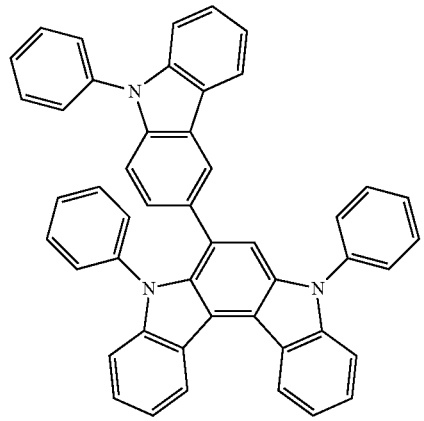
[E-51]
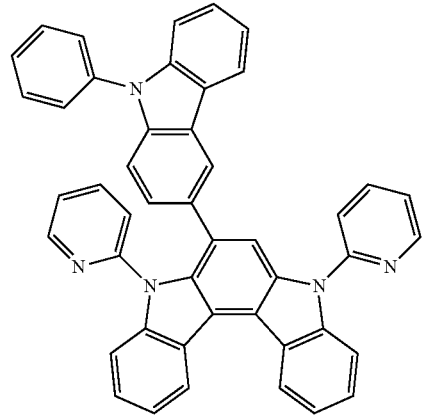
[E-49]
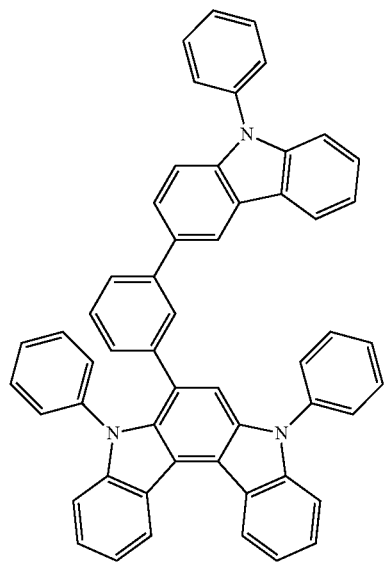
[E-52]
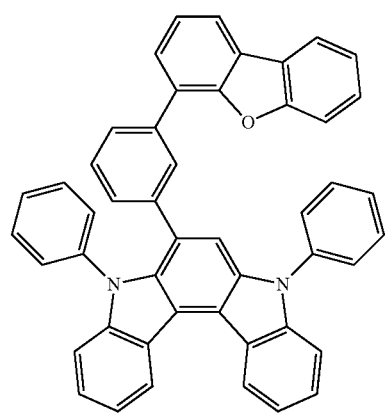
[E-53]
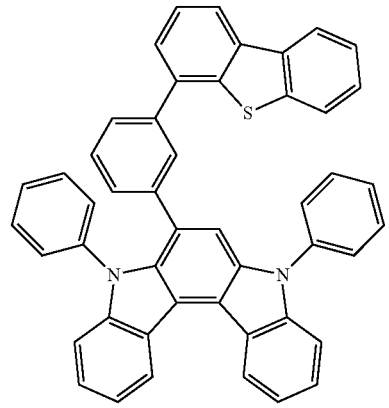
[E-50]
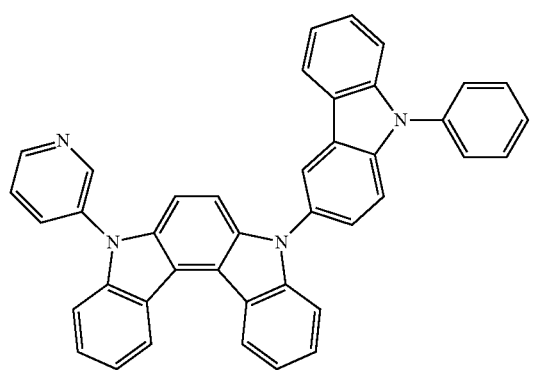
[E-54]
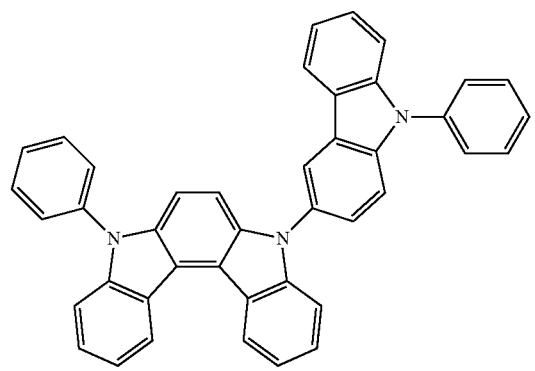

[E-55]
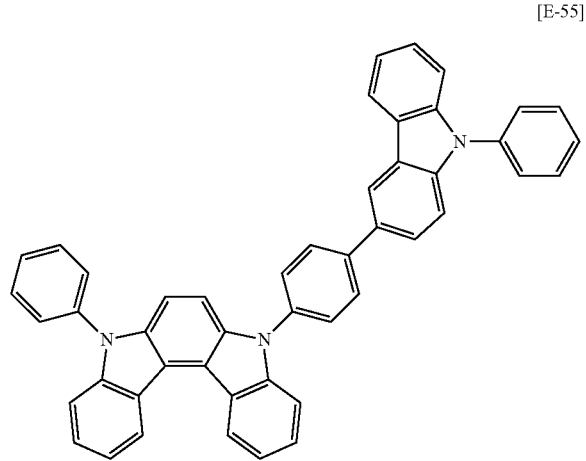
[E-58]
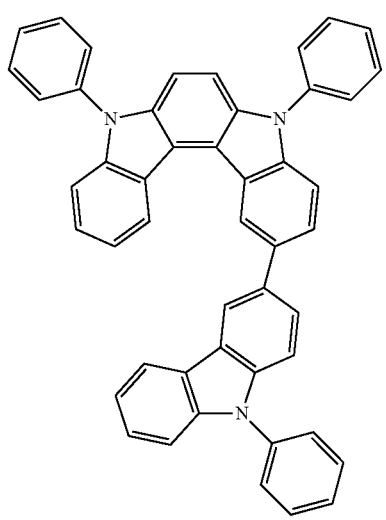
[E-56]
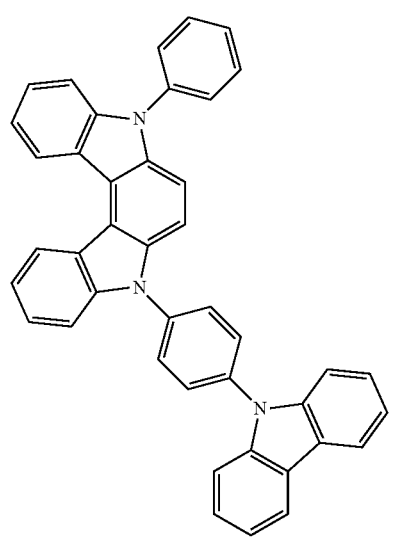
[E-59]
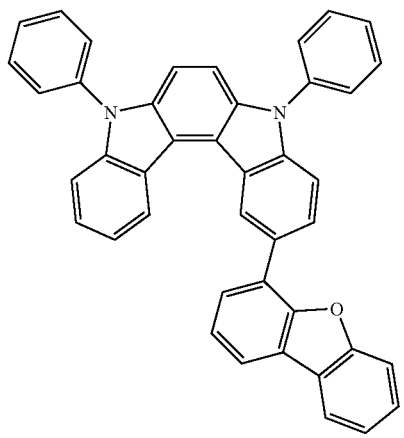
[E-57]
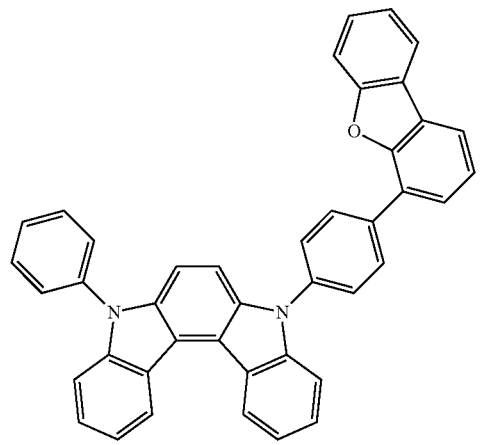
[E-60]
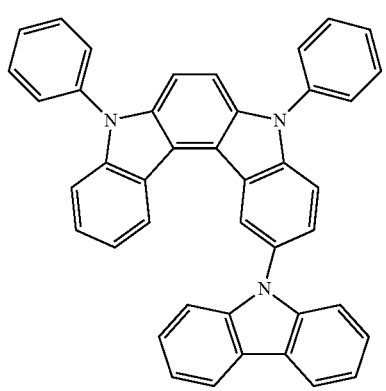

[E-61]
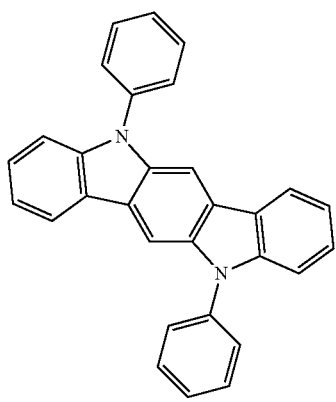
[E-62]
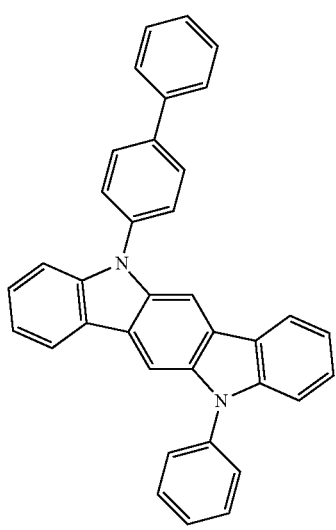
[E-63]
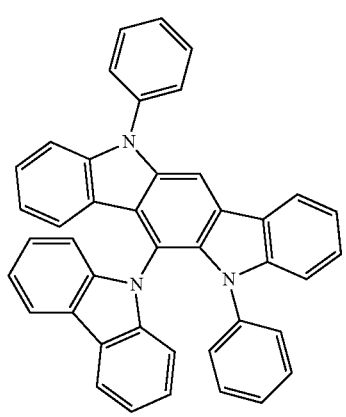
[E-64]
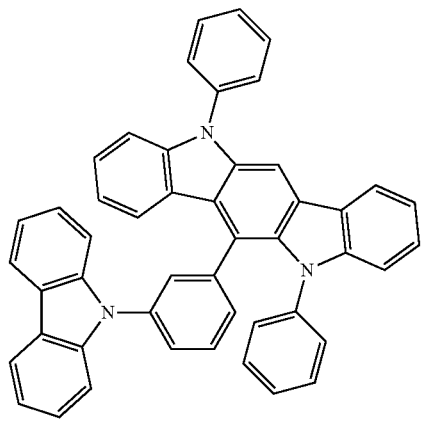
[E-65]
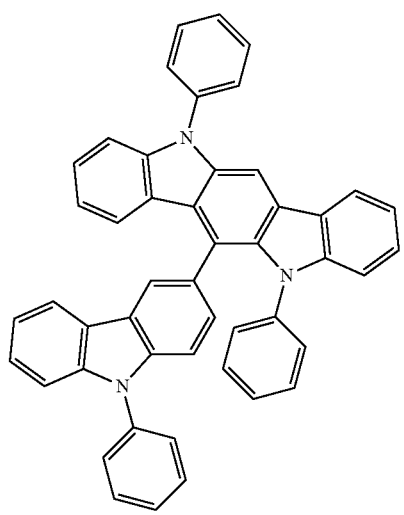
[E-66]
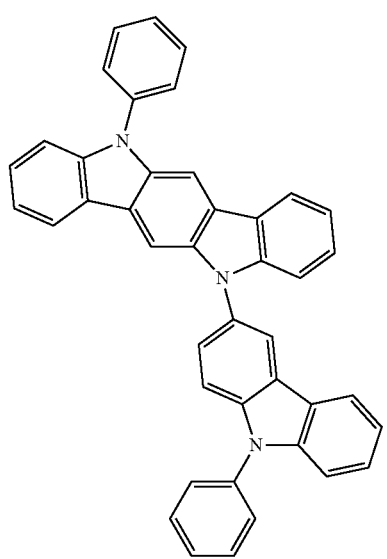

[E-67]
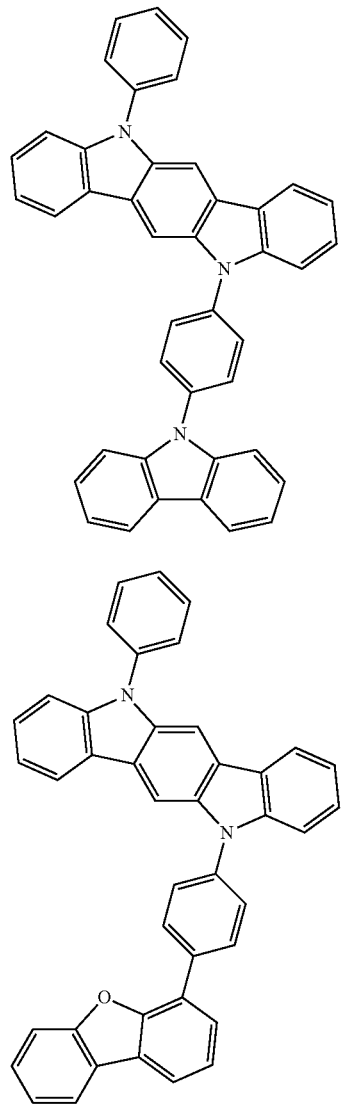
[E-68]
[E-69]
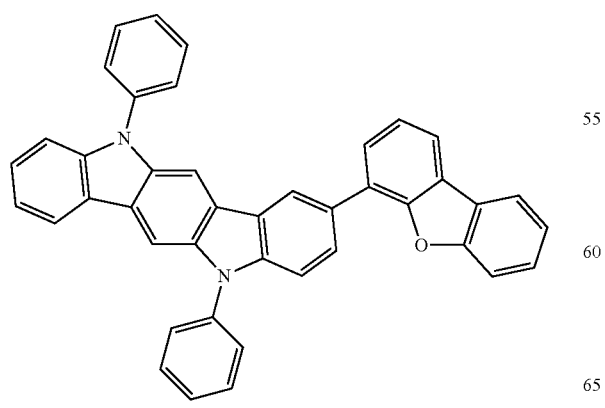
[E-70]
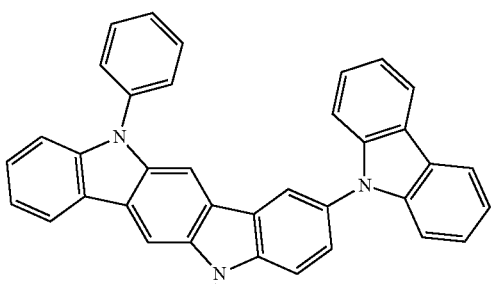
[E-71]
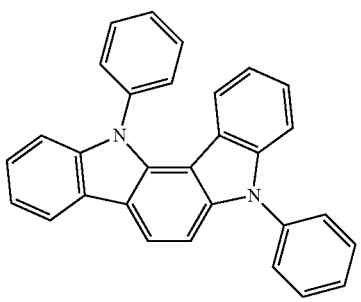
[E-72]
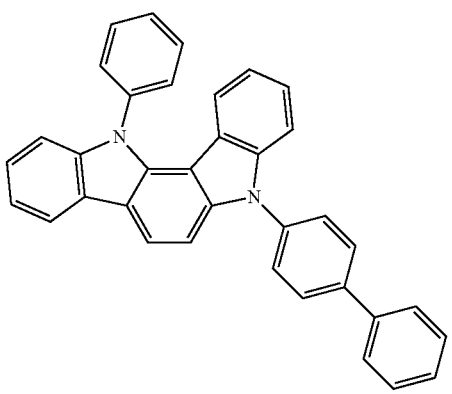
[E-73]
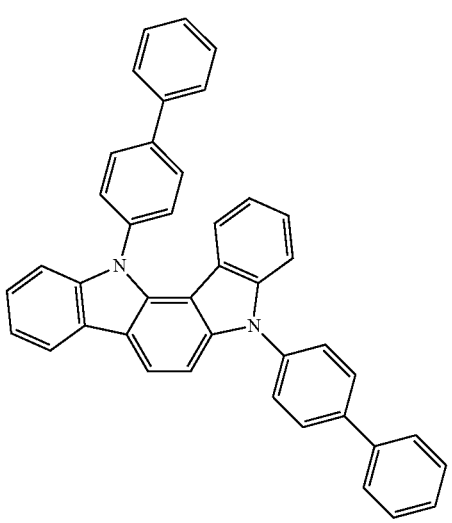

[E-74]
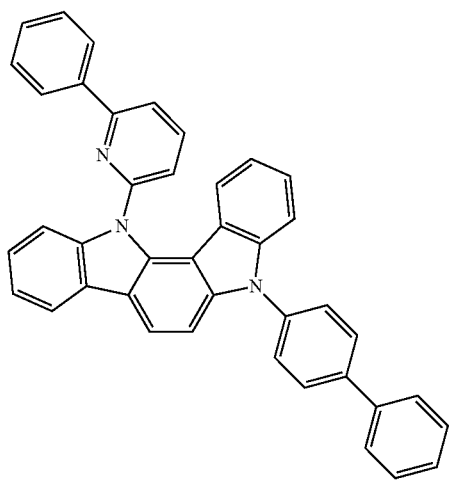
[E-75]
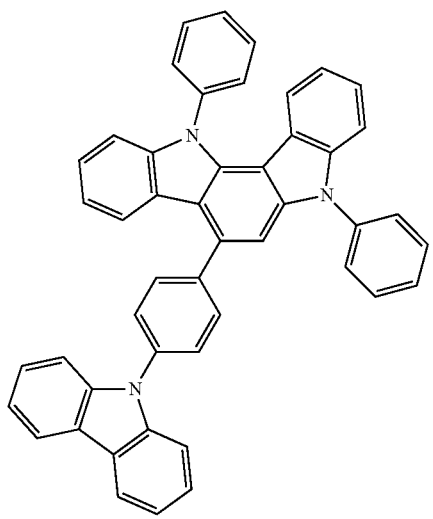
[E-76]
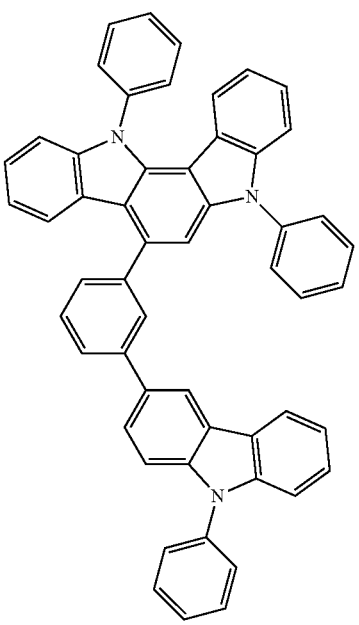
[E-77]
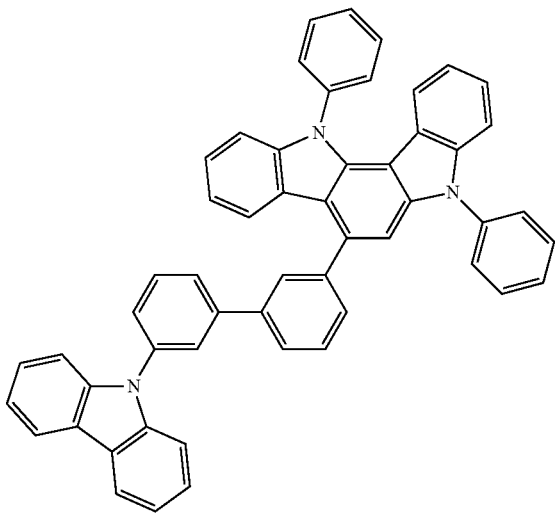
[E-78]
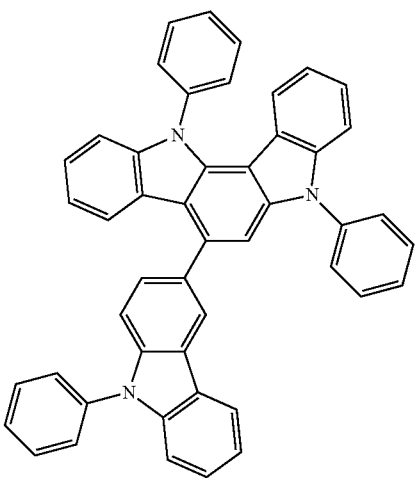
[E-79]

[E-80]
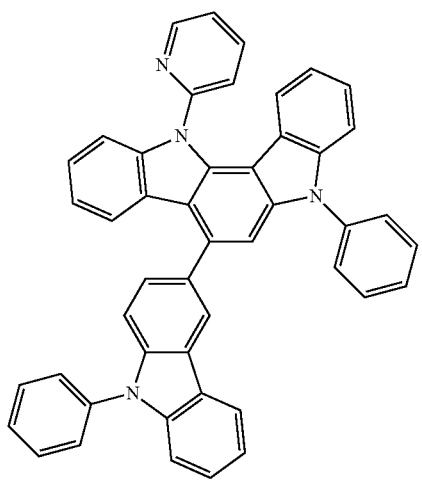
[E-81]
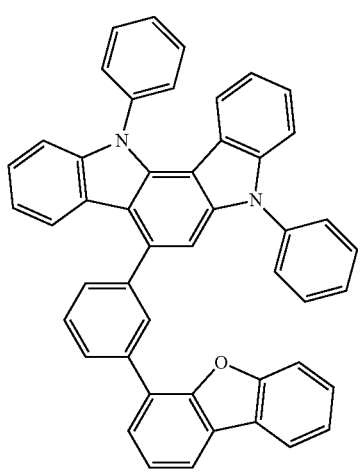
[E-82]
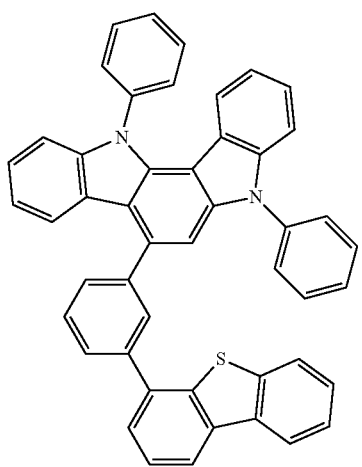
[E-83]
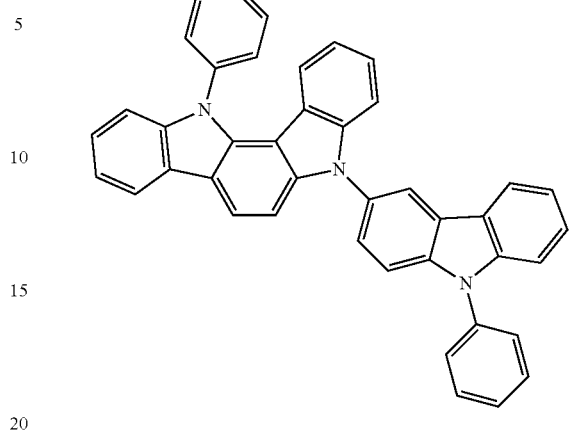
[E-84]
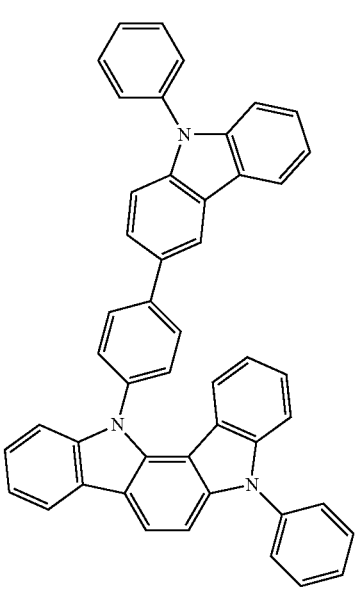
[E-85]
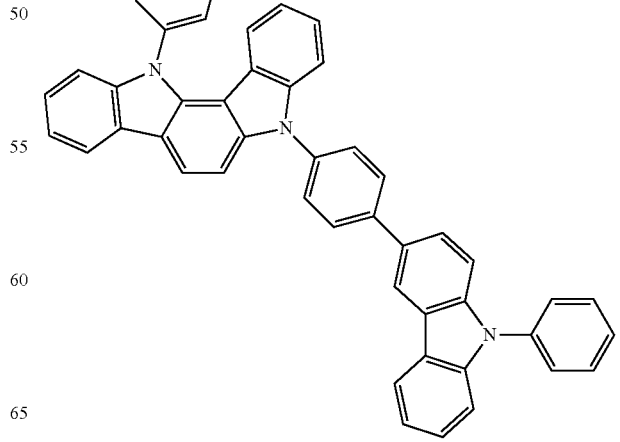

[E-86]
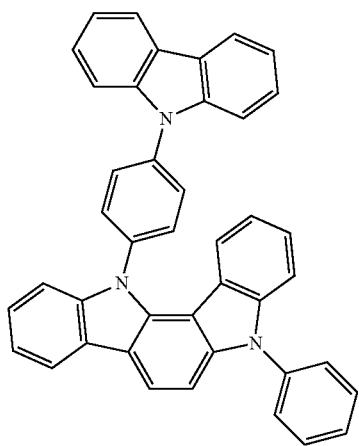
[E-89]
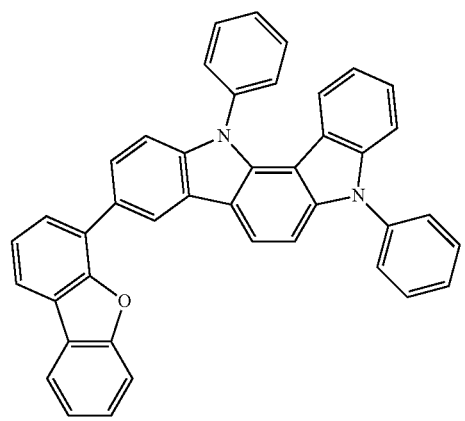
[E-87]
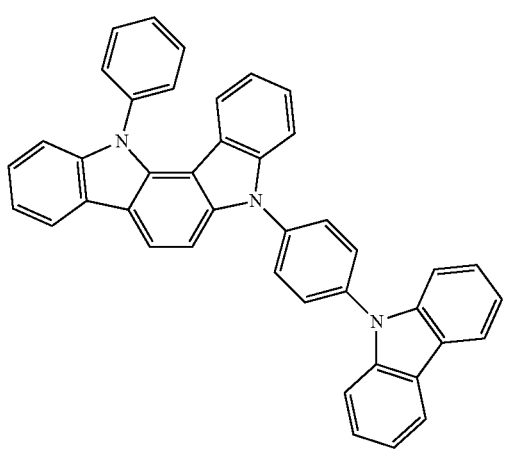
[E-90]
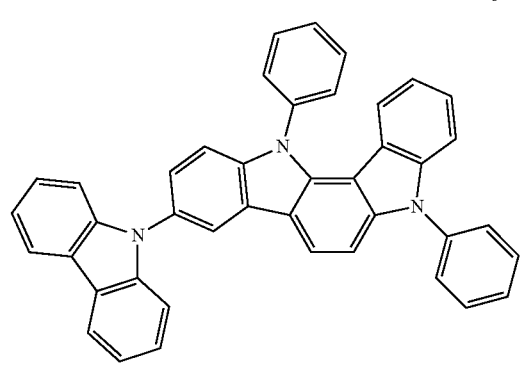
[E-88]
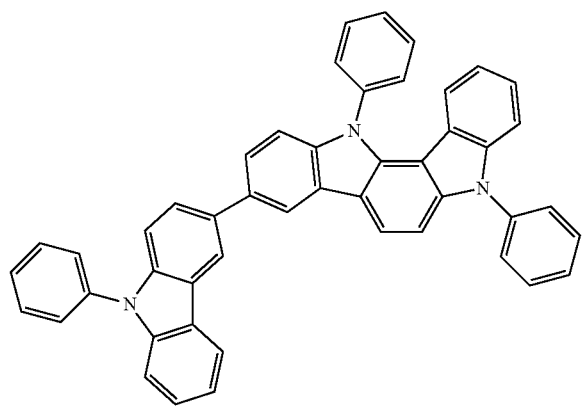
[E-91]
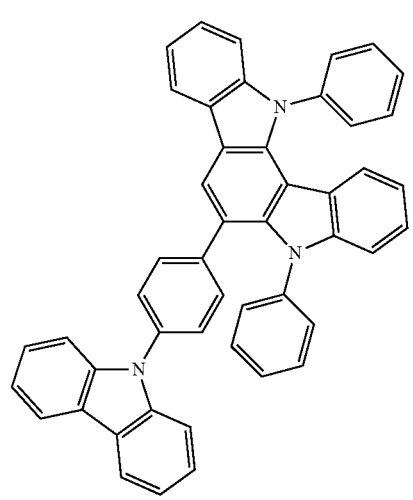

[E-92]
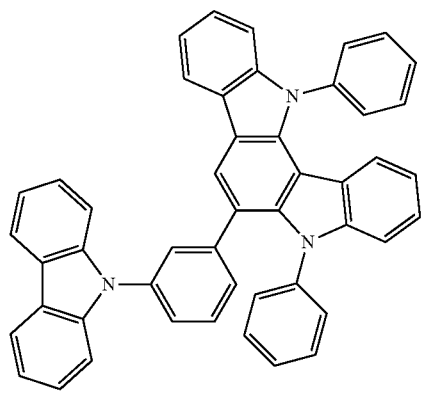
[E-93]
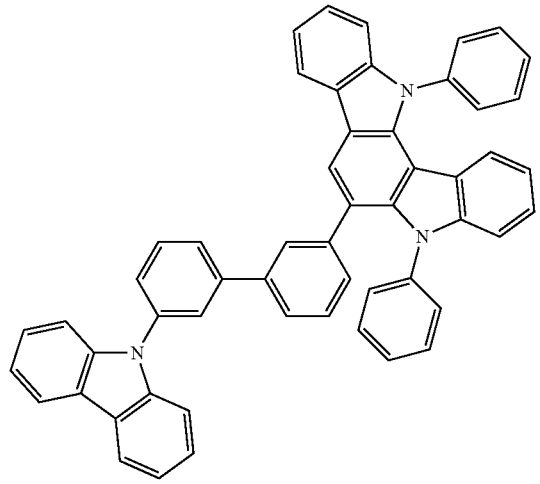
[E-94]
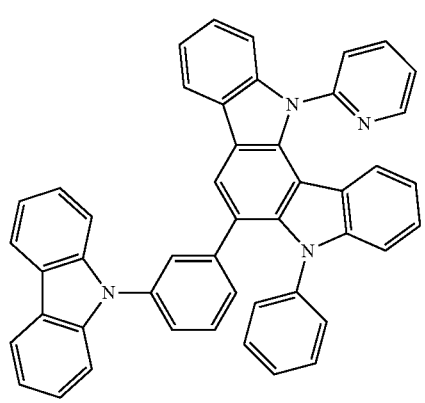
[E-95]
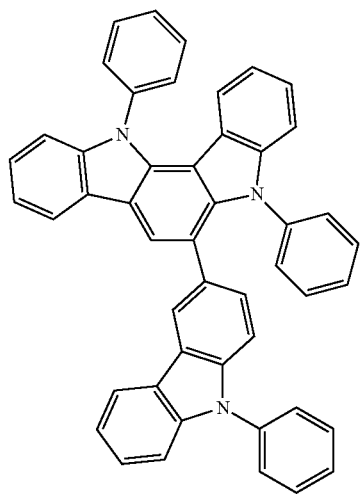
[E-96]
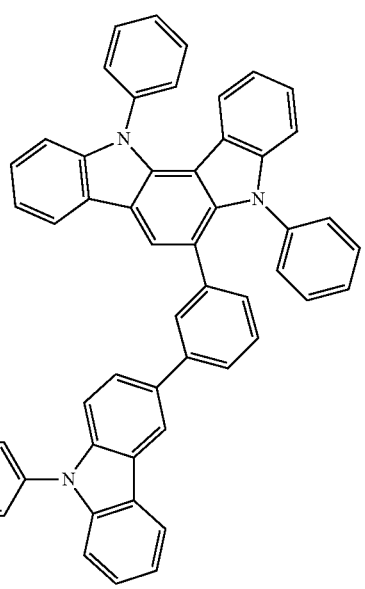
[E-97]
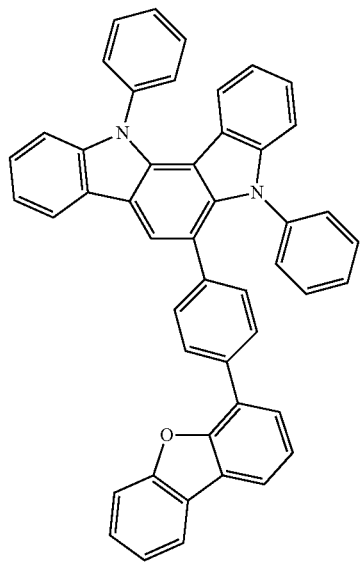

[E-98]

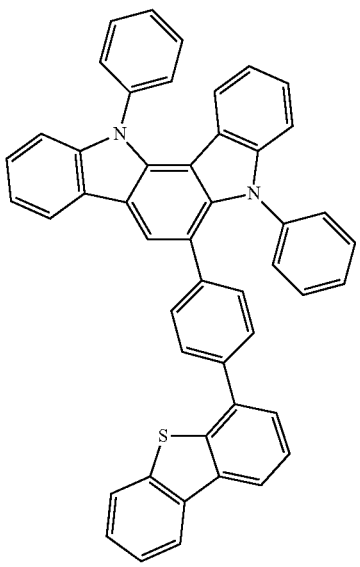

The first compound for an organic optoelectronic device and the second compound for an organic optoelectronic device may variously be combined to prepare various compositions.

A composition according to an example embodiment of the present invention may include a compound represented by Chemical Formula 1-I, 1-II, or 1-III as the first compound for an organic optoelectronic device and a compound represented by Chemical Formula 2-IV as the second compound for an organic optoelectronic device.

In addition, the compound represented by Chemical Formula 1A, Chemical Formula 1B, or Chemical Formula 1C may be included as the first compound for an organic optoelectronic device and compound represented by Chemical Formula 2-IV may be included as the second compound for an organic optoelectronic device.

The $Ar^1$ and $Ar^2$ of Chemical Formula 2-IV may independently be a substituted or unsubstituted phenyl group, a substituted or unsubstituted biphenyl group, a substituted or unsubstituted carbazolyl group, a substituted or unsubstituted dibenzofuranyl group, or a substituted or unsubstituted dibenzothiophenyl group, $L^{a4}$, $L^{a5}$, $L^1$, and $L^2$ may independently be a single bond, or a substituted or unsubstituted phenylene group, and $R^{c4}$, $R^{c5}$, and $R^3$ to $R^6$ may be all hydrogen.

The second compound for an organic optoelectronic device is used with the first compound for an organic optoelectronic device in the light emitting layer and increases charge mobility and stability, and thereby luminous efficiency and life-span characteristics may be improved. In addition, a ratio of the second compound for an organic optoelectronic device and the first compound for an organic optoelectronic device may be adjusted and thereby charge mobility may be controlled.

For example, they may be included in a weight ratio of about 1:9 to 9:1, specifically in a weight ratio of 2:8 to 8:2, 3:7 to 7:3, 4:6 to 6:4, or 5:5, and specifically in a weight ratio of 1:9 to 9:1, 2:8 to 8:2, or 3:7 to 7:3. In one example of the present invention, the first compound for an organic optoelectronic device and the second compound for an organic optoelectronic device may be included at 1:1 to 1:4 or 1:1 to 3:7.

For example, the first compound for an organic optoelectronic device and the second compound for an organic optoelectronic device may be included at 3:7. Within the ranges, efficiency and life-span may be simultaneously improved.

The composition may further include one or more organic compounds in addition to the first compound for an organic optoelectronic device and the second compound for an organic optoelectronic device.

The composition for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectronic device including the composition for an organic optoelectronic device is described.

An organic optoelectronic device according to another embodiment includes an anode and a cathode facing each other and at least one organic layer disposed between the anode and the cathode, wherein the organic layer includes the composition for an organic optoelectronic device.

For example, the organic layer may include a light emitting layer and the light emitting layer may include the composition for an organic optoelectronic device of the present invention.

Specifically, the composition for an organic optoelectronic device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the composition for an organic optoelectronic device.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to an embodiment.

Referring to FIG. 1, an organic optoelectronic diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, LiO$_2$/Al, LiF/Ca, LiF/Al and BaF$_2$/Ca, but is not limited thereto.

The organic layer 105 includes a light emitting layer 130 including the compound for an organic optoelectronic device.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer may further increase hole injection and/or hole mobility and block electrons between the anode 120 and the light emitting layer 130. The hole auxiliary layer may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The composition for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.
(Preparation of Compound for Organic Optoelectronic Device)

The compound as one specific examples of the present invention was synthesized through the following steps.

First Compound for Organic Optoelectronic Device

Synthesis Example 1: Synthesis of Compound A-1

[Reaction Scheme 1]

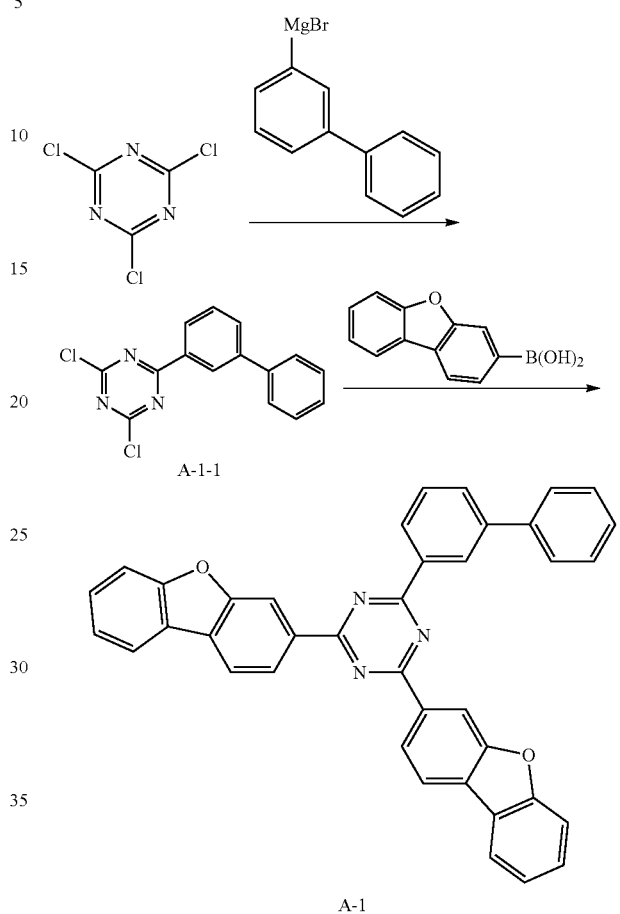

a) Synthesis of Intermediate A-1-1

Cyanuric chloride (15 g, 81.34 mmol) was dissolved in anhydrous tetrahydrofuran (200 mL) in a 500 mL round-bottomed flask, 3-biphenyl magnesium bromide solution (0.5 M tetrahydrofuran, 1 equivalent) was added thereto in a dropwise fashion under a nitrogen atmosphere at 0° C., and the mixture was slowly heated up to room temperature. The mixture was stirred at the same room temperature for 1 hour and poured into ice water (500 mL) to separate layers. An organic layer was separated therefrom and then, treated with anhydrous magnesium sulfate and concentrated. The concentrated residue was recrystallized with tetrahydrofuran and methanol to obtain 17.2 g of Intermediate A-1-1.

b) Synthesis of Compound A-1

Intermediate A-1-1 (17.2 g, 56.9 mmol) was added to tetrahydrofuran (200 mL) and distilled water (100 mL) in a 500 mL round-bottomed flask, 2 equivalents of dibenzofuran-3-boronic acid (Cas No.: 395087-89-5), 0.03 equivalents of tetrakistriphenylphosphine palladium, and 2 equivalents of potassium carbonate were added thereto, and the obtained mixture was heated and refluxed under a nitrogen atmosphere. After 18 hours, the reaction solution was cooled down, and a solid precipitated therein was filtered and washed with 500 mL of water. The solid was recrystallized with monochlorobenzene (500 mL) to obtain 12.87 g of Compound A-1.

LC/MS calculated for: C39H23N3O2. Exact Mass: 565.1790 found for: 566.18 [M+H].

Synthesis Example 2: Synthesis of Compound A-2

[Reaction Scheme 2]

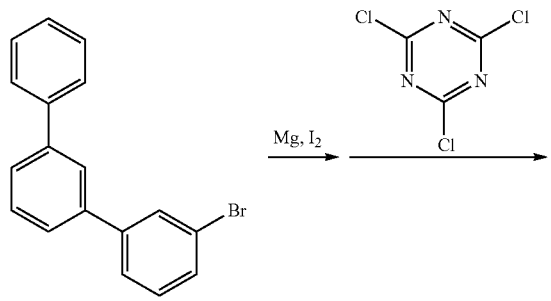

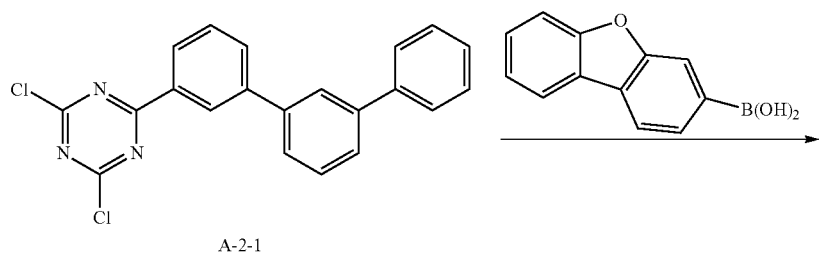

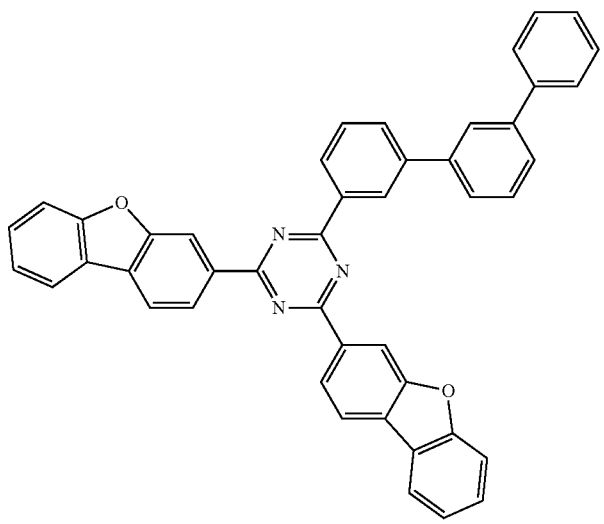

a) Synthesis of Intermediate A-2-1

Magnesium (7.86 g, 323 mmol) and iodine (1.64 g, 6.46 mmol) were added to 0.1 L of tetrahydrofuran (THF) under a nitrogen environment, the mixture was stirred for 30 minutes, and 3-bromo-tert-phenyl (100 g, 323 mmol) dissolved in 0.3 L of THF was slowly added thereto in a dropwise fashion at 0° C. for 30 minutes. The mixed solution was slowly added in a dropwise fashion to cyanuric chloride (64.5 g, 350 mmol) dissolved in 0.5 L of THF at 0° C. for 30 minutes. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate A-2-1 (85.5 g, 70%).

b) Synthesis of Compound A-2

Intermediate A-2-1 was used according to the same method as b) of Synthesis Example 1 to synthesize Compound A-2.

LC/MS calculated for: C45H27N3O2. Exact Mass: 641.2103 found for 642.21 [M+H].

Synthesis Example 3: Synthesis of Compound A-5

[Reaction Scheme 3]

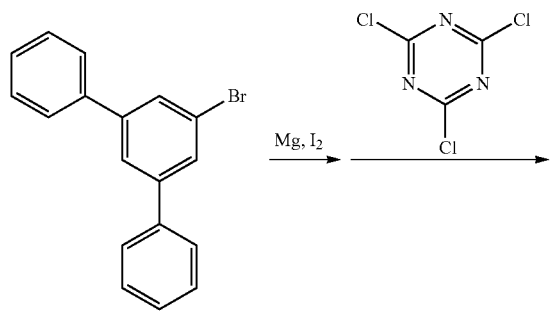

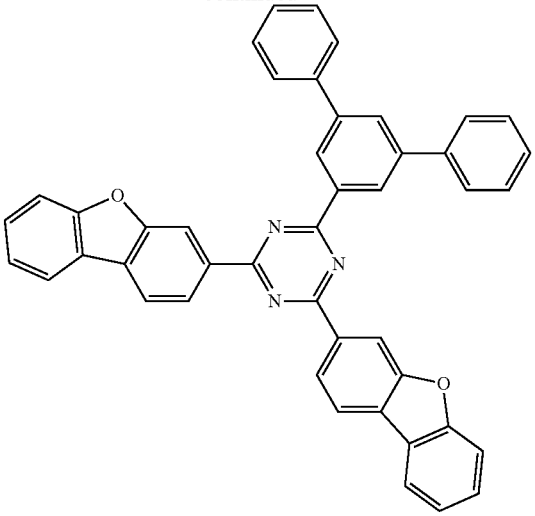

A-5

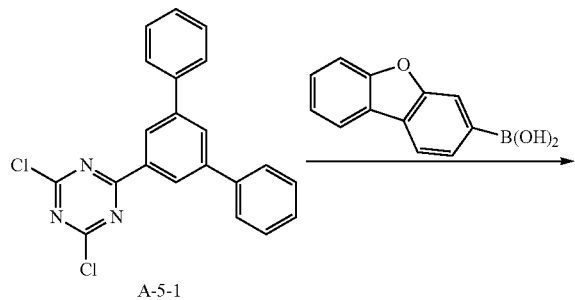

A-5-1 a) Synthesis of Intermediate A-5-1

Magnesium (7.86 g, 323 mmol) and iodine (1.64 g, 6.46 mmol) were added to 0.1 L of tetrahydrofuran (THF) under a nitrogen environment, the mixture was stirred for 30 minutes, 1-bromo-3,5-diphenylbenzene (100 g, 323 mmol) dissolved in 0.3 L of THF was slowly added thereto in a dropwise fashion at 0° C. for 30 minutes. This mixed solution was slowly added in a dropwise fashion to cyanuric chloride (64.5 g, mmol) dissolved in 0.5 L of THF at 0° C. for 30 minutes. When the reaction was complete, water was added to the reaction solution, the mixture was extracted with dichloromethane (DCM), and after removing moisture with anhydrous $MgSO_4$, the resultant was filtered and concentrated under a reduced pressure. This obtained residue was separated and purified through flash column chromatography to obtain Intermediate A-5-1 (79.4 g, 65%).

b) Synthesis of Compound A-5

Compound A-5 was synthesized according to the same method as b) of Synthesis Example 1 by using Intermediate A-5-1.

LC/MS calculated for: C45H27N3O2. Exact Mass: 641.2103 found for 642.21 [M+H].

Synthesis Example 4: Synthesis of Compound A-15

[Reaction Scheme 4]

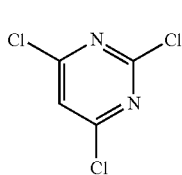

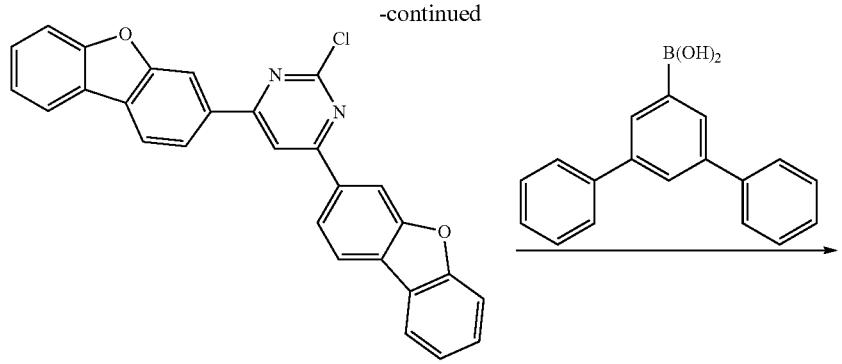

A-15-1

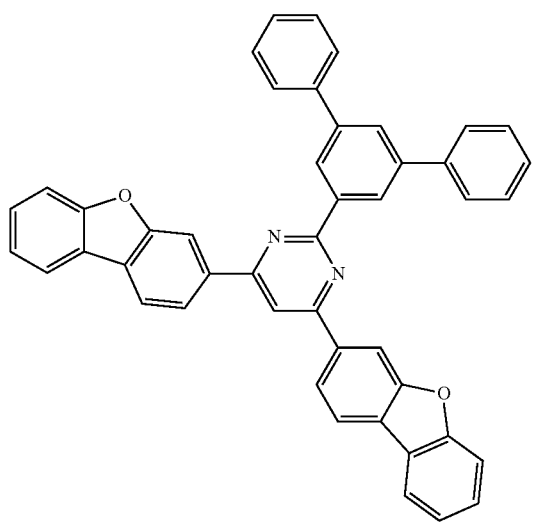

A-15 a) Synthesis of Intermediate A-15-1

2,4,6-trichloropyrimidine (18.3 g, 100 mmol) was added to tetrahydrofuran (200 mL) and distilled water (100 mL) in a 500 mL round-bottomed flask, 1.9 equivalents of dibenzofuran-3-boronic acid (Cas No.: 395087-89-5), 0.03 equivalents of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain Intermediate A-15-1 (26.8 g, 60%).

b) Synthesis of Compound A-15

Compound A-15 was synthesized according to the same method as b) of Synthesis Example 1 by using Intermediate A-15-1 and 1.1 equivalents of 3,5-diphenylbenzeneboronic acid.

LC/MS calculated for: C46H28N2O2. Exact Mass: 640.2151 found for 641.21 [M+H].

Synthesis Example 5: Synthesis of Compound A-21

[Reaction Scheme 5]

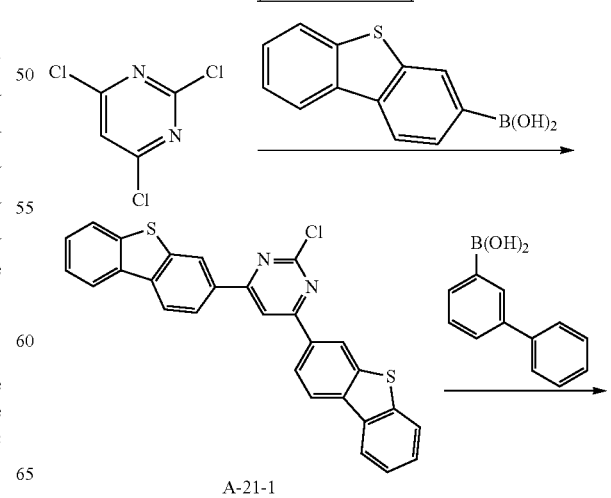

A-21-1

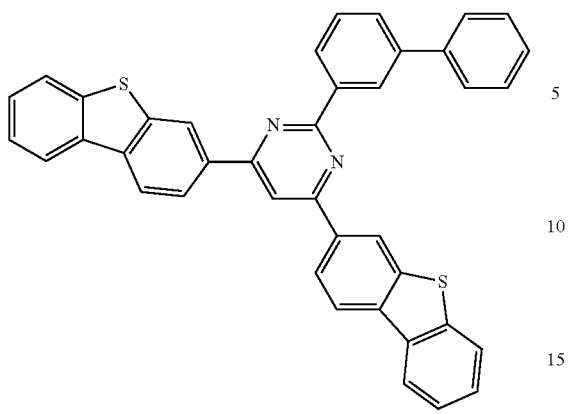

A-21

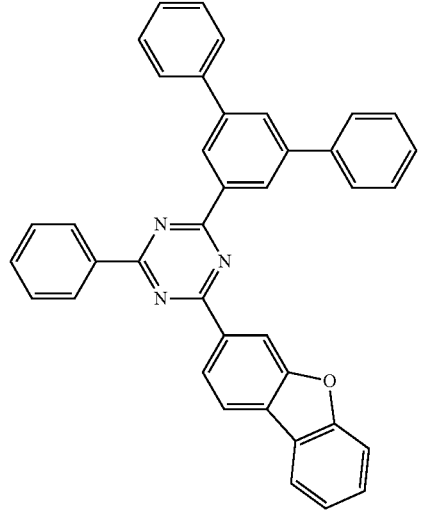

B-1 a) Synthesis of Intermediate A-21-1

Intermediate A-21-1 was synthesized according to the same method as a) of Synthesis Example 3 by using dibenzothiophene-3-boronic acid (Cas No. 108847-24-1) instead of dibenzofuran-3-boronic acid (Cas No.: 395087-89-5).

b) Synthesis of Compound A-21

Compound A-21 was synthesized according to the same method as b) of Synthesis Example 1 by using Intermediate A-21-1 and 1.1 equivalents of biphenyl-3-boronic acid.

LC/MS calculated for: C40H24N2S2. Exact Mass: 596.1381 found for 597.14 [M+H].

Synthesis Example 6: Synthesis of Compound B-1

[Reaction Scheme 6]

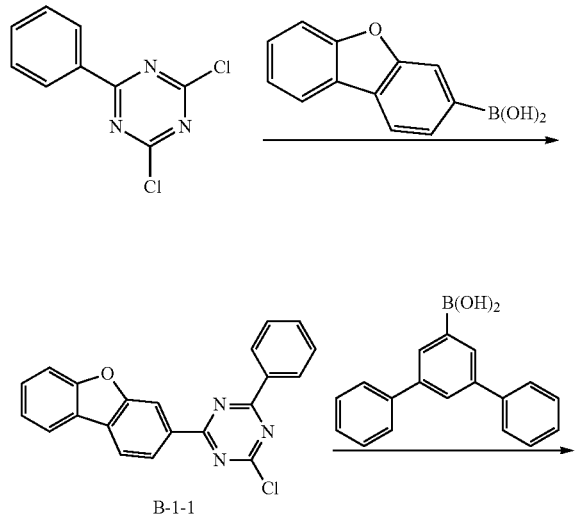

a) Synthesis of Intermediate B-1-1

2,4-dichloro-6-phenyltriazine (22.6 g, 100 mmol) was added to tetrahydrofuran (100 mL), toluene (100 mL), and distilled water (100 mL) in a 500 mL round-bottomed flask, 0.9 equivalents of dibenzofuran-3-boronic acid (CAS No.: 395087-89-5), 0.03 equivalents of tetrakistriphenylphosphine palladium, and 2 equivalents of potassium carbonate were added thereto, and the mixture was heated and refluxed under a nitrogen environment. After 6 hours, the reaction solution was cooled down, and an organic layer obtained by removing an aqueous layer was dried under a reduced pressure. A solid obtained therefrom was washed with water and hexane and recrystallized with toluene (200 mL) to obtain Intermediate B-1-1 (21.4 g, 60%).

b) Synthesis of Compound B-1

Intermediate B-1-1 (56.9 mmol) was added to tetrahydrofuran (200 mL) and distilled water (100 mL) in a 500 mL round-bottomed flask, 1.1 equivalents of 3,5-diphenylbenzeneboronic acid (Cas No.: 128388-54-5), 0.03 equivalents of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain Compound B-1.

LC/MS calculated for: C39H25N3O. Exact Mass: 555.1998 found for 556.21 [M+H].

Synthesis Example 7: Synthesis of Compound B-7

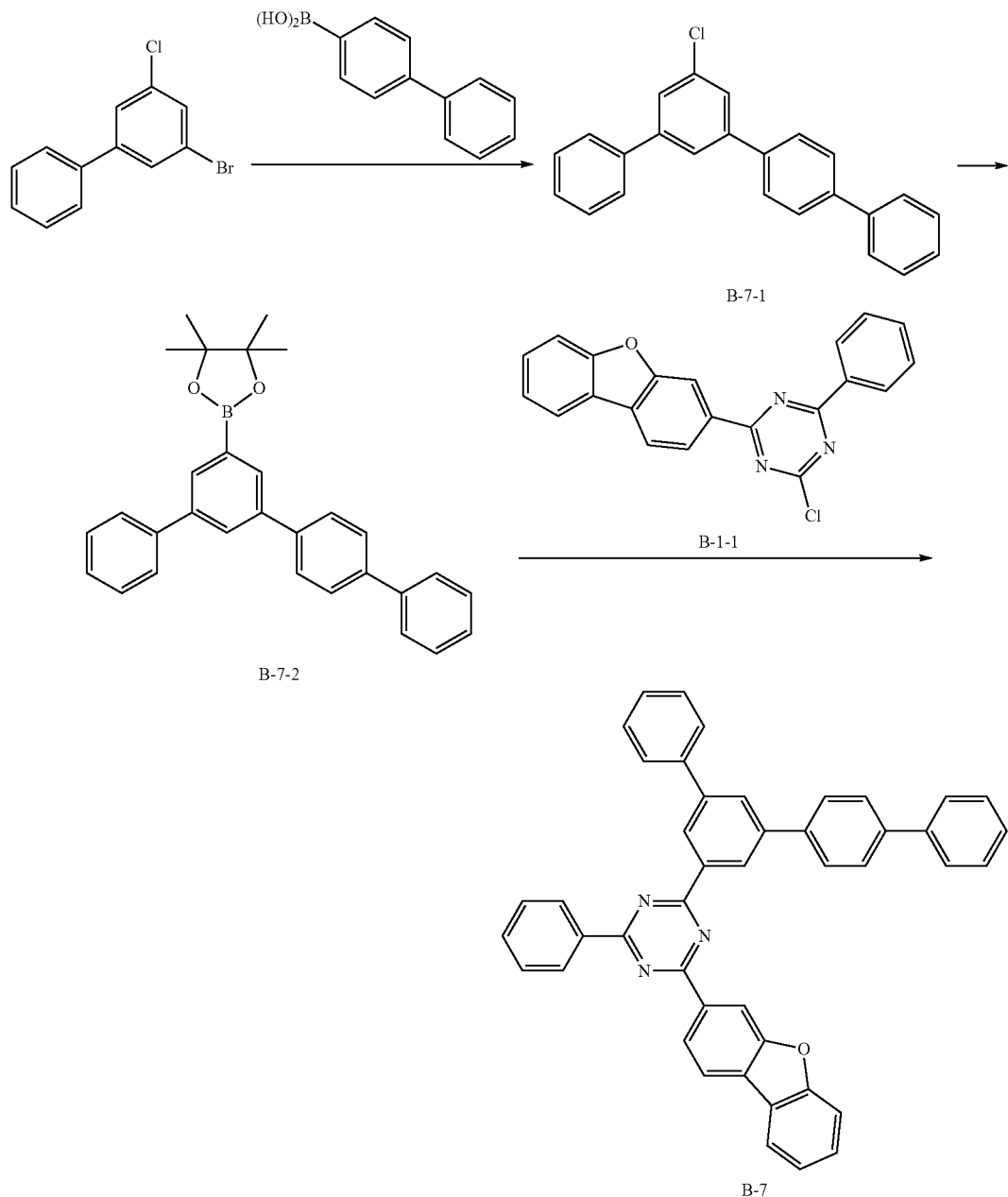

a) Synthesis of Intermediate B-7-1

Intermediate B-7-1 was synthesized according to the same method as b) of Synthesis Example 1 by using 1-bromo-3-chloro-5-phenylbenzene and 1.1 equivalents of biphenyl-4-boronic acid. Herein, a product was purified through flash column with hexane instead of the recrystallization.

b) Synthesis of Intermediate B-7-2

Intermediate B-7-1 (30 g, 88.02 mmol) was added to 250 mL of DMF in a 500 mL round-bottomed flask, 0.05 equivalents of dichlorodiphenylphosphinoferrocene palladium, 1.2 equivalents of bispinacolato diboron, and 2 equivalents of potassium acetate were added thereto, and the mixture was heated and refluxed under a nitrogen atmosphere for 18 hours. The reaction solution was cooled down and then, dropped in 1 L of water to obtain a solid. The solid was dissolved in boiling toluene to treat with activated carbon and then, filtered through silica gel and concentrated. The concentrated solid was stirred with a small amount of hexane and then, filtered to obtain Intermediate B-7-2 (28.5 g, 70%).

c) Synthesis of Compound B-7

Compound B-7 was synthesized according to the same method as b) of Synthesis Example 6 by using Intermediate B-7-2 and Intermediate B-1-1 in each amount of 1.0 equivalent.

LC/MS calculated for: C45H29N3O. Exact Mass: 627.2311 found for 628.22 [M+H].

Synthesis Example 8: Synthesis of Compound B-9

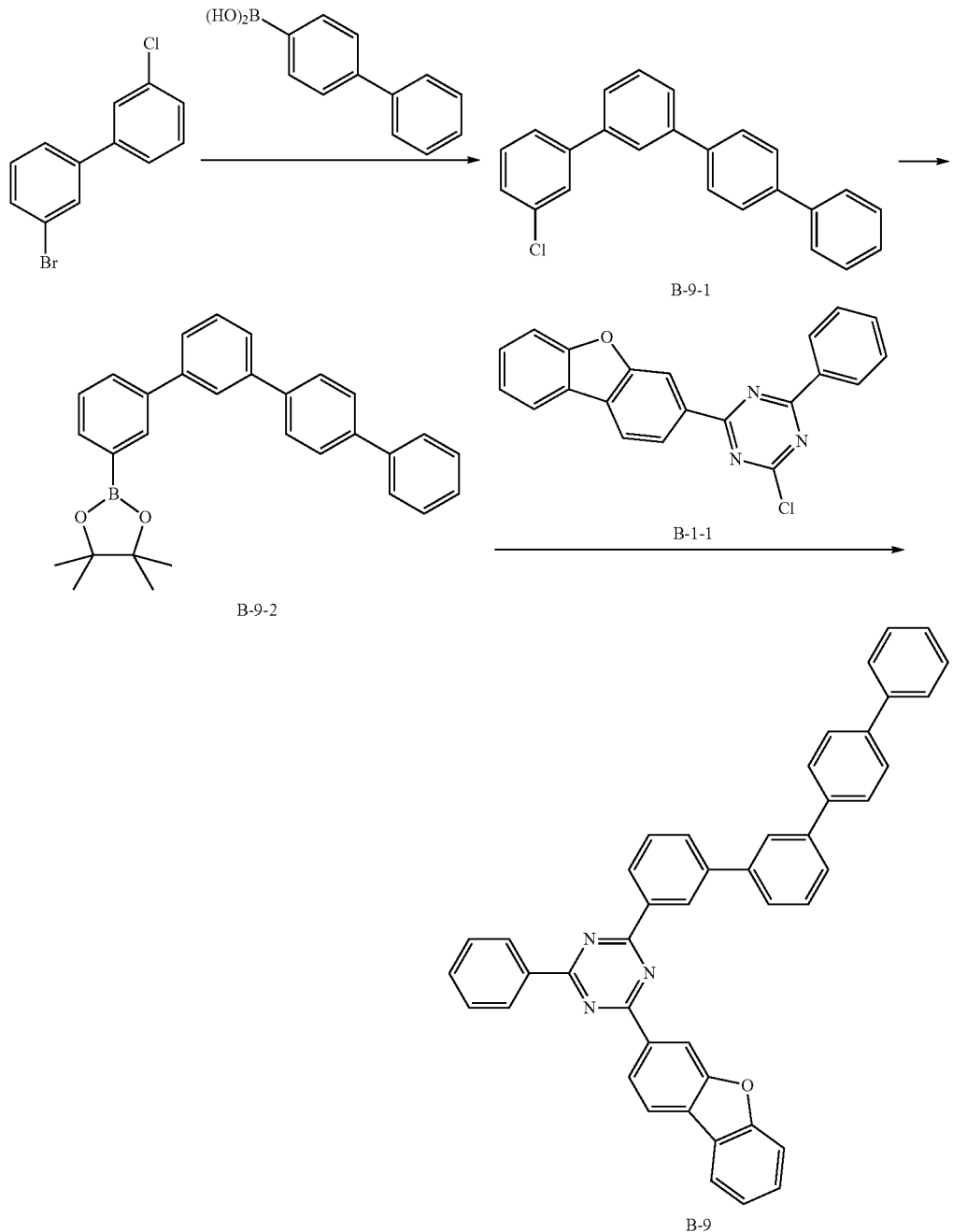

a) Synthesis of Intermediate B-9-1

Intermediate B-9-1 was synthesized according to the same method as b) of Synthesis Example 6 by using 1 equivalent of 3-bromo-3'-chloro-1,1'-biphenyl (Cas No.: 844856-42-4) and 1.1 equivalents of biphenyl-4-boronic acid. Herein, a product therefrom was purified through flash column with hexane instead of the recrystallization.

b) Synthesis of Intermediate B-9-2

Intermediate B-9-2 was synthesized under the same condition as b) of Synthesis Example 7 by using Intermediate B-9-1.

c) Synthesis of Compound B-9

Compound B-9 was synthesized according to the same method as b) of Synthesis Example 6 by using Intermediate B-9-2 and Intermediate B-1-1 in each amount of 1.0 equivalent.

LC/MS calculated for: C45H29N3O. Exact Mass: 627.2311 found for 628.22 [M+H].

Synthesis Example 9: Synthesis of Compound B-11

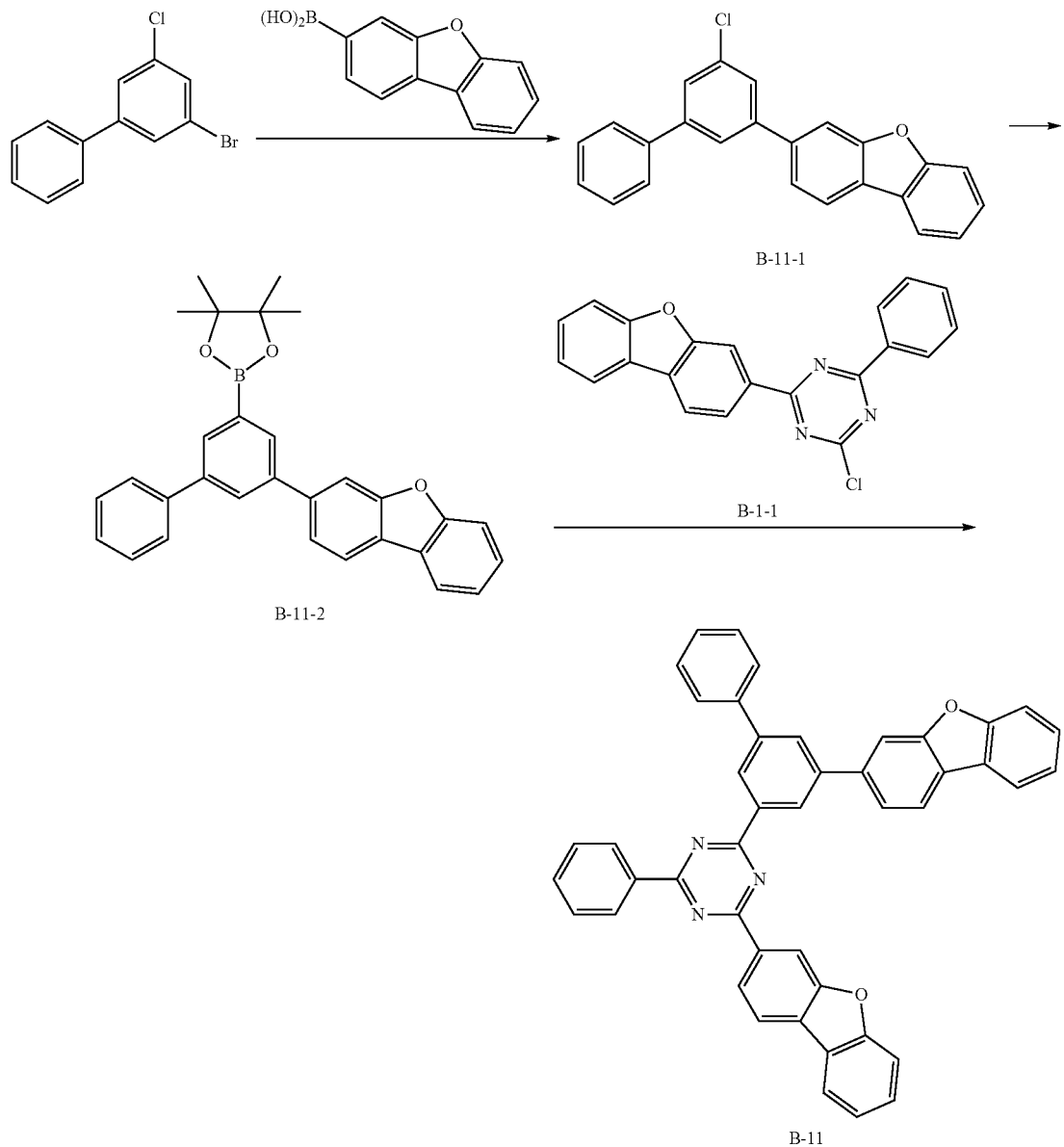

a) Synthesis of Intermediate B-11-1

Intermediate B-11-1 was synthesized according to the same method as b) of Synthesis Example 4 by using 1 equivalent of 1-bromo-3-chloro-5-phenylbenzene and 1.1 equivalents of dibenzofuran-3-boronic acid.

b) Synthesis of Intermediate B-11-2

Intermediate B-11-2 was synthesized by using Intermediate B-11-1 and performing a reaction under the same reaction as b) of Synthesis Example 6.

c) Synthesis of Compound B-11

Compound B-11 was synthesized according to the same method as b) of the Synthesis Example 6 by using Intermediate B-11-2 and Intermediate B-1-1 in each amount of 1.0 equivalent.

LC/MS calculated for: C45H27N3O2. Exact Mass: 641.2103 found for 642.22 [M+H].

Synthesis Example 10: Synthesis of Compound B-13

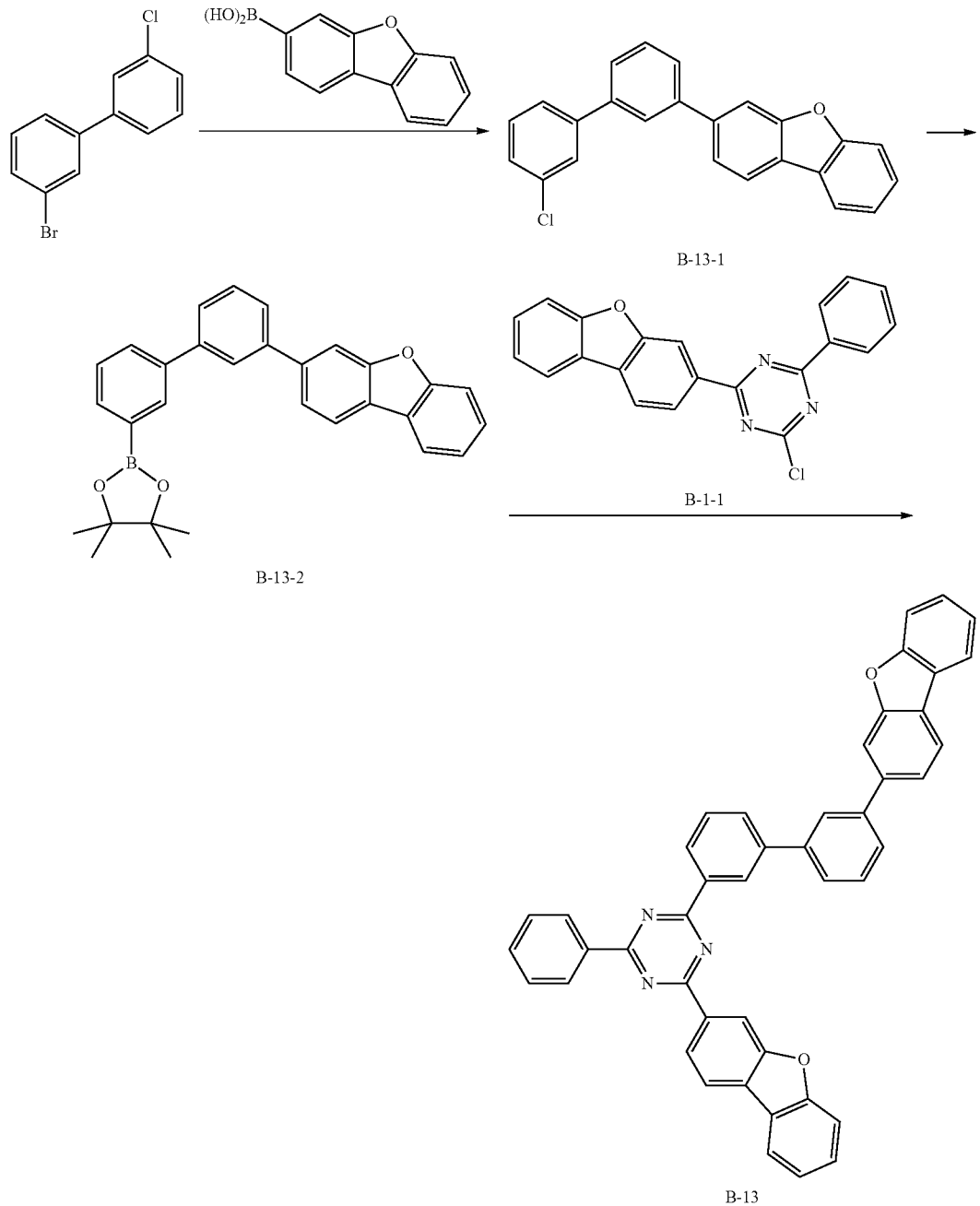

a) Synthesis of Intermediate B-13-1

Intermediate B-13-1 was synthesized according to the same method as b) of Synthesis Example 6 by using 1 equivalent of 3-bromo-3'-chloro-1,1'-biphenyl (Cas No.: 844856-42-4) and 1.1 equivalents of dibenzofuran-3-boronic acid.

b) Synthesis of Intermediate B-13-2

Intermediate B-13-2 was synthesized by using Intermediate B-13-1 and performing a reaction under the same condition as b) of Synthesis Example 7.

c) Synthesis of Compound B-13

Compound B-13 was synthesized according to the same method as b) of Synthesis Example 6 by using Intermediate B-13-2 and Intermediate B-1-1 in each amount of 1.0 equivalent.

LC/MS calculated for: $C_{45}H_{27}N_3O_2$. Exact Mass: 641.2103 found for 642.22 [M+H].

Synthesis Example 11: Synthesis of Compound B-14
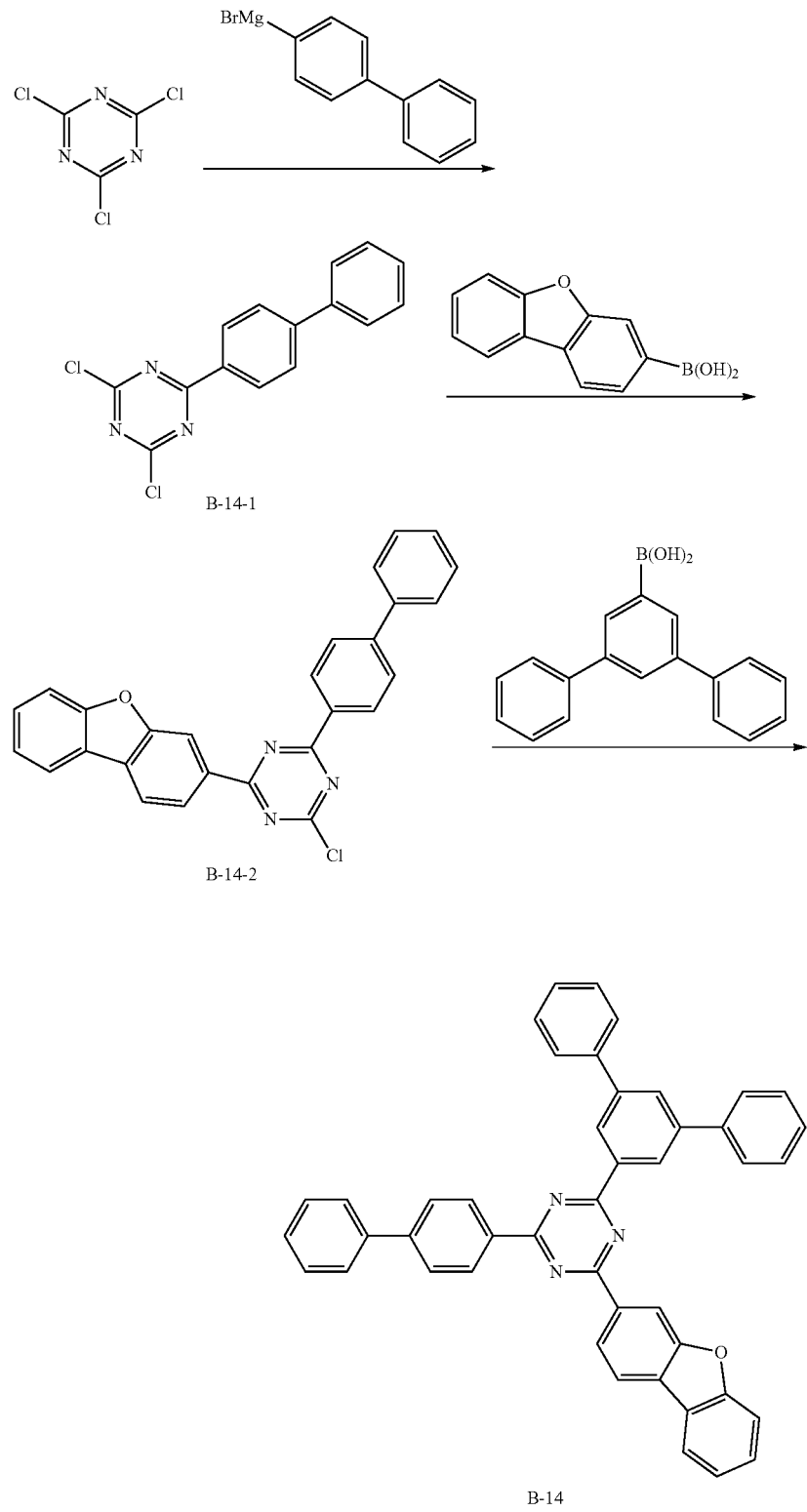

a) Synthesis of Intermediate B-14-1

Cyanuric chloride (15 g, 81.34 mmol) was dissolved in anhydrous tetrahydrofuran (200 mL) in a 500 mL round-bottomed flask, 1 equivalent of a 4-biphenyl magnesium bromide solution (0.5 M tetrahydrofuran) was added thereto in a dropwise fashion at 0° C. under an nitrogen atmosphere, and the mixture was slowly heated up to room temperature. The mixture was stirred at the same room temperature for 1 hour, and 500 mL of ice water was added thereto to separate layers. An organic layer was separated therefrom and then, treated with anhydrous magnesium sulfate and concentrated. The concentrated residue was recrystallized with tetrahydrofuran and methanol to obtain Intermediate B-14-1 (17.2 g).

b) Synthesis of Intermediate B-14-2

Intermediate B-14-2 was synthesized according to the same method as a) of Synthesis Example 6 by using Intermediate B-14-1.

c) Synthesis of Compound B-14

Compound B-14 was synthesized according to the same method as b) of Synthesis Example 6 by using Intermediate B-14-2 and 1.1 equivalents of 3,5-diphenylbenzeneboronic acid.

LC/MS calculated for: C45H29N3O. Exact Mass: 627.2311 found for 628.24 [M+H].

Synthesis Example 12: Synthesis of Compound B-16

[Reaction Scheme 12]

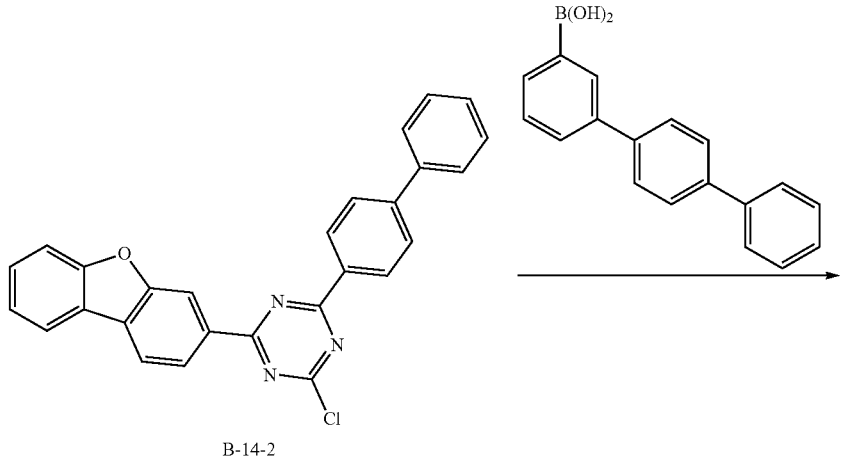

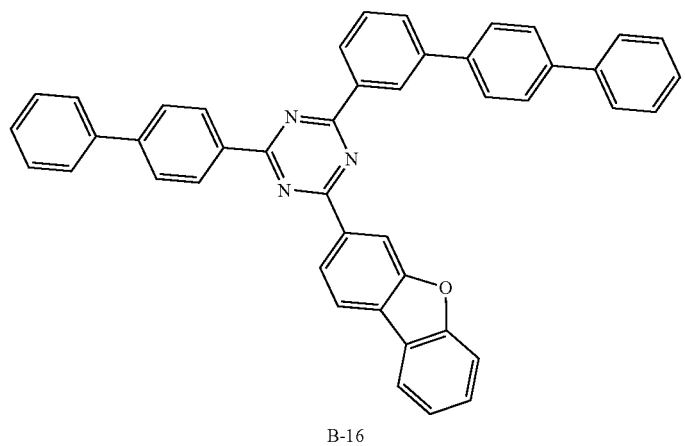

Compound B-16 was synthesized according to the same method as b) of Synthesis Example 6 by using Intermediate B-14-2 and 1.1 equivalents of B-[1,1':4',1''-terphenyl]-3-ylboronic acid.

LC/MS calculated for: C45H29N3O. Exact Mass: 627.2311 found for 628.24 [M+H].

Synthesis Example 13: Synthesis of Compound B-53
[Reaction Scheme 13]
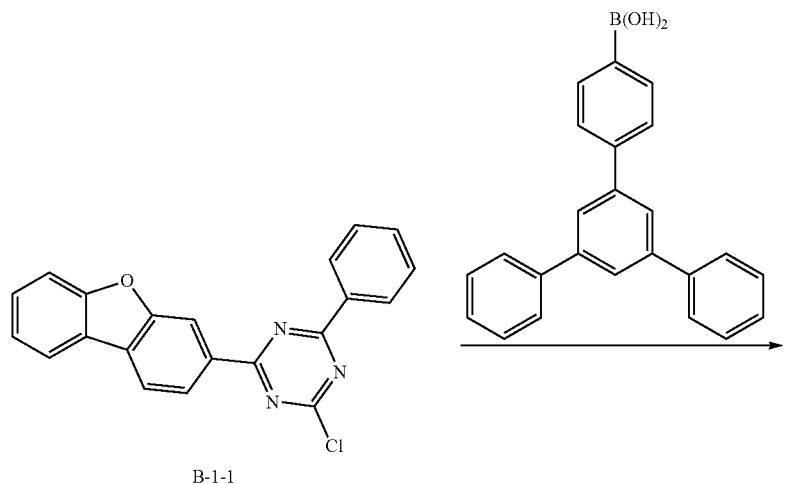
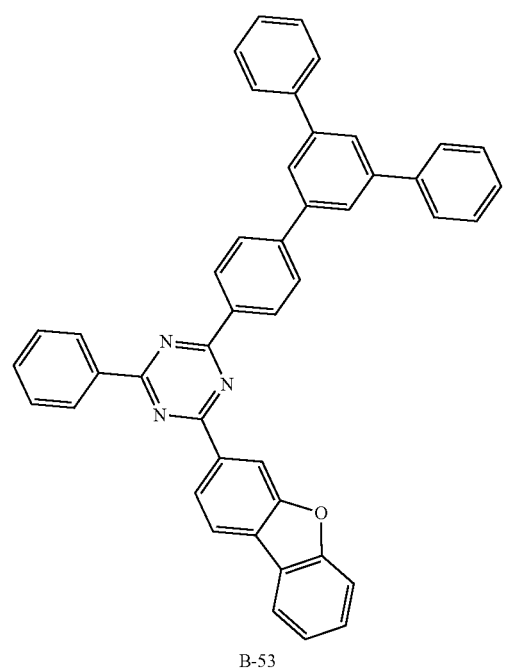
Compound B-53 was synthesized according to the same method as b) of Synthesis Example 6 by using Intermediate B-1-1 and, 1.1 equivalents of (5'-phenyl[1,1':3',1''-terphenyl]-4-yl)-boronic acid (Cas No.: 491612-72-7). LC/MS calculated for: C45H29N3O. Exact Mass: 627.2311 found for 628.24 [M+H].

Synthesis Example 14: Synthesis of Compound B-70

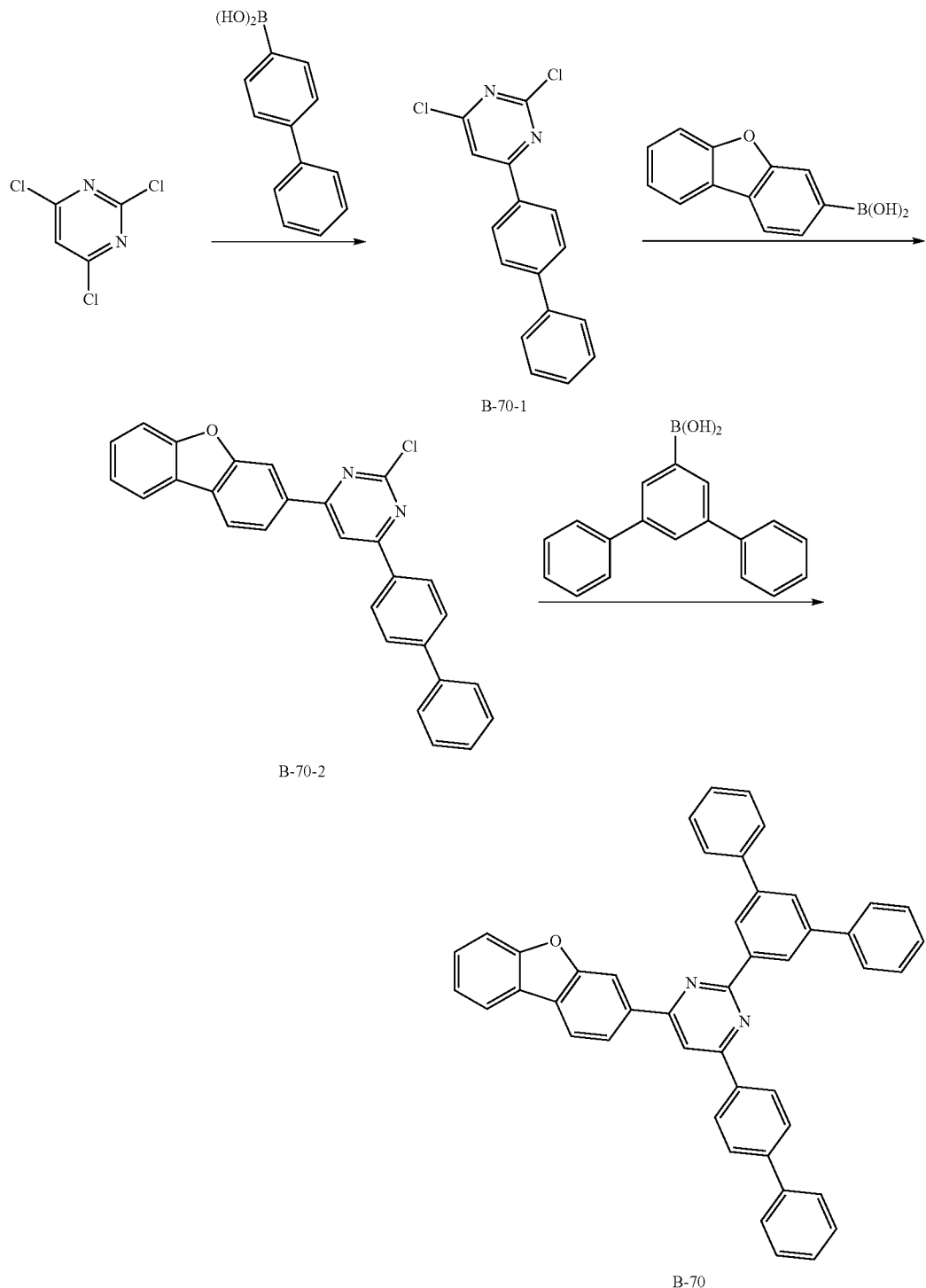

a) Synthesis of Intermediate B-70-1

2,4,6-trichloropyrimidine (18.3 g, 100 mmol) was added to tetrahydrofuran (100 mL), toluene (100 mL), and distilled water (100 mL) in a 500 mL round-bottomed flask, 0.9 equivalents of biphenyl-4-boronic acid, 0.03 equivalents of tetrakistriphenylphosphine palladium, and 2 equivalents of potassium carbonate were added thereto, and the mixture was heated and refluxed under a nitrogen atmosphere. After 8 hours, the reaction solution was cooled down, and an organic layer separated after removing an aqueous layer was dried to obtain a solid. The solid was treated through column chromatography to synthesize Intermediate B-70-1 (21.1 g, 70%).

b) Synthesis of Intermediate B-70-2

Intermediate B-70-2 was synthesized according to the same method as a) of Synthesis Example 6 by using Intermediate B-70-1.

c) Synthesis of Compound B-70

Compound B-70 was synthesized according to the same method as b) of Synthesis Example 6 by using Intermediate B-70-2 and 1.1 equivalents of 3,5-diphenylbenzeneboronic acid.

LC/MS calculated for: C46H30N2O. Exact Mass: 626.2358 found for 627.24 [M+H].

Synthesis Example 15: Synthesis of Compound B-78

[Reaction Scheme 15]

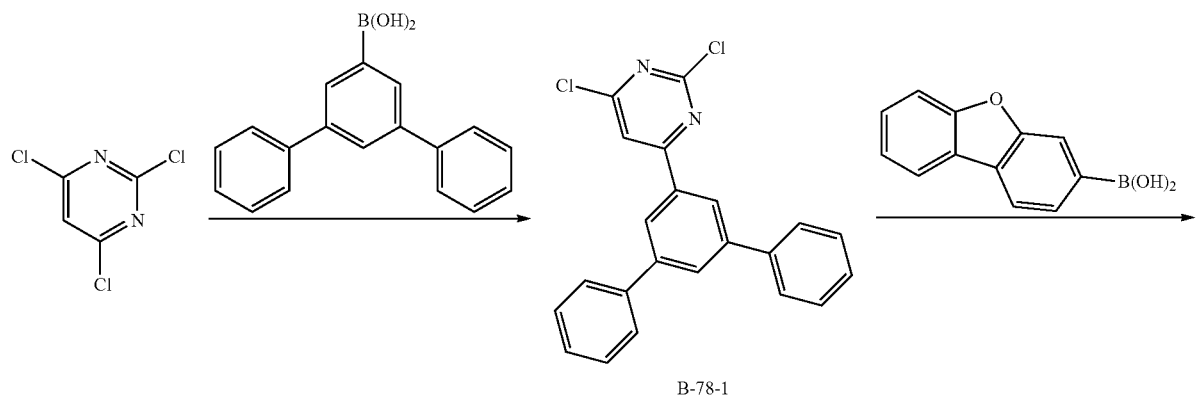

B-78-1

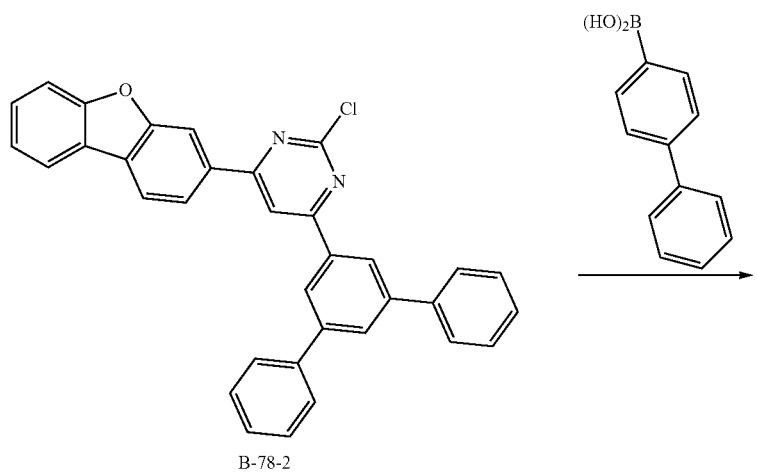

B-78-2

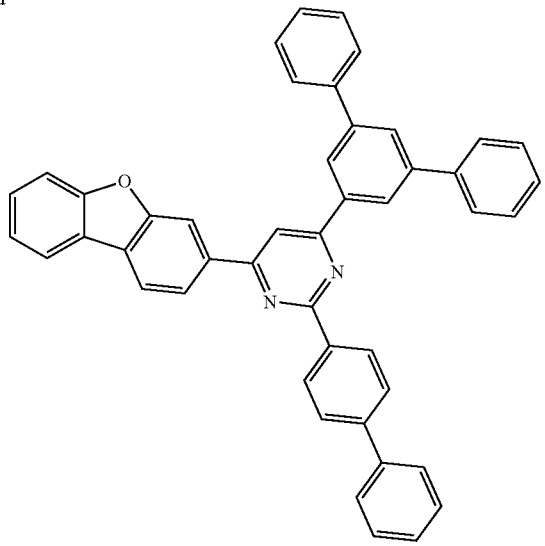

B-78 a) Synthesis of Intermediate B-78-1

Intermediate B-78-1 was synthesized according to the same method as a) of Synthesis Example 14 by using 3,5-diphenylbenzeneboronic acid instead of biphenyl-4-boronic acid.

b) Synthesis of Intermediate B-78-2

Intermediate B-78-2 was synthesized according to the same method as a) of Synthesis Example 6 by using Intermediate B-78-1.

c) Synthesis of Compound B-78

Compound B-78 was synthesized according to the same method as b) of Synthesis Example 6 by using Intermediate B-78-2 and 1.1 equivalents of biphenyl-4-boronic acid.

LC/MS calculated for: C46H30N2O. Exact Mass: 626.2358 found for 627.24 [M+H].

Synthesis Example 16: Synthesis of Compound C-1

[Reaction Scheme 16]

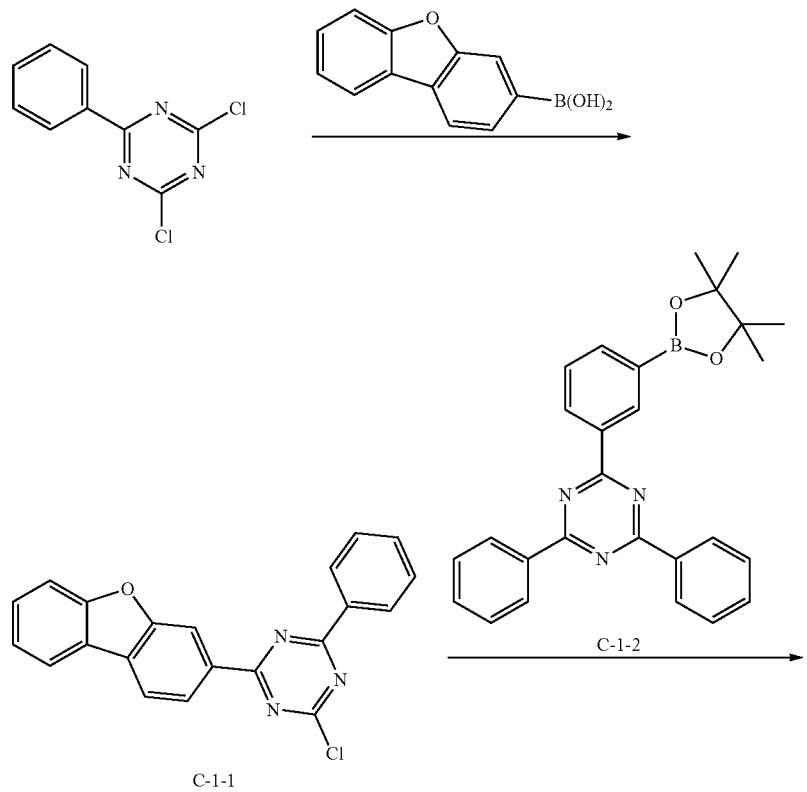

-continued

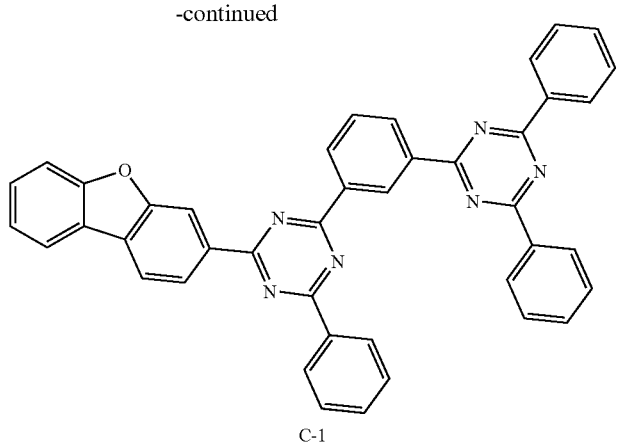

C-1 a) Synthesis of Intermediate C-1-1

2,4-dichloro-6-phenyltriazine (22.6 g, 100 mmol) was added to tetrahydrofuran (100 mL), toluene (100 mL), and distilled water (100 mL) in a 500 mL round-bottomed flask, 0.9 equivalents of dibenzofuran-3-boronic acid, 0.03 equivalents of tetrakistriphenylphosphine palladium, and 2 equivalents of potassium carbonate were added thereto, and the mixture was heated and refluxed under a nitrogen atmosphere. After 6 hours, the reaction solution was cooled down, and an organic layer separated after removing an aqueous layer was dried under a reduced pressure. The solid was washed with water and hexane and recrystallized with toluene (200 mL) to obtain Intermediate C-1-1 (21.4 g, 60%).

b) Synthesis of Compound C-1

Intermediate C-1-1 (20 g, 55.9 mmol) was added to 200 mL of tetrahydrofuran and 100 mL of distilled water in a 500 mL round-bottomed flask, 1.1 equivalents of Compound C-1-2 of triazine boronic acid pinacolester, 0.03 equivalents of tetrakistriphenylphosphine palladium, and 2 equivalents of potassium carbonate were added thereto, and the mixture was heated and refluxed under a nitrogen environment. After 18 hours, the reaction solution was cooled down, and a solid precipitated therein was filtered and washed with water (500 mL). The solid was recrystallized with 500 mL of monochlorobenzene to obtain Compound C-1 (26 g).

LC/MS calculated for: C42H26N6O. Exact Mass: 630.2168 found for: 631.22 [M+H].

Synthesis Example 17: Synthesis of Compound C-3

[Reaction Scheme 17]

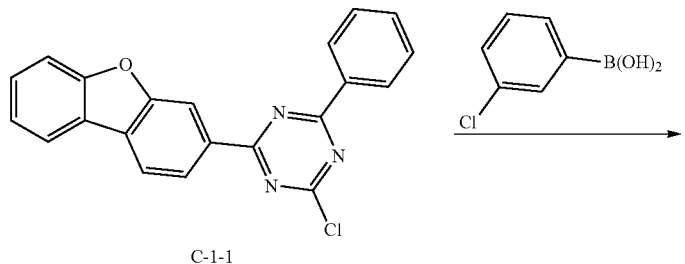

C-1-1

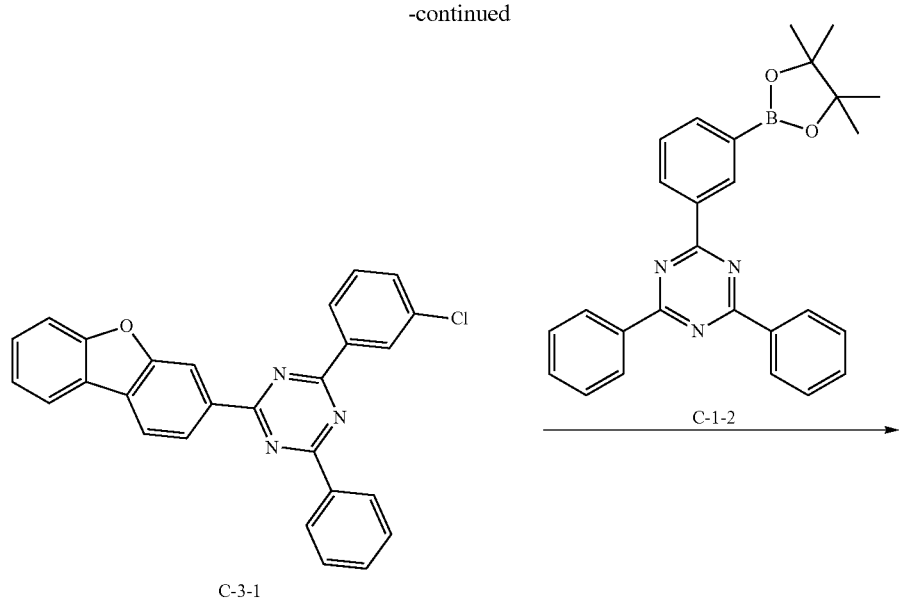

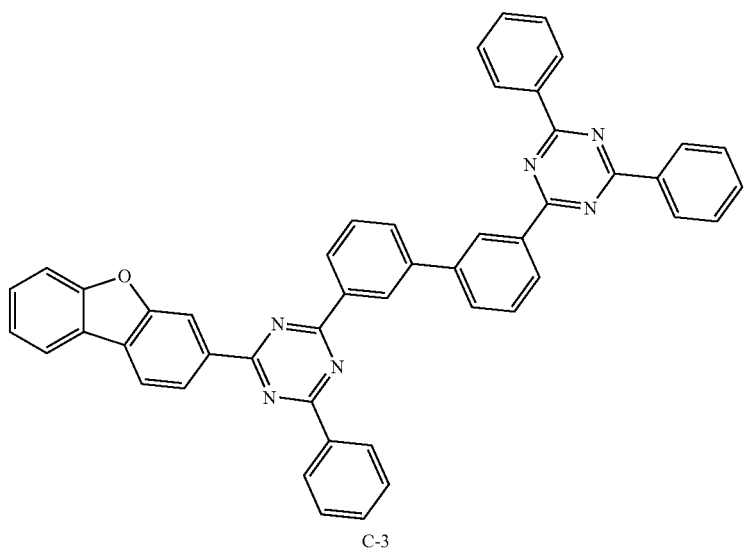

a) Synthesis of Intermediate C-3-1

Intermediate C-3-1 was synthesized according to the same method as b) of Synthesis Example 16 by using 1 equivalent of Intermediate C-1-1 and 1.1 equivalents of 3-chlorophenylboronic acid.

b) Synthesis of Compound C-3

Compound C-3 was synthesized according to the same method as b) of Synthesis Example 16 by using Intermediate C-3-1 and 1.1 equivalents of Intermediate C-1-2.

LC/MS calculated for: C48H30N6S. Exact Mass: 706.2481 found for: 707.25 [M+H].

Synthesis Example 18: Synthesis of Compound C-10
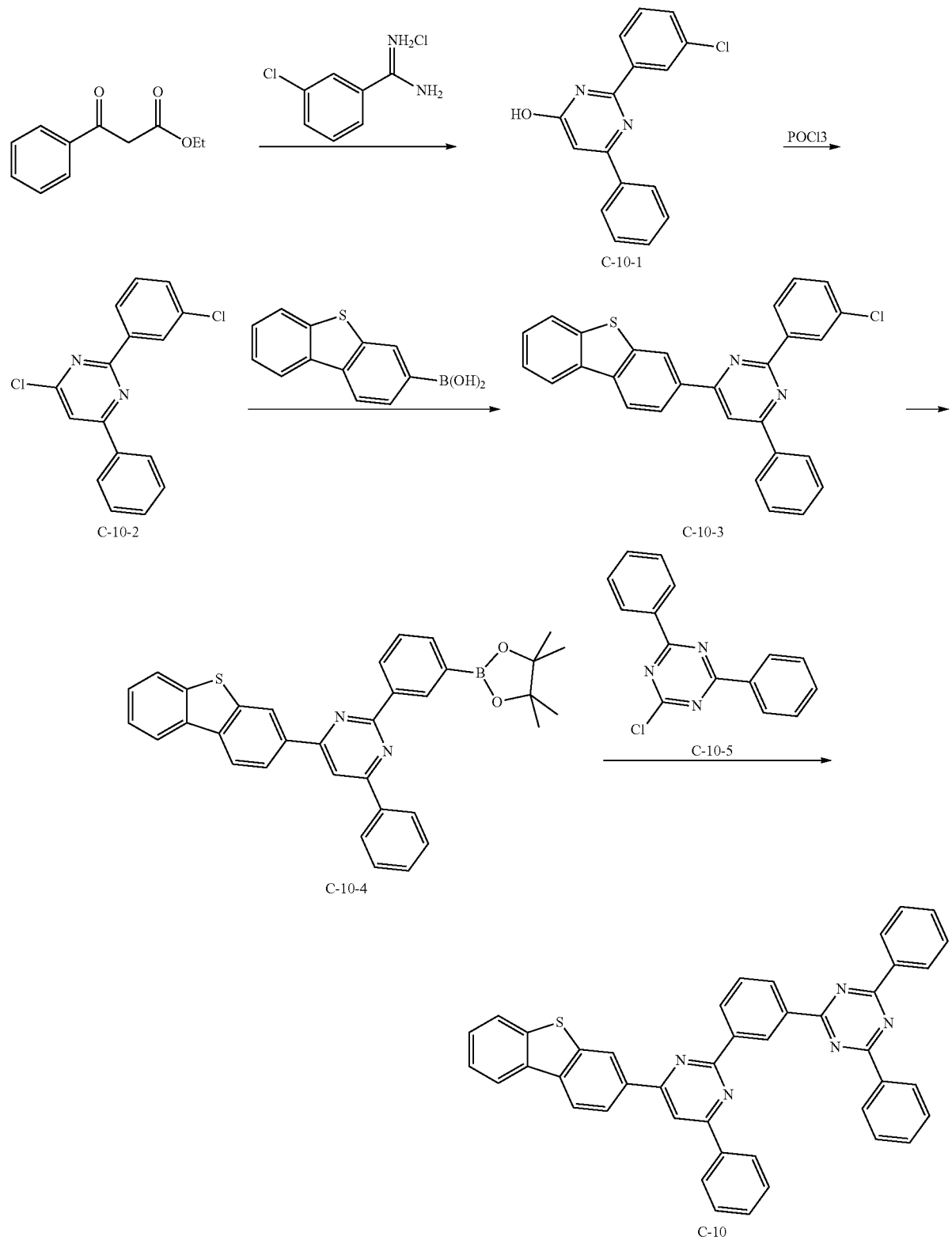

a) Synthesis of Intermediate C-10-1

1 equivalent of ethylbenzoylacetate and 1 equivalent of 3-chlorophenyl amidine-hydrochloride were heated and refluxed along with 1 equivalent of sodium methoxide under methanol (0.5 M). A product therefrom was adjusted to have pH of about 6, and a solid therefrom was filtered and washed with a small amount of water. The solid was dried to synthesize Intermediate C-10-1 (50%).

b) Synthesis of Intermediate C-10-2

1 equivalent of Intermediate C-10-1 and 7 equivalents of phosphorus oxychloride were heated up to 90° C. and reacted for 6 hours. A product therefrom was cooled down and poured into an ice bath to complete a reaction. The obtained solid was dissolved in dichloromethane, extracted to separate an organic layer, and dried under a reduced pressure to synthesize Intermediate C-10-2.

c) Synthesis of Intermediate C-10-3

Intermediate C-10-3 was synthesized according to the same method as a) of Synthesis Example 16 by using 1 equivalent of Intermediate C-10-2 and 1.1 equivalents of dibenzothiophene-3-boronic acid.

d) Synthesis of Intermediate C-10-4

Intermediate C-10-3 (10 g, 20.45 mmol) was added to DMF (100 mL) in a 500 mL round-bottomed flask, 0.05 equivalents of dichlorodiphenylphosphinoferrocene palladium, 1.2 equivalents of bispinacolato diboron, and 2 equivalents of potassium acetate were added thereto, and the mixture was heated and refluxed under a nitrogen atmosphere for 18 hours. The reaction solution was cooled down and then, added to water (1 L) in a dropwise fashion to obtain a solid. The obtained solid was dissolved in boiling toluene to treat with activated carbon and then, filtered in silica gel and concentrated. The concentrated solid was stirred with a small amount of hexane and filtered to obtain Intermediate C-10-4 (80%).

e) Synthesis of Compound C-10

Compound C-10 was synthesized according to the same method as b) of Synthesis Example 16 by using 1 equivalent of Intermediate C-10-4 and 1.1 equivalents of Compound C-10-5 of 2-chloro-4,6-diphenyl-1,3,5-triazine. LC/MS calculated for: C43H27N5S. Exact Mass: 645.1987 found for: 646.20 [M+H].

[Reaction Scheme 19]

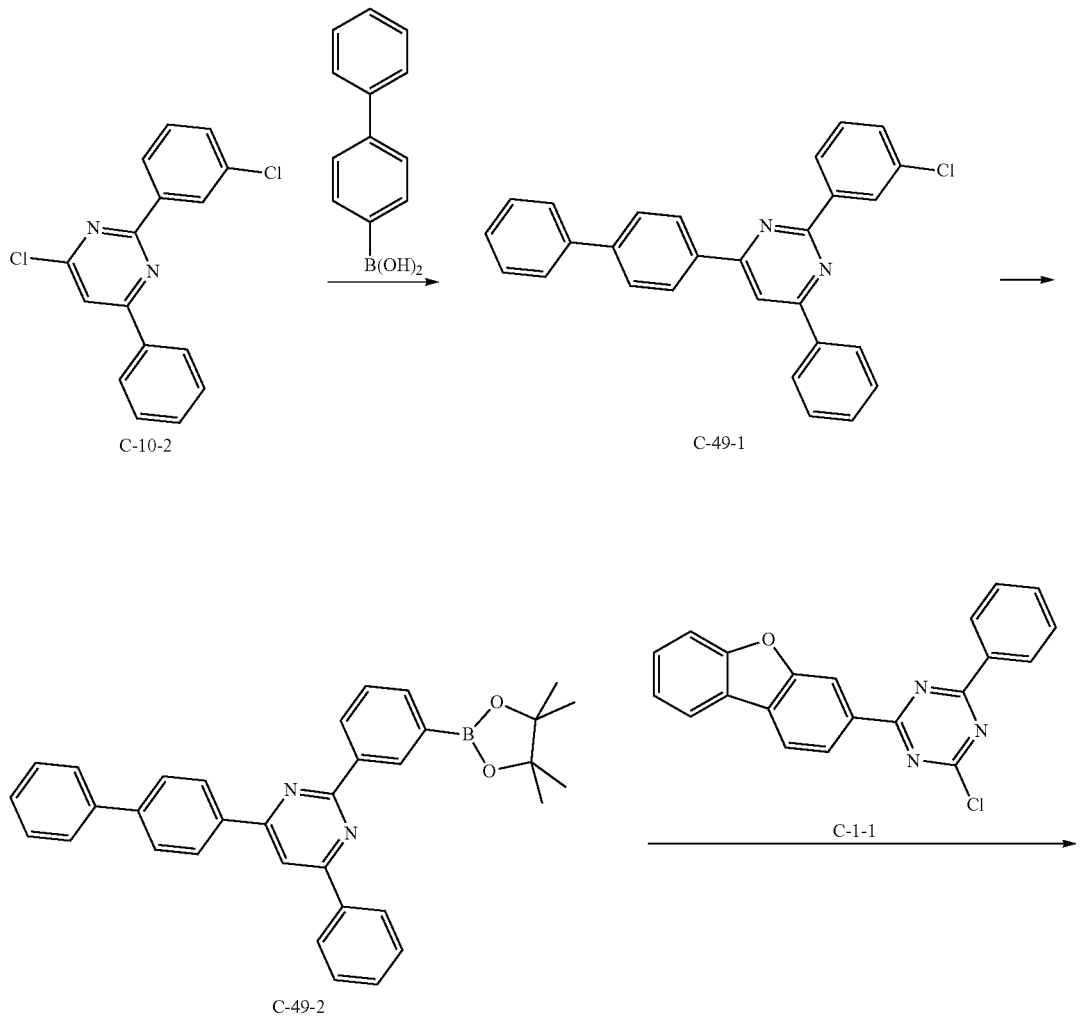

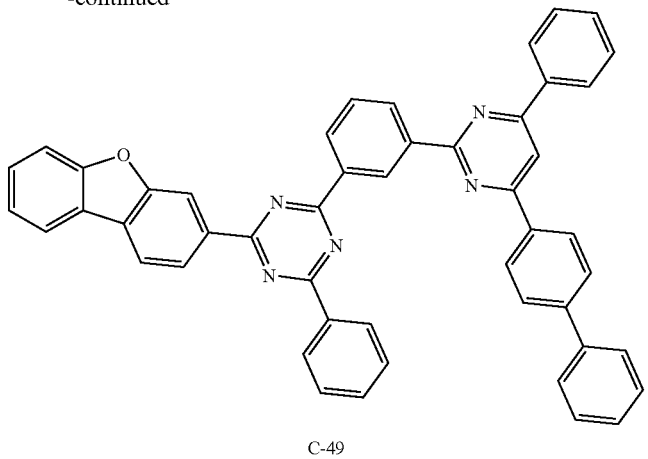

C-49

Synthesis Example 19: Synthesis of Compound C-49 a) Synthesis of Intermediate C-49-1

Intermediate C-49-1 was synthesized according to the same method as b) of Synthesis Example 16 by using 1 equivalent of Intermediate C-10-2 and 1.1 equivalents of 4-phenylbenzene-boronic acid.

b) Synthesis of Intermediate C-49-2

Intermediate C-49-2 was synthesized according to the same method as (d) of Synthesis Example 18 by using 1 equivalent of Intermediate C-49-1.

c) Synthesis of Compound C-49

Compound C-49 was synthesized according to the same method as b) of Synthesis Example 16 by using 1 equivalent of Intermediate C-49-2 and 1.1 equivalents of Intermediate C-1-1.

LC/MS calculated for: C49H31N5O. Exact Mass: 705.2529 found for: 706.26 [M+H].

Synthesis of Second Compound for Organic Optoelectronic Device

Synthesis Example 20: Synthesis of Compound E-84

[Reaction Scheme 20]

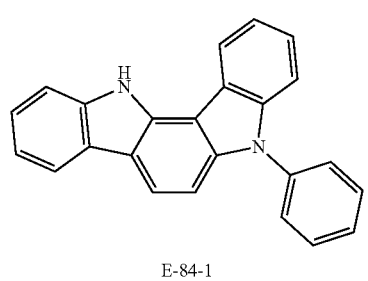

E-84-1

+

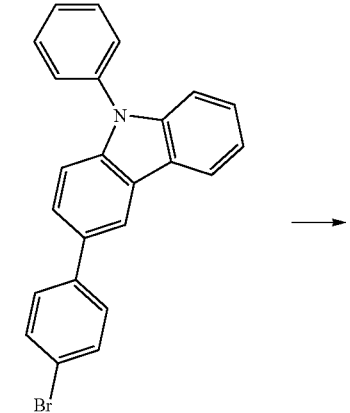

E-84-2

→

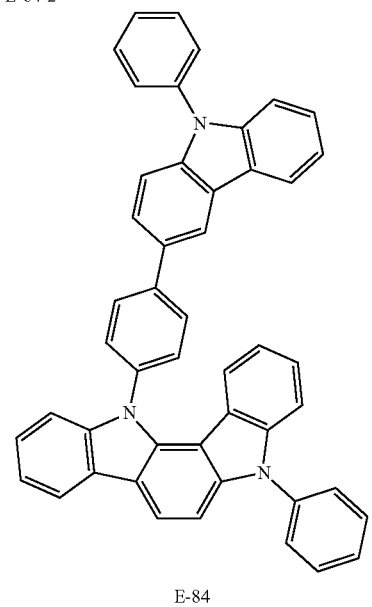

E-84

1 equivalent of Intermediate E-84-1 (5-phenyl-12H-indolo[3,2-c]carbazole, Cas No: 1247053-55-9) and 1 equivalent of Intermediate E-84-2 (3-(4-Bromophenyl)-9-phenylcarbazole, Cas No: 1028647-93-9), 2 equivalents of sodium t-butoxide, and 0.05 equivalents of Pd2(dba)3 were suspended in xylene in a concentration of 0.2 M, tri-tertiary-butylphosphine (0.15 eq) was added thereto, and the mixture was refluxed and stirred for 18 hours. Methanol in 1.5 times more amount of the solvent was added thereto, the obtained mixture was stirred, and a solid obtained therefrom was filtered and washed with water (300 mL). The solid was recrystallized by using monochlorobenzene to obtain Compound E-84 (85%). LC/MS calculated for: C48H31N3. Exact Mass: 649.2518 found for 650.25 [M+H].

Comparative Synthesis Example 1: Comparative Compound 1

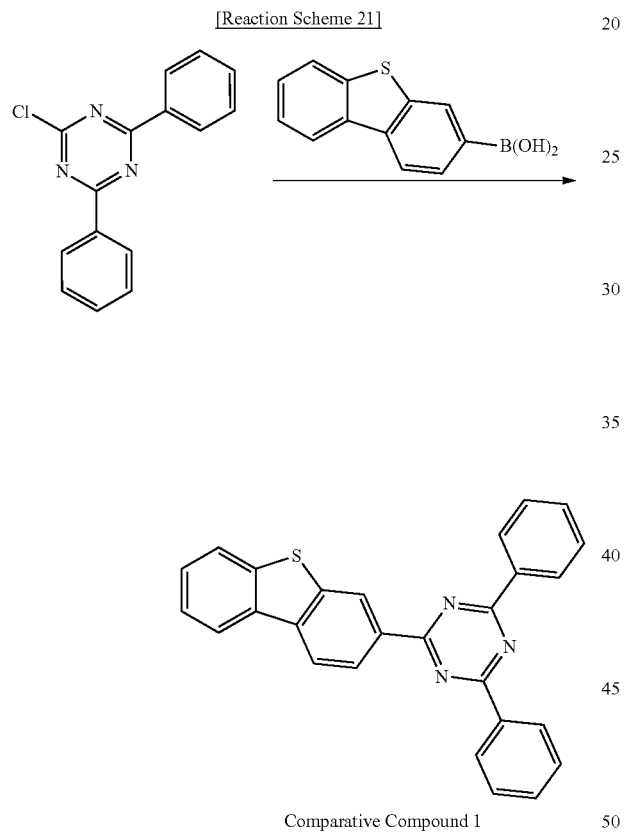

Comparative Compound 1

Comparative Compound 1 was synthesized according to the same method as b) of Synthesis Example 1 by using 2-chloro-4,6-diphenyltriazine and dibenzothiophene-3-boronic acid.

LC/MS calculated for: C27H17N3S. Exact Mass: 415.1143 found for 416.11 [M+H].

Comparative Synthesis Example 2: Comparative Compound 2

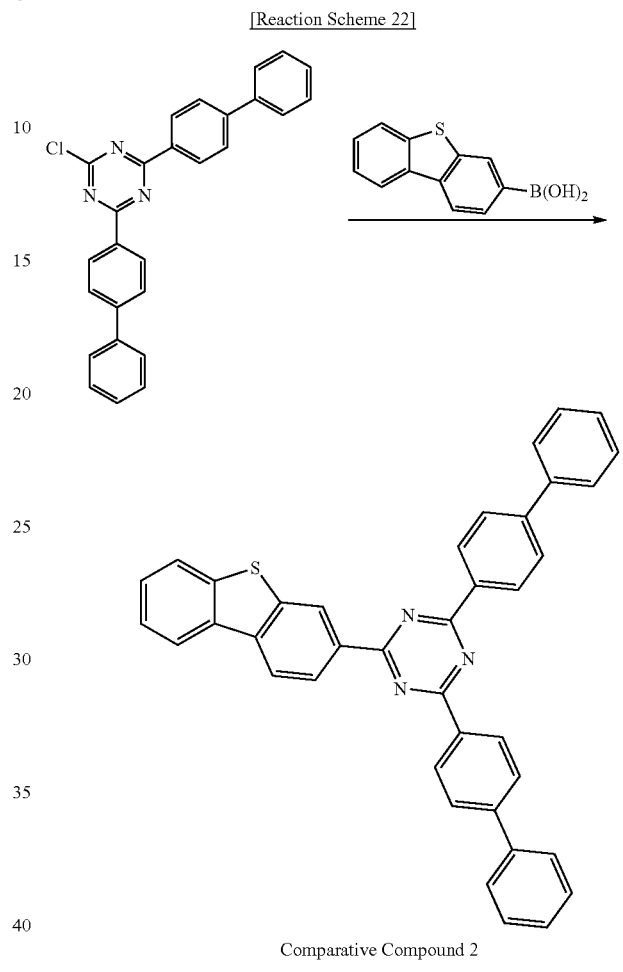

Comparative Compound 2

Comparative Compound 2 was synthesized according to the same method as b) of Synthesis Example 1 by using 2,4-bis([1,1'-biphenyl]-4-yl)-6-chloro-1,3,5-triazine and dibenzothiophene-3-boronic acid.

LC/MS calculated for: C39H25N3S. Exact Mass: 567.1769 found for 568.18 [M+H].

Comparative Synthesis Example 3: Comparative Compound 3

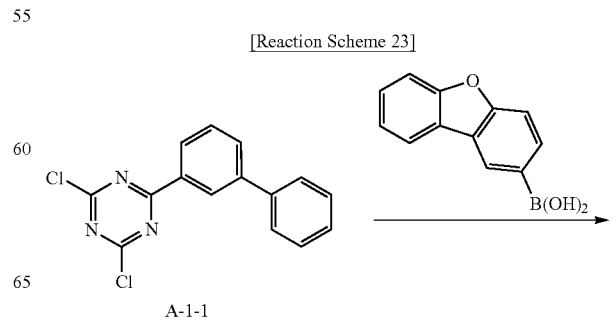

A-1-1

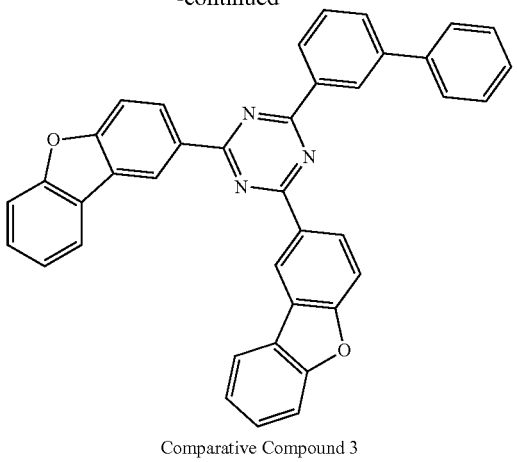

Comparative Compound 3

Comparative Compound 3 was synthesized according to the same method as b) of Synthesis Example 1 by using Intermediate A-1-1 and dibenzofuran-2-boronic acid.

LC/MS calculated for: C39H23N3O. Exact Mass: 565.1790 found for 566.18 [M+H].

Comparative Synthesis Example 4: Comparative Compound 4

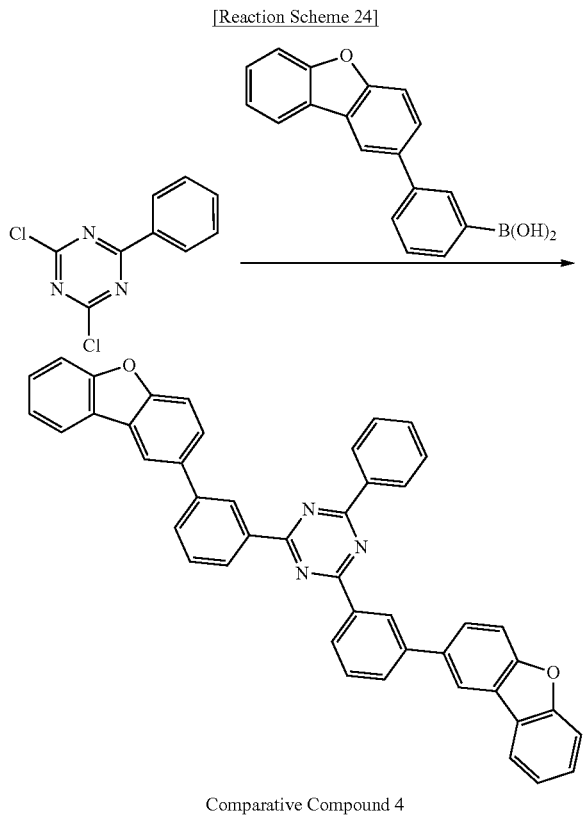

Comparative Compound 4

Comparative Compound 4 was synthesized according to the same method as b) of Synthesis Example 1 by using 2,4-dichloro-6-phenyl-1,3,5-triazine and dibenzofuran-2-yl-3-phenylboronic acid.

LC/MS calculated for: C39H23N3O. Exact Mass: 565.1790 found for 566.18 [M+H].

Comparative Synthesis Example 5: Comparative Compound 5

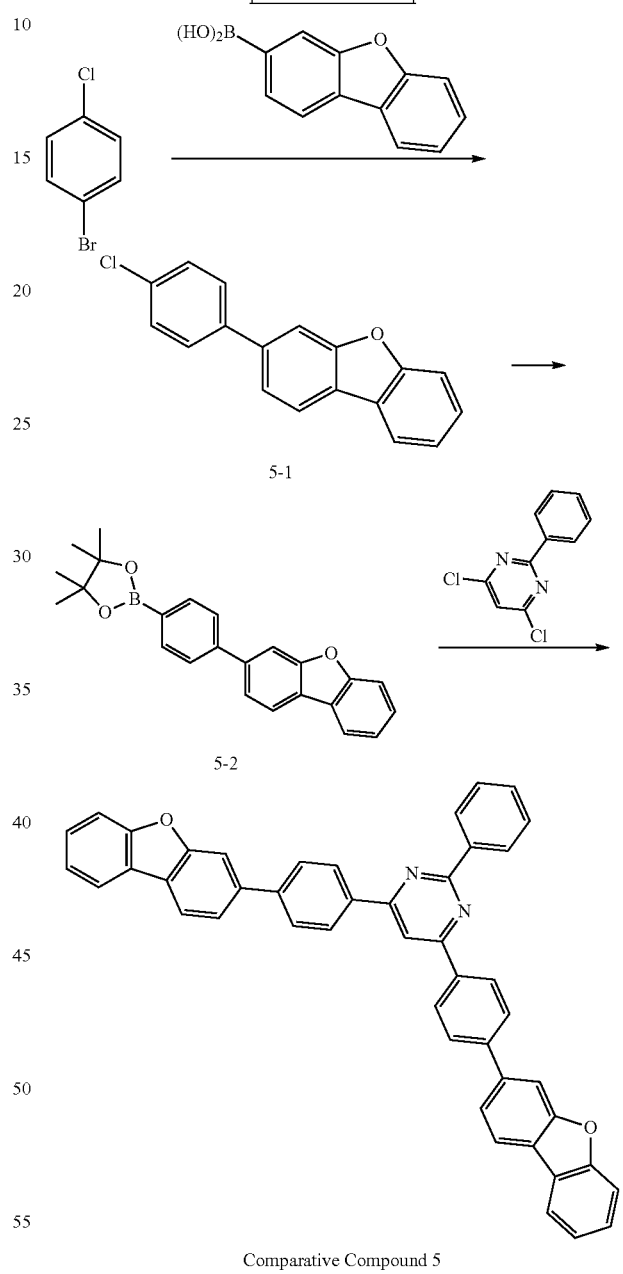

Comparative Compound 5 a) Synthesis of Intermediate 5-1

Intermediate 5-1 was synthesized according to the same method as b) of Synthesis Example 1 by using 1-bromo-4-chlorobenzene and dibenzofuran-3-boronic acid.

b) Synthesis of Intermediate 5-2

Intermediate 5-1 (328 mmol) was dissolved in dimethylforamide (DMF, 1.0 L), bis(pinacolato)diboron (100 g, 394 mmol), (1,1'-bis(diphenylphosphine)ferrocene)dichloropalladium (11) (2.68 g, 3.28 mmol), and potassium acetate (96.6 g, 984 mmol) were added thereto, and the mixture was heated and refluxed at 150° C. for 20 hours. When a reaction was complete, water was added to the reaction solution, and the obtained mixture was filtered and dried in a vacuum oven. The obtained residue was separated and purified through flash column chromatography to obtain Intermediate 5-2 (71%).

c) Synthesis of Comparative Compound 5

Comparative Compound 5 was synthesized according to the same method as b) of Synthesis Example 1 by using Intermediate 5-2 and 4,6-dichloro-2-phenyl-1,3-pyrimidine.

LC/MS calculated for: C46H28N2O2. Exact Mass: 640.2151 found for: 641.22 [M+H].

Manufacture of Organic Light Emitting Diode

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound A-1 of Synthesis Example 1 and Compound E-15 simultaneously as hosts and 10 wt % of tris(2-phenylpyridine)iridium (III) [Ir(ppy)$_3$] as a dopant. Herein, Compound A-1 and Compound E-15 were used in a 7:3 ratio and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically a structure of ITO/Compound A 700 Å/Compound B 50 Å/Compound C 1020 Å/EML[Compound A-1:E-15:Ir(ppy)$_3$=27 wt %:63 wt %:10 wt %] 400 Å/Compound D:Liq 300 Å/Liq 15 Å/Al 1200 Å.

Compound A: N4,N4'-diphenyl-N4,N4'-bis(9-phenyl-9H-carbazol-3-yl)biphenyl-4,4'-diamine, Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine, and Compound D: 8-(4-(4,6-di(naphthalen-2-yl)-1,3,5-triazin-2-yl)phenyl)quinolone.

Examples 2 to 22

Organic light emitting diodes according to Examples 2 to 22 were respectively manufactured according to the same method as Example 1 by using the first and second hosts of the present invention as shown in Tables 1 and 2.

Comparative Examples 1 to 5

Organic light emitting diodes according to Comparative Examples 1 to 5 were respectively manufactured according to the same method as Example 1 by using Comparative Compounds 1 to 5 relative to E-84 in a ratio of 3:7.

Evaluation 1: Confirmation of Synergic Effect of Luminous Efficiency and Life-Span Luminous efficiency and life-span characteristics of each organic light emitting diode according to Examples 1 to Example 22 and Comparative Examples 1 to Comparative Example 5 were measured. Specific measurement methods are as follows, and the results are shown in Table 1 and Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T97 life-spans of the organic light emitting diodes according to Examples 1 to and Comparative Example 1 to Comparative Example 5 were measured as a time when their luminance decreased down to 90% relative to the initial luminance (cd/m$^2$) after emitting light with 5000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$, and the results are shown in Table 1.

TABLE 1

Mixed host diode effect: in case of triazine

| | First host | Second host | Ratio of First host:Second host | Color | Life-span (T90) | Vd |
|---|---|---|---|---|---|---|
| Example 1 | A-1 | E-15 | 3:7 | green | 380 | 3.7 |
| Example 2 | A-1 | E-55 | 3:7 | green | 320 | 3.4 |
| Example 3 | A-1 | E-84 | 3:7 | green | 400 | 3.6 |
| Example 4 | A-1 | E-90 | 3:7 | green | 380 | 3.8 |
| Example 5 | A-2 | E-84 | 3:7 | green | 520 | 3.6 |
| Example 6 | A-5 | E-84 | 3:7 | green | 430 | 3.6 |
| Example 7 | B-1 | E-84 | 3:7 | green | 370 | 3.8 |
| Example 8 | B-7 | E-84 | 3:7 | green | 350 | 3.9 |
| Example 9 | B-9 | E-84 | 3:7 | green | 430 | 3.8 |
| Example 10 | B-11 | E-84 | 3:7 | green | 400 | 3.9 |
| Example 11 | B-13 | E-84 | 3:7 | green | 490 | 3.9 |
| Example 12 | B-14 | E-84 | 3:7 | green | 400 | 3.8 |
| Example 13 | B-16 | E-84 | 3:7 | green | 470 | 3.9 |
| Example 14 | B-53 | E-84 | 3:7 | green | 500 | 3.6 |
| Example 15 | C-1 | E-84 | 3:7 | green | 430 | 3.4 |
| Example 16 | C-3 | E-84 | 3:7 | green | 380 | 3.5 |
| Example 17 | C-49 | E-84 | 3:7 | green | 380 | 3.5 |
| Comparative Example 1 | Comparative Compound 1 | E-84 | 3:7 | green | 160 | 4.0 |
| Comparative Example 2 | Comparative Compound 2 | E-84 | 3:7 | green | 220 | 3.8 |
| Comparative Example 3 | Comparative Compound 3 | E-84 | 3:7 | green | 100 | 4.3 |

TABLE 1-continued

Mixed host diode effect: in case of triazine

| | First host | Second host | Ratio of First host:Second host | Color | Life-span (T90) | Vd |
|---|---|---|---|---|---|---|
| Comparative Example 4 | Comparative Compound 4 | E-84 | 3:7 | green | 260 | 4.5 |

TABLE 2

Mixed host diode effect: in case of pyrimidine

| | First host | Second host | Ratio of First host:Second host | Color | Efficiency (Cd/A) | Life-span (T90) |
|---|---|---|---|---|---|---|
| Example 18 | A-15 | E-84 | 3:7 | green | 50 | 300 |
| Example 19 | A-21 | E-84 | 3:7 | green | 51 | 320 |
| Example 20 | B-70 | E-84 | 3:7 | green | 51 | 330 |
| Example 21 | B-78 | E-84 | 3:7 | green | 51 | 300 |
| Example 22 | C-10 | E-84 | 3:7 | green | 50 | 370 |
| Comparative Example 5 | Comparative Compound 5 | E-84 | 3:7 | green | 45 | 120 |

Referring to Table 1, when the first and second hosts of the present invention were used, the present invention having a structural feature of linking dibenzofuran with triazine at No. 3 and/or additionally including a meta substituted aryl group showed an effect of greater than or equal to 5 times improving a life-span at maximum compared with Comparative Example using a mixed host of the same second host.

This effect was equally shown in the pyrimidine core as well as the triazine core. Accordingly, referring to data of a corresponding device, when dibenzofuran or dibenzothiophene was directly linked with an ET core group, the device manufactured by using a corresponding material showed improved life-span through effective LUMO expansion and cyclic fusion.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A composition for an organic optoelectronic device, comprising
    a first compound for an organic optoelectronic device represented by one of Chemical Formula 1A, Chemical Formula 1B, and Chemical Formula 1C; and
    a second compound for an organic optoelectronic device consisting of a moiety represented by Chemical Formula 2 and a moiety represented by Chemical Formula 3:

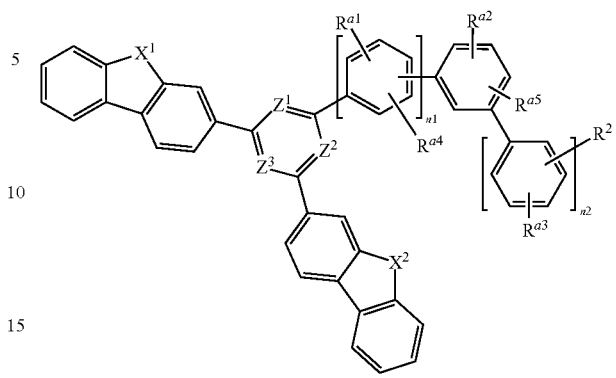

[Chemical Formula 1A]

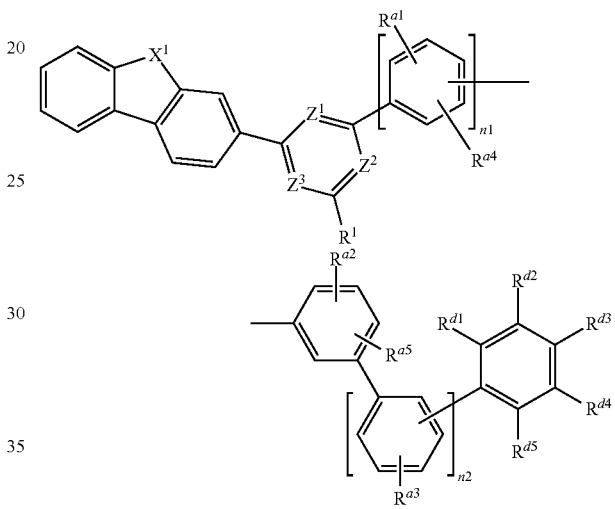

[Chemical Formula 1B]

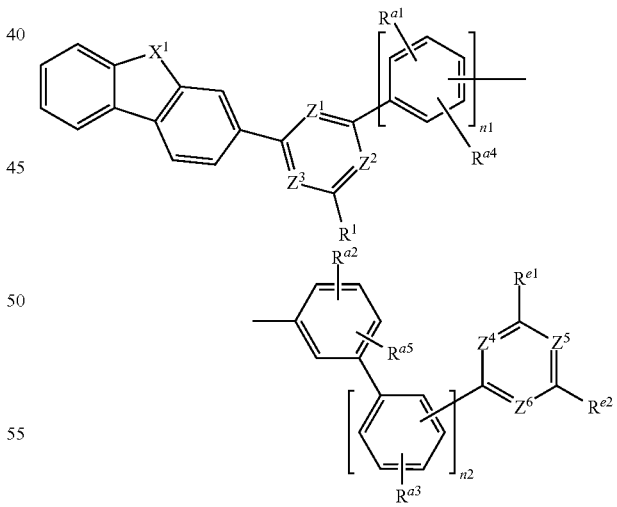

[Chemical Formula 1C]

wherein, in Chemical Formula 1A, Chemical Formula 1B, and Chemical Formula 1C, $Z^1$ to $Z^3$ are independently N or CH, at least two of $Z^1$ to $Z^3$ are N, $Z^4$ to $Z^6$ are independently N or $CR^e$, at least two of $Z^4$ to $Z^6$ are N, $X^1$ and $X^2$ are independently O or S, $R^1$, $R^2$, $R^e$, $R^{e1}$, $R^{e2}$ are independently a substituted or unsubstituted C6 to C30 aryl group, a substituted or unsubstituted C2 to C30 heterocyclic group, or a combination thereof, $R^e$, $R^{e1}$, and $R^{e2}$ are independently present or adjacent groups thereof are linked with each other to form a substituted or unsubstituted aliphatic, aromatic, or heteroaromatic monocyclic or polycyclic ring, $R^{a1}$ to $R^{a5}$ and $R^{d1}$ to $R^{d5}$ are independently hydrogen, deuterium, a cyano group, a nitro group, a substituted or unsubstituted C1 to C10 alkyl group, a substituted or unsubstituted C6 to C30 aryl group, a substituted or unsubstituted C2 to C20 heterocyclic group, or a combination thereof, $R^{d1}$ to $R^{d5}$ are independently present or adjacent groups thereof are linked with each other to form a substituted or unsubstituted aliphatic, aromatic, or heteroaromatic monocyclic or polycyclic ring, and n1 and n2 are independently 0 or 1;

[Chemical Formula 2]

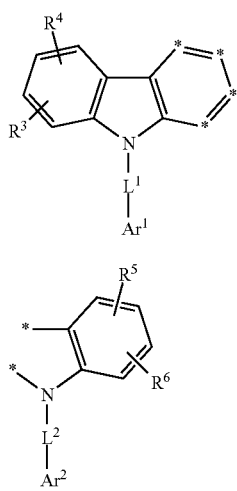

[Chemical Formula 3]

wherein, in Chemical Formulae 2 and 3, $Ar^1$ and $Ar^2$ are independently a substituted or unsubstituted C6 to C30 aryl group, a substituted or unsubstituted C2 to C30 heterocyclic group, or a combination thereof, two adjacent *'s of Chemical Formula 2 are bound to two adjacent *'s of Chemical Formula 3 to provide a fused ring and *'s of not providing the fused ring in Chemical Formula 2 are independently $C-L^a-R^c$, $R^c$ and $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^a$, $L^1$, and $L^2$ are independently a single bond, a substituted or unsubstituted C6 to C30 arylene group, a substituted or unsubstituted C2 to C30 heteroarylene group, or a combination thereof;

wherein the "substituted" of Chemical Formulae 1 to 3 refers to replacement of at least one hydrogen by deuterium, a C1 to C4 alkyl group, a C6 to C18 aryl group, or a C2 to C18 heteroaryl group.

2. The composition for an organic optoelectronic device of claim 1, wherein the $R^1$ and $R^2$ are independently a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, or a substituted or unsubstituted quinoxalinyl group.

3. The composition for an organic optoelectronic device of claim 1, wherein the $R^1$ and $R^2$ are independently selected from substituents of Group I:

[Group I]

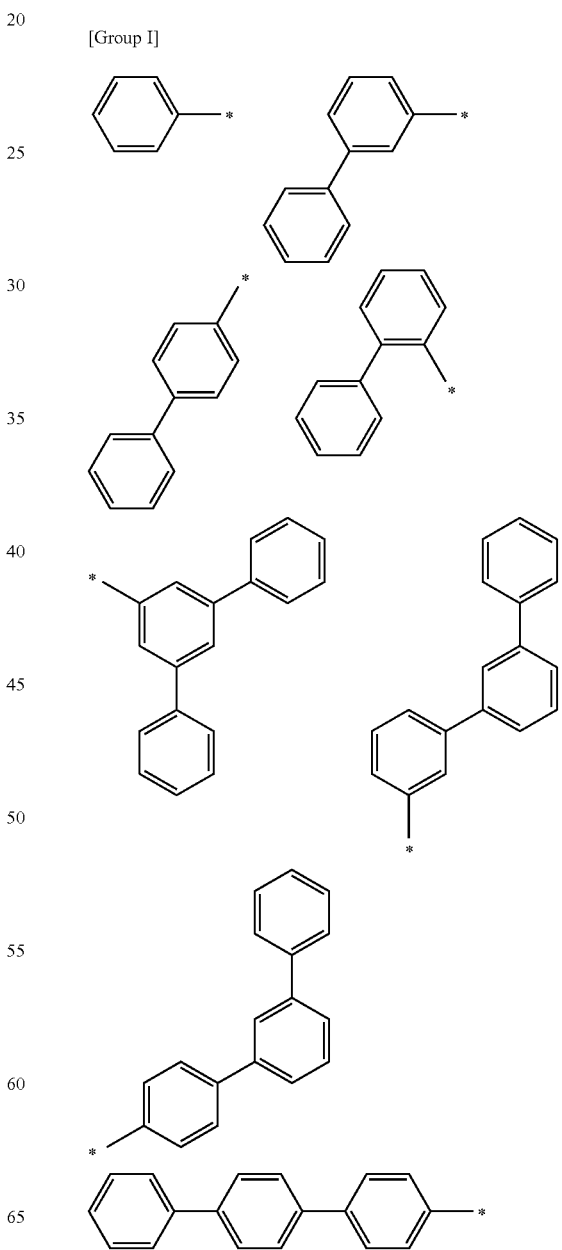

-continued

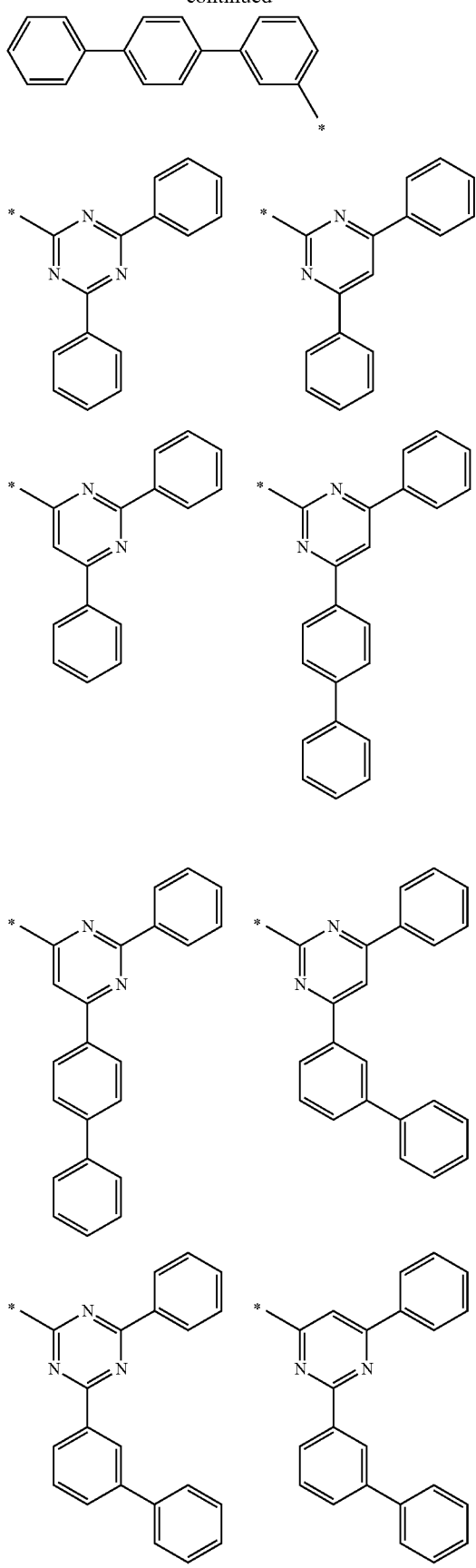

-continued

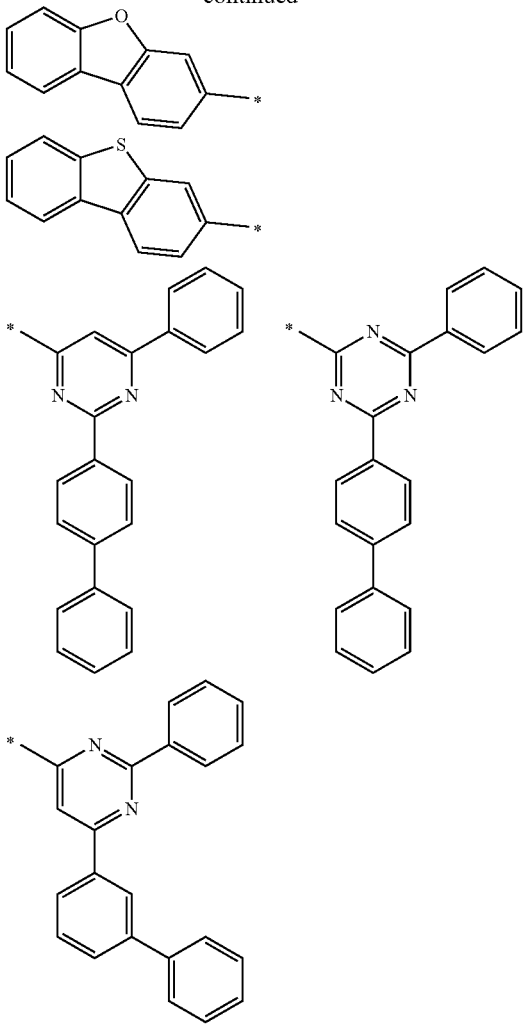

wherein, in Group I, is a linking point with an adjacent atom.

4. The composition for an organic optoelectronic device of claim 1, wherein:

R¹, R², R^{e1}, and R^{e2} are independently a substituted or unsubstituted phenyl group, a substituted or unsubstituted biphenyl group, a substituted or unsubstituted naphthyl group, a substituted or unsubstituted dibenzofuranyl group, a substituted or unsubstituted dibenzothiophenyl group, or a substituted or unsubstituted fluorenyl group, $R^{a1}$ to $R^{a5}$ and $R^{d1}$ to $R^{d5}$ are independently hydrogen, deuterium, a cyano group, a substituted or unsubstituted C1 to C4 alkyl group, a substituted or unsubstituted phenyl group, a substituted or unsubstituted biphenyl group, a substituted or unsubstituted naphthyl group, a substituted or unsubstituted terphenyl group, a substituted or unsubstituted fluorenyl group, or a combination thereof, $R^{d1}$ to $R^{d5}$ are independently present or adjacent groups thereof are linked with each other to form a substituted or unsubstituted aliphatic, aromatic, or heteroaromatic monocyclic or polycyclic ring.

5. The composition for an organic optoelectronic device of claim 1, wherein the second compound for an organic optoelectronic device consisting of a combination of the moiety represented by Chemical Formula 2 and the moiety represented by Chemical Formula 3 is represented by at least one of Chemical Formulae 2-I to 2-V:

[Chemical Formula 2-I]

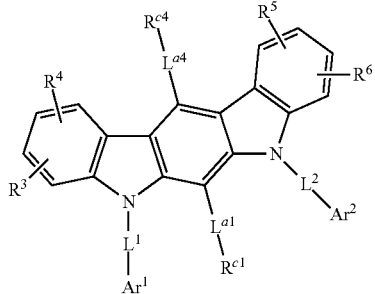

[Chemical Formula 2-II]

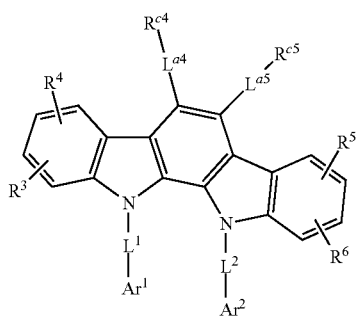

[Chemical Formula 2-III]

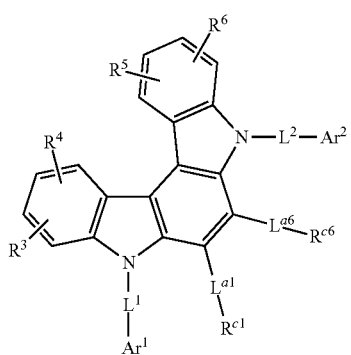

[Chemical Formula 2-IV]

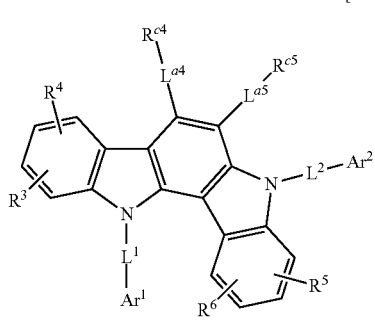

-continued

[Chemical Formula 2-V]

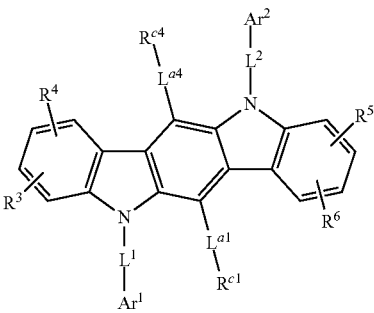

wherein, in Chemical Formulae 2-1 to 2-V, $Ar^1$ and $Ar^2$ are independently a substituted or unsubstituted C6 to C30 aryl group, a substituted or unsubstituted C2 to C30 heterocyclic group, or a combination thereof, $L^{a1}$, $L^{a4}$ to $L^{a6}$, $L^1$ and $L^2$ are independently a single bond, a substituted or unsubstituted C6 to C30 arylene group, a substituted or unsubstituted C2 to C30 heteroarylene group, or a combination thereof, and $R^{c1}$, to $R^{c4}$ to $R^{c6}$, and $R^3$ to $R^6$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof.

6. The composition for an organic optoelectronic device of claim 1, wherein the $L^1$ and $L^2$ are independently a single bond, a substituted or unsubstituted phenylene group, a substituted or unsubstituted biphenylene group, a substituted or unsubstituted pyridylene group, or a substituted or unsubstituted pyrimidylene group, and the $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted fluorenyl group, a substituted or unsubstituted carbazolyl group, a substituted or unsubstituted pyridyl group, a substituted or unsubstituted pyrimidinyl group, a substituted or unsubstituted triazinyl group, a substituted or unsubstituted dibenzofuranyl group, or a substituted or unsubstituted dibenzothiophenyl group.

7. An organic optoelectronic device, comprising
an anode and a cathode facing each other, and
at least one organic layer disposed between the anode and the cathode, and
the organic optoelectronic device includes the composition for an organic optoelectronic device of claim 1.

8. The organic optoelectronic device of claim 7, wherein the organic layer includes a light emitting layer,
wherein the light emitting layer includes the composition for an organic optoelectronic device.

9. The organic optoelectronic device of claim 8, wherein the composition for an organic optoelectronic device is included as a host of the light emitting layer.

10. A display device comprising the organic optoelectronic device of claim 7.

* * * * *